(12) United States Patent
Geigenmuller et al.

(10) Patent No.: US 9,176,113 B1
(45) Date of Patent: Nov. 3, 2015

(54) METHODS AND SYSTEMS FOR DETERMINING AUTISM SPECTRUM DISORDER RISK

(71) Applicant: SynapDx Corporation, Lexington, MA (US)

(72) Inventors: Ute Geigenmuller, Lexington, MA (US); Doris Damian, Lexington, MA (US); Maciej Pacula, Lexington, MA (US); Mark A. DePristo, Lexington, MA (US)

(73) Assignee: SynapDx Corporation, Lexington, MA (US)

( * ) Notice: Subject to any disclaimer, the term of this patent is extended or adjusted under 35 U.S.C. 154(b) by 0 days.

(21) Appl. No.: 14/633,558

(22) Filed: Feb. 27, 2015

Related U.S. Application Data

(63) Continuation-in-part of application No. 14/493,141, filed on Sep. 22, 2014.

(60) Provisional application No. 61/978,773, filed on Apr. 11, 2014, provisional application No. 62/002,169, filed on May 22, 2014.

(51) Int. Cl.
   *G01N 33/50* (2006.01)
   *G01N 33/68* (2006.01)
   *G01N 33/70* (2006.01)
   *G01N 33/82* (2006.01)

(52) U.S. Cl.
   CPC ............ *G01N 33/50* (2013.01); *G01N 33/6896* (2013.01); *G01N 33/70* (2013.01); *G01N 33/82* (2013.01); *G01N 2560/00* (2013.01); *G01N 2570/00* (2013.01); *G01N 2800/28* (2013.01); *G01N 2800/2814* (2013.01)

(58) Field of Classification Search
   CPC ... G01N 33/50; G01N 33/6896; G01N 33/70; G01N 33/82
   See application file for complete search history.

(56) References Cited

U.S. PATENT DOCUMENTS

| | | | |
|---|---|---|---|
| 5,686,311 | A | 11/1997 | Shaw |
| 8,273,575 | B2 | 9/2012 | Goodenowe |
| 2002/0019407 | A1* | 2/2002 | Rusche et al. ............... 514/263 |
| 2007/0255113 | A1 | 11/2007 | Grimes |
| 2008/0133141 | A1 | 6/2008 | Frost |
| 2012/0190055 | A1 | 7/2012 | Cezar et al. |
| 2012/0322088 | A1 | 12/2012 | Goodenowe |
| 2014/0065132 | A1* | 3/2014 | Hsiao et al. ............... 424/130.1 |

FOREIGN PATENT DOCUMENTS

| | | |
|---|---|---|
| WO | WO-2004/059293 A2 | 7/2004 |
| WO | WO-2006/090185 A1 | 8/2006 |
| WO | WO-2006/121952 A2 | 11/2006 |
| WO | WO-2008/021515 A2 | 2/2008 |
| WO | WO-2009/151967 A1 | 12/2009 |
| WO | WO-2011/139914 A1 | 11/2011 |
| WO | WO-2013/132074 A2 | 9/2013 |

OTHER PUBLICATIONS

Al-Gadani, Y., El-Ansary, A., Attas, O. & Al-Ayadhi, L. Metabolic biomarkers related to oxidative stress and antioxidant status in Saudi autistic children. Clinical Biochemistry 42, 1032-1040 (2009).*
Human Metabolome Database Accession No. HMDB01067, Showing Metabocard for N-Acetylaspartylglutamic Acid, http://www.hmdb.ca/metabolites/HMDB01067, 5 pages, (Nov. 16, 2005).*
Adams, J. B. et al., Nutritional and metabolic status of children with autism vs. neurotypical children, and the association with autism severity, Nutrition & Metabolism, 8:34:1-32, (2011).
Aldred, S. et al., Plasma Amino Acid Levels in Children with Autism and Their Families, Journal of Autism and Development Disorders, 33:1:93-97, (2003).
Armstrong, M. et al., Analysis of 25 Underivatized Amino Acids in Human Plasma Using Ion-Pairing Reversed-Phase Liquid Chromatography/Time-Of-Flight Mass Spectrometry; Rapid Communications in Mass Spectrometry, 21:2717-2726, (2007).
Boccuto, L. et al., Decreased tryptophan metabolism in patients with autism spectrum disorders, Molecular Autism, 4:16, (2013).
Bourcier, S.et al., Use of Diagnostic Neutral Losses for Structural Information on Unknown Aromatic Metabolites: An Experimental and Theoretical Study, Rapid Commun Mass Spectrom. 23:(1):93-103 (2009).
Bull, G. et al., Indolyl-3-acryloylglycine (IAG) is a putative diagnostic urinary marker for autism spectrum disorders, Med. Sci. Monit, 9(10):CR422-425, (2003).
Burgess, N. K. et al., Hyperserotoninemia and Altered Immunity in Autism, J. Autism Dev. Disord. 36:697-704, (2006).
Cao, L. et al., *p*-Cresol Sulfate is the Dominant Component of Urinary Myelin Basic Protein Like Material, Archives of Biochemistry and Biophysics, 377:1:9-21, (2000).
Chen, J. J. et al., Maintenance of Serotonin in the Intestinal Mucosa and Ganglia of Mice that Lack the High-Affinity Serotonin Transporter: Abnormal Intestinal Motility and the Expression of Cation Transporters, The Journal of Neuroscience, 21(16):6348-6361, (2001).
Clayton, T. Andrew, Metabolic differences underlying two distinct rat urinary phenotypes, a suggested role for gut microbial metabolism of phenylalanine and a possible connection to autism, FEBS Letters, 586:956-961, (2012).
Croonenberghs, J. et al., Peripheral Markers of Serotonergic and Noradrenergtic Function in Post-Pubertal, Caucasian Males with Autistic Disorder, Neuropsychopharmacology, 22:3:275-283, (2000).

(Continued)

*Primary Examiner* — Soren Harward
(74) *Attorney, Agent, or Firm* — William R. Haulbrook; Robert N. Sahr; Choate, Hall & Stewart LLP

(57) ABSTRACT

In certain embodiments, the invention stems from the discovery that analysis of population distribution curves of metabolite levels in blood can be used to facilitate predicting risk of autism spectrum disorder (ASD) and/or to differentiate between ASD and non-ASD developmental delay (DD) in a subject. In certain aspects, information from assessment of the presence, absence, and/or direction (upper or lower) of a tail effect in a metabolite distribution curve is utilized to predict risk of ASD and/or to differentiate between ASD and DD.

5 Claims, 54 Drawing Sheets

(56) References Cited

OTHER PUBLICATIONS

De Angelis, M. et al., Fecal microbiota and metabolome of children with autism and pervasive developmental disorder not othwerise specified, PLOS One 8:e76993 (2013).
de Bree, P. K. et al., Diagnosis of Inherited Adenylosuccinase Deficiency by Thin-Layer Chromatography of Urinary Imidazoles and by Automated Cation Exchange Column Chromatography of Purines, Clin. Chim. Acta, 156(3):279-87, (1986).
Dhillon, S. et al., Genetics and Mitochondrial Abnormalities in Autism Spectrum Disorders: A Review, Current Genomics, 12:322-332, (2011).
El-Ansary, A. K. et al., Plasma fatty acids as diagnostic markers in autistic patients from Saudi Arabia, Lipids in Health and Disease, 10:62:1-8, (2011).
Emond, P. et al., GC-MS-based urine metabolic profiling of autism spectrum disorders, Anal. Bioanal. Chem. 405:5291-5300 (2013).
Evans, C. et al., Altered amino acid excretion in children with autism, Nutritional Neuroscience 11:1:9-17, (2008).
Finegold, S. M. et al., Gastrointestinal Microflora Studies in Late-Onset Autism, CID, 35:(Supple 1), (2002).
Frye, R. E. et al., Unique acyl-carnitine profiles are potential biomarkers for acquired mitochondrial disease in autism spectrum disorder, Transl. Psychiatry, 3:1-10, (2013).
Gabriele, S. et al., Blood serotonin levels in autism spectrum disorder: A systematic review and meta-analysis, European Neuropsychopharmacology, pp. 1-11, (2014).
Geier, D.A. et al., A Prospective Study of Transsulfuration Biomarkers in Autistic Disorders, Neurochemical Research, 34(2):386-393 (2008).
Ghezzo, A. et al., Oxidative Stress and Erythrocyte Membrane Alterations in Children with Autism: Correlation with Clinical Features, PLOS One, 8:6:e66418:1-14, (2013).
Goh, S. et al., Mitochondrial Dysfunction as a Neurobiological Subtype of Autism Spectrum Disorder Evidence From Brain Imaging, Jama. Psychiatry, 7 pgs., (2014).
Human Metabolome Database Accession No. HMDB00099, Showing Metabocard for L-Cystathionine, http://www.hmdb.ca/metabolites/HMDB00099, 8 pages, (Nov. 16, 2005).
Human Metabolome Database Accession No. HMDB00450, Showing Metabocard for 5-Hydroxylysine, http://www.hmdb.ca/metabolities/HMDB00450, 6 pages, (Nov. 16, 2005).
Human Metabolome Database Accession No. HMDB00564, Showing Metabocard for PC(16:0/16:0), http://www.hmdb.ca/metabolities/HMDB00564, 16 pages, (Nov. 16, 2005).
Human Metabolome Database Accession No. HMDB00797, Showing Metabocard for SAICAR, http://www.hmdb.calmetabolities/HMDB00797, 6 pages, (Nov. 16, 2005).
Human Metabolome Database Accession No. HMDB00894, Showing Metabocard for Vinylacetylglycine, http://www.hmdb.ca/metabolities/HMDB00894, 9 pages, (Nov. 16, 2005).
Human Metabolome Database Accession No. HMDB00991, Showing Metabocard for DL-2-Aminoctanoic Acid, http://www.hmdb.ca/metabolities/HMDB00991, 5 pages, (Nov. 16, 2005).
Human Metabolome Database Accession No. HMDB04827, Showing Metabocard for Proline Betaine, http://www.hmdb.ca/metabolities/HMDB04827, 5 pages, (Aug. 24, 2006).
Human Metabolome Database Accession No. HMDB06607, Showing Metabocard for 3'-Sialyllactosamine, http://www.hmdb.ca/metabolities/HMDB06607, 8 pages, (May 25, 2007).
Human Metabolome Database Accession No. HMDB06744, Showing Metabocard for 3-Carboxy-1-hydroxypropylthiamine Diphosphate, http://www.hmdb.ca/metabolities/HMDB06744, 8 pages, (Jun. 11, 2008).
Human Metabolome Database Accession No. HMDB12153, Showing Metabocard for 3,4-Dihydroxybenzylamine, http://www.hmdb.ca/metabolities/HMDB12153, 7 pages, (Apr. 6, 2009).
International Search Report, PCT/US15/25247, 2 pages, (Apr. 30, 2015).

Jaeken, J. and Van Den Berghe, G., An Infantile Autistic Syndrome Characterised by the Presence of Succinylpurines in Body Fluids, The Lancet, 2(8411):1058-1061, (1984).
James, S. J., et al., Metabolic Biomarkers of Increased Oxidative Stress and Impaired Methylation Capacity in Children with Autism, The American Journal of Clinical Nutrition, 80:6:1611-1617, (2004).
Jauniaux, E. et al., Free amino acids in human fetal liver and fluids at 12-17 weeks of gestation, Human Reproduction, 14:6:1638-1641, (1999).
Jiang, Q. et al., γ-Tocopherol, the major form of vitamin E in the US diet, deserves more attention, American Journal of Clinical Nutrition 74, 714-722 (2001).
Jones, R. M. and Lord, C., Diagnosing autism in neurobiological research studies, Behavioural Brain Research, 251:113-124 (2013).
Kałużna-Czaplińska, J. et al, Identification of organic acids as potential biomarkers in the urine of autistic children using gas chromatography/mass spectrometry, J. Chromatogr. B., 7 pgs., (2014).
Kałużna-Czaplińska, J. et al., Determination of tryptophan in urine of autistic and healthy children by gas chromatography/mass spectrometry, Med. Sci. Monit., 16 10):CR488-492, (2010).
Kale, A. et al., Elevated amniotic fluid amino acid levels in fetuses with gastroschisis, Brazilian Journal of Medical and Biological Research, 39:1021-1025, (2006).
Kuwabara, H. et al., Altered Metabolites in the Plasma of Autism Spectrum Disorder: A Capillary Electrophoresis Time-of-Flight Mass Spectroscopy Study, PLOS One, 8:9:e73814, (2013).
Lord, R. S. et al., Clinical Applications of Urinary Organic Acids, Part 2, Dysbiosis Markers, Alternative Medicine Review, 13:4:292-306, (2008).
Minderaa, R. B. et al., Urinary 5-Hydroxyindoleacetic Acid and Whole Blood Serotonin and Tryptophan in Autistic and Normal Subjects, Biol Psychiatry, 22:933-940, (1987).
Ming, X. et al., Metabolic Perturbance in Autism Spectrum Disorders: A Metabolomics Study, American Chemical Society, J. Proteome Res., 11:5856-5862, (2012).
Mochel, F. et al., Elevated CSF N-acetylaspartylglutamate in Patients with Free Sialic Acid Storage Diseases, Neurology, 74(4):302-305, (2010).
Mulder, E. J. et al., Urinary Excretion of 5-Hydroxyindoleacetic Acid, Serotonin and 6-Sulphatoxymelatonin in Normoserotonemic and Hyperserotonoemic Autistic Individuals, Neuropsychobiology, 61:27:27-32, (2010).
Parracho, H. et al., Differences between the gut microflora of children with autistic spectrum disorders and that of healthy children, Journal of Medical Microbiology, 54:987-991, (2005).
Quinones, M and Kaddurah-Daouk, R., Metabolomics Tools for identifying biomarkers for neuropsychiatric diseases, Neurobiology of Disease, 35(2):165-176, (2009).
Rosémeyer, R., A review of the serotonin transporter and prenatal cortisol in the development of autism spectrum disorders, Molecular Autism, 4:37:1-16, (2013).
Schain, R. J. And Freedman, D. X., Studies on 5-hydroxyindole metabolism in autistic and other mentally retarded children, The Journal of Pediatrics 58:3:315-320, (1961).
Shimmura, C. et al., Alteration of Plasma Glutamate and Glutamine Levels in Children with High-Functioning Autism, PLoS One, 6:10:e25340, (2011).
Shinohe, A. et al., Increased serum levels of glutamate in adult patients with autism, Progress in Neuro-Psychopharmacology & Biological Psychiatry 30:1472-1477, (2006).
Singh, V. et al., Antibodies to Myelin Basic Protein in Children with Autistic Behavior, Brain, Behavior, and Immunity 7:97-103, (1993).
Spilioti, M. et al., Evidence for treatable inborn errors of metabolism in a cohort of 187 Greek patients with autism spectrum disorder (ASD), Frontiers in Human Neuroscience, 7:858:1-7, (2013).
Tanaka, K. and Hine, D. G., Compilation of Gas Chromatographic Retention Indices of 163 Metabolically Important Organic Acids, and Their Use in Detection of Patients with Organic Acidurias, J. Chromatogr., 239:301-322 (1982).
Veenstra-Vanderweele, J. et al., Autism gene variant causes hyperserotonemia, serotonin receptor hypersensitivity, social impairment and repetitive behavior, PNAS, 109:15:5469-5474, (2012).

(56) References Cited

OTHER PUBLICATIONS

Ventola, P. et al., Differentiating Between Autism Spectrum Disorders and Other Developmental Disabilities in Children Who Failed a Screening Instrument for ASD, Journal of Autism and Developmental Disorders 37:425-436 (2007).

West, P. R. et al., Metabolomics as a Tool for Discovery of Biomarkers of Autism Spectrum Disorder in the Blood Plasma of Children, Plos One, 9:11:e112445:1-13, (2014).

Whiteley, P. et al., Spot urinary creatinine excretion in pervasive developmental disorders, Pediatrics International 48:292-297, (2006).

Written Opinion, International Application No. PCT/US15/25247, 3 pages (Apr. 30, 2015).

Yap, I. K. S. et al., Urinary Metabolic Phenotyping Differentiates Children with Autism from Their Unaffected Siblings and Age-Matched Controls, J. Proteome Res., 9(6):2996-3004, (2010).

Young, S. N. et al., Tryptophan, 5-hydroxyindoleacetic acid and indoleacetic acid in human cerebrospinal fluid: interrelationships and the influence of age, sex, epilepsy and anticonvulsant drugs, Journal of Neurology, Neurosurgery, and Psychiatry, 43:438-445, (1980).

Zheng, Z. et al., The Footprints of Gut Microbial—Mammalian Co-Metabolism, American Chemical Society, J. Proteome Res., 10:5512-5522, (2011).

Zwaigenbaum, L. et al., Early identification of autism spectrum disorders, Behavioural Brain Research, 251:133-146 (2013).

Zweig, M. H. & Campbell, G., Receiver-Operating Characteristic (ROC) Plots: A Fundamental Evaluation Tool in Clinical Medicine, Clinical Chemistry 39:561-577 (1993).

\* cited by examiner

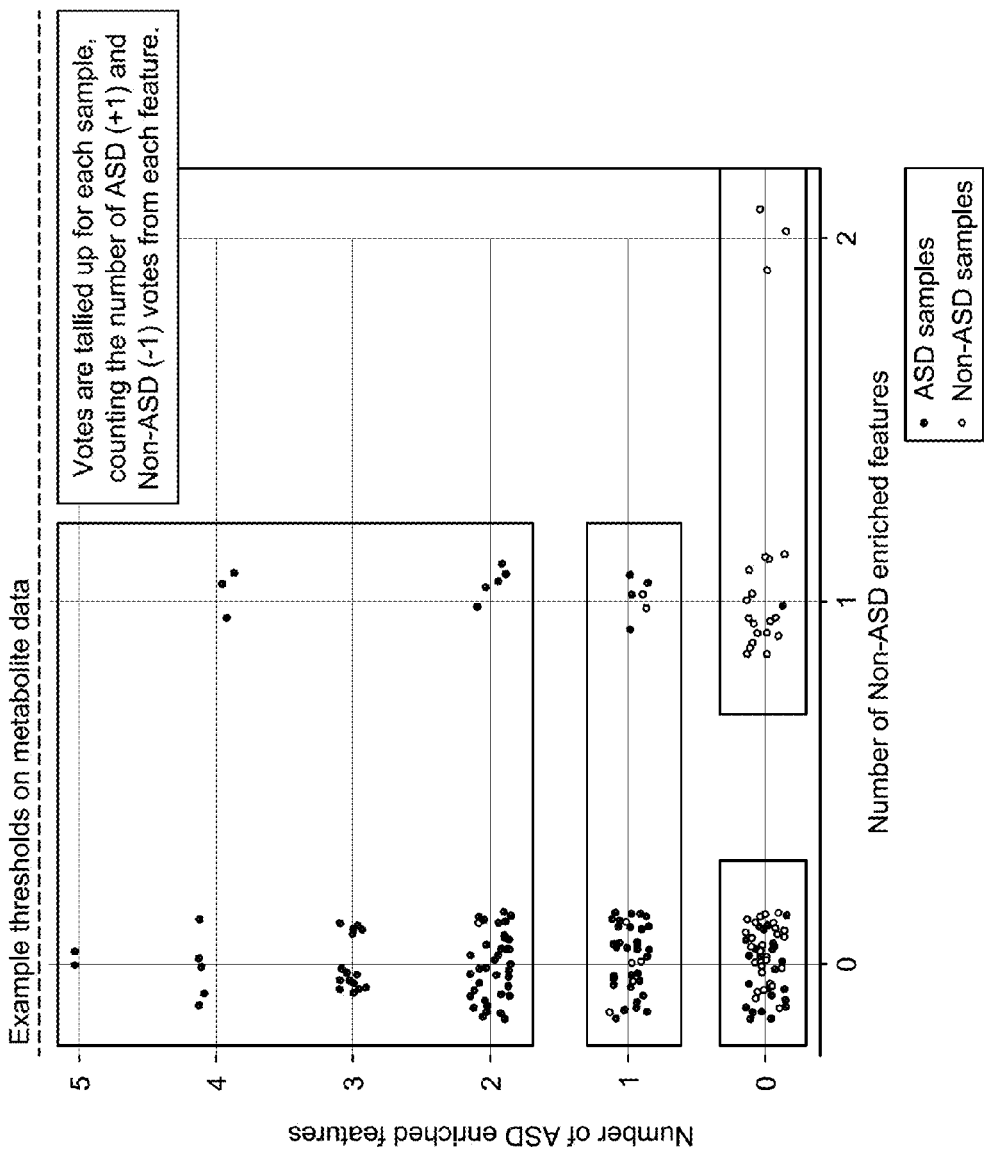

METHODS AND SYSTEMS FOR DETERMINING AUTISM SPECTRUM DISORDER RISK

CROSS REFERENCE TO RELATED APPLICATIONS

The present application is a continuation-in-part application of U.S. patent application Ser. No. 14/493,141, filed on Sep. 22, 2014, which claims the benefit of U.S. Provisional Patent Application No. 61/978,773 filed Apr. 11, 2014, and U.S. Provisional Patent Application No. 62/002,169 filed May 22, 2014; the contents of each of which are incorporated by reference herein in their entirety.

FIELD OF THE INVENTION

The present invention relates generally to the prediction of risk for Autism Spectrum Disorder (ASD) and other disorders.

BACKGROUND

Autism Spectrum Disorders (ASD) are pervasive developmental disorders characterized by reciprocal social interaction deficits, language difficulties, and repetitive behaviors and restrictive interests that often manifest during the first 3 years of life. The etiology of ASD is poorly understood but is thought to be multifactorial, with both genetic and environmental factors contributing to disease development.

Data show that although the average age at which parents begin to suspect an ASD in their child is 20 months, the median age of diagnosis is not until 54 months. An important challenge from a clinical perspective is determining, as early as possible, whether a child has ASD and requires specialist referral for an autism treatment plan.

SUMMARY

Diagnosis of ASD is typically made by developmental pediatricians and other specialists only after careful assessment of children using criteria spelled out in the Diagnostic and Statistical Manual of Mental Disorders. Reliable diagnosis often entails intense assessment of subjects by multiple experts including developmental pediatricians, neurologists, psychiatrists, psychologists, speech and hearing specialists and occupational therapists. Moreover, the median age of diagnosis of ASD is 54 months despite the fact that the average age at which parents suspect ASD is as early as 20 months. The CDC (Centers for Disease Control) has observed that only 18% of children who end up with an ASD diagnosis are identified by age 36 months. Regrettably, young children suffering from undiagnosed ASD miss an opportunity to benefit from early therapeutic intervention during an important window of childhood development. A medical diagnostic test to reliably determine ASD risk is needed, particularly to identify younger children earlier when therapeutic intervention is likely to be more effective.

Embodiments of the present invention stem from the discovery that analysis of distribution curves of measured analytes, such as metabolites, within and across populations provides information that can be utilized to build or improve a classifier for prediction of risk for a condition or disorder, such as ASD. In particular, analysis of population distribution curves of metabolite levels in blood facilitates prediction of the risk of autism spectrum disorder (ASD) in a subject. For example, analysis of population distribution curves of metabolite levels in blood can be used to differentiate between autism spectrum disorder (ASD) and non-ASD developmental disorders in a subject such as developmental delay (DD) not due to autism spectrum disorder.

The statistical analysis of a biomarker differentiating two groups usually assumes that the two populations differ in their mean biomarker levels and that variation around this mean is due to experimental and/or population variation best characterized by a Gaussian distribution. Contrary to this baseline model, it is observed herein that for some analytes, but not for others, the distribution in ASD, or sometimes in DD, is best characterized as itself composed of multiple sub-distributions—one sub-distribution that is essentially undifferentiated from the other health state (e.g., where ASD and DD distributions are undifferentiated), and another sub-distribution that is far removed from the mean in a minority of subjects, e.g., a "tail" of the combined distribution for that population. This insight leads to a significantly different analytic framework from the baseline; it is found that for certain analytes, better results are achieved by defining a threshold based on a top or bottom portion of the population distribution, e.g., by establishing a ranking that does not require an underlying Gaussian distribution model.

Thus, a metabolite is described herein as exhibiting a "tail enrichment" or "tail" effect, where there is an enrichment of samples from a particular population (e.g., either ASD or DD) at a distal portion of the distribution curve of metabolite levels for that metabolite. Information from assessment of the presence, absence, and/or direction (upper or lower) of a tail effect in a metabolite distribution curve can be utilized to predict risk of ASD. It has been discovered that for particular metabolites, metabolite levels corresponding to a top or bottom portion (e.g., decile) of the distribution curve, i.e., within a 'tail' of the distribution curve (whether in a 'right tail' or 'left tail'), are highly informative of the presence or absence of ASD.

Furthermore, it is found that risk prediction improves as multiple metabolites are incorporated having a low degree of overlapping, mutual information. For example, for assessment of ASD, there are particular groups of metabolites that provide complementary diagnostic/risk assessment information. That is, ASD-positive individuals who are identifiable by analysis of the level of a first metabolite (e.g., individuals within an identified tail of the first metabolite) are not the same as the ASD-positive individuals who are identifiable by analysis of a second metabolite (or there may be a low, non-zero degree of overlap). Without wishing to be bound to a particular theory, this discovery may be reflective of the multi-faceted nature of ASD, itself.

Thus, in certain embodiments, the risk assessment method includes identifying whether a subject falls within any of a multiplicity of identified metabolite tails involving a plurality of metabolites, e.g., where the predictors of the different metabolite tails are at least partially disjoint, e.g., they have low mutual information, such that risk prediction improves as multiple metabolites are incorporated with low mutual information. The classifier has a predetermined level of predictability, e.g., in the form of AUC—i.e., area under a ROC curve for the classifier that plots false positive rate (1-specificity) against true positive rate (sensitivity)—where AUC increases upon addition of metabolites to the classifier that exhibit tail effects with low mutual information.

In some embodiments, the invention stems from the discovery that certain threshold values of metabolite levels in blood can be used to facilitate predicting risk of autism spectrum disorder (ASD) in a subject. In certain aspects, these threshold values of metabolites deduced from assessment of the presence, absence, and/or direction (upper or lower) of a tail effect in a metabolite distribution curve are utilized to predict risk of ASD. In certain aspects, these threshold values could be at either the upper or lower end of the distribution of metabolite levels in a population. It has been discovered that, for particular metabolites, levels of the metabolite above an upper threshold value and/or below a lower threshold value are highly informative of the presence or absence of ASD.

In some embodiments, levels of these metabolites are useful in distinguishing ASD from other forms of developmental delay (e.g., developmental delay (DD) not due to autism spectrum disorder).

In one aspect, the invention is directed to a method of differentiating between autism spectrum disorder (ASD) and non-ASD developmental delay (DD) in a subject, the method comprising: (i) measuring the level of a first metabolite of a plurality of metabolites from a sample obtained from the subject, the population distributions of the first metabolite being previously characterized in a first population of subjects with ASD and in a second population of subjects with non-ASD developmental delay (DD), wherein the first metabolite is predetermined to exhibit an ASD tail effect and/or a DD tail effect, each tail effect comprising an associated right tail or left tail enriched in members of the corresponding (ASD or DD) population, and where the first metabolite exhibits an ASD tail effect with a right tail, the level of the first metabolite in the sample is within the ASD tail when the level of the first metabolite in the sample is greater than a predetermined upper (minimum) threshold defining the right tail enriched in first (ASD) population members, and, where the first metabolite exhibits an ASD tail effect with a left tail, the level of the first metabolite in the sample is within the ASD tail when the level of the first metabolite in the sample is less than a predetermined lower (maximum) threshold defining the left tail enriched in first (ASD) population members, and where the first metabolite exhibits a DD tail effect with a right tail, the level of the first metabolite in the sample is within the DD tail when the level of the first metabolite in the sample is greater than a predetermined upper (minimum) threshold defining the right tail enriched in second (DD) population members, and, where the first metabolite exhibits a DD tail effect with a left tail, the level of the first metabolite in the sample is within the DD tail when the level of the first metabolite in the sample is less than a predetermined lower (maximum) threshold defining the left tail enriched in second (DD) population members; (ii) measuring the level of at least one additional metabolite of the plurality of metabolites from the sample, the population distribution of each of the at least one additional metabolite being previously characterized in the first population and in the second population and predetermined to exhibit at least one of an ASD tail effect and a DD tail effect, and, for each of the at least one additional metabolite, identifying whether the level of said metabolite in the sample is within the corresponding ASD tail and/or DD tail, according to step (i); and (iii) determining with a predetermined level of predictability that (a) the subject has ASD and not DD or (b) the subject has DD and not ASD, based on the identified ASD tails and/or the identified DD tails within which the sample lies for the metabolites analyzed in step (i) and step (ii).

In certain embodiments, the first metabolite is predetermined to exhibit an ASD tail effect with an associated upper (minimum) or lower (maximum) threshold, said threshold predetermined such that the odds that a sample of unknown classification (a previously uncharacterized sample) meeting this criteria is ASD as opposed to DD are no less than 1.6:1 with $p \leq 0.3$. In certain embodiments, the odds are no less than 2:1, or no less than 2.5:1, or no less than 2.75:1, or no less than 3:1, or no less than 3.25:1, or no less than 3.5:1, or no less than 3.75:1, or no less than 4:1. In any of the preceding, p-value (statistical significance value) satisfies $p \leq 0.3$, or $p \leq 0.25$, or $p \leq 0.2$, or $p \leq 0.15$, or $p \leq 0.1$, or $p \leq 0.05$.

In certain embodiments, the first metabolite is predetermined to exhibit a DD tail effect with an associated upper (minimum) or lower (maximum) threshold, said threshold predetermined such that the odds that a sample of unknown classification (a previously uncharacterized sample) meeting this criteria is DD as opposed to ASD are no less than 1.6:1 with $p \leq 0.3$. In certain embodiments, the odds are no less than 2:1, or no less than 2.5:1, or no less than 2.75:1, or no less than 3:1, or no less than 3.25:1, or no less than 3.5:1, or no less than 3.75:1, or no less than 4:1. In any of the preceding, p-value (statistical significance value) satisfies $p \leq 0.3$, or $p \leq 0.25$, or $p \leq 0.2$, or $p \leq 0.15$, or $p \leq 0.1$, or $p \leq 0.05$.

In certain embodiments, the predetermined level of predictability corresponds to a Receiver Operating Characteristic (ROC) curve that plots false positive rate (1-specificity) against true positive rate (sensitivity) having an AUC (area under curve) of at least 0.70.

In certain embodiments, the predetermined upper (minimum) threshold for one or more of the metabolites is a percentile from $85^{th}$ to $95^{th}$ percentile (e.g., about the $90^{th}$ percentile, or about the $85^{th}$, $86^{th}$, $87^{th}$, $88^{th}$, $89^{th}$, $91^{st}$, $92^{nd}$, $93^{rd}$, $94^{th}$, or $95^{th}$ percentile, rounded to the nearest percentile), and wherein the predetermined lower (maximum) threshold for one or more of the metabolites is a percentile from $10^{th}$ to $20^{th}$ percentile (e.g., about the $15^{th}$ percentile, or about the $10^{th}$, $11^{th}$, $12^{th}$, $13^{th}$, $14^{th}$, $16^{th}$, $17^{th}$, $18^{th}$, $19^{th}$, or $20^{th}$ percentile, rounded to the nearest percentile).

In certain embodiments, the plurality of metabolites comprises at least two metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxychlorothalonil, octenoylcarnitine, and 3-hydroxyhippurate.

In certain embodiments, the plurality of metabolites comprises at least two metabolites selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl)propionate, 3-indoxyl sulfate, pantothenate (Vitamin B5), and hydroxy-chlorothalonil.

In certain embodiments, the plurality of metabolites comprises at least three metabolites selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl)propionate, 3-indoxyl sulfate, pantothenate (Vitamin B5), and hydroxy-chlorothalonil.

In certain embodiments, the plurality of metabolites comprises at least one pair of metabolites selected from the pairs listed in Table 6.

In certain embodiments, the plurality of metabolites comprises at least one triplet of metabolites selected from the triplets listed in Table 7.

In certain embodiments, the plurality of metabolites comprises at least one pair of metabolites that, combined together as a set of two metabolites, provides an AUC of at least 0.62 (e.g., at least about 0.63, 0.64, or 0.65), where AUC is area under a ROC curve that plots false positive rate (1-specificity)

against true positive rate (sensitivity) for a classifier based only on the set of two metabolites.

In certain embodiments, the plurality of metabolites comprises at least one triplet of metabolites that, combined together as a set of three metabolites, provide an AUC of at least 0.66 (e.g., at least about 0.67 or 0.68), where AUC is area under a ROC curve that plots false positive rate (1-specificity) against true positive rate (sensitivity) for a classifier based only on the set of three metabolites.

In another aspect, the invention is directed to a method of determining autism spectrum disorder (ASD) risk in a subject, the method comprising: (i) analyzing the level of a first metabolite of a plurality of metabolites from a sample obtained from the subject, the population distribution of the first metabolite being previously characterized in a reference population of subjects having known classifications, wherein the first metabolite is predetermined to exhibit an ASD tail effect comprising an associated right tail or left tail enriched in ASD members, and where the first metabolite exhibits an ASD tail effect with a right tail, the level of the first metabolite in the sample is within the ASD tail when the level of the first metabolite in the sample is greater than a predetermined upper (minimum) threshold defining the right tail enriched in ASD population members, and, where the first metabolite exhibits an ASD tail effect with a left tail, the level of the first metabolite in the sample is within the ASD tail when the level of the first metabolite in the sample is less than a predetermined lower (maximum) threshold defining the left tail enriched in ASD population members; (ii) measuring the level of at least one additional metabolite of the plurality of metabolites from the sample, the population distribution of each of the at least one additional metabolite being previously characterized in the reference population and predetermined to exhibit an ASD tail effect, and, for each of the at least one additional metabolite, identifying whether the level of said metabolite in the sample is within the corresponding ASD tail, according to step (i); and (iii) determining with a predetermined level of predictability the risk of the subject having ASD based on the identified ASD tails within which the sample lies for the metabolites analyzed in step (i) and step (ii).

In certain embodiments, the first metabolite is predetermined to exhibit an ASD tail effect with an associated upper (minimum) or lower (maximum) threshold, said threshold predetermined such that the odds that a sample of unknown classification (a previously uncharacterized sample) meeting this criteria is ASD as opposed to DD are no less than 1.6:1 with p≤0.3. In certain embodiments, the odds are no less than 2:1, or no less than 2.5:1, or no less than 2.75:1, or no less than 3:1, or no less than 3.25:1, or no less than 3.5:1, or no less than 3.75:1, or no less than 4:1. In any of the preceding, p-value (statistical significance value) satisfies p≤0.3, or p≤0.25, or p≤0.2, or p≤0.15, or p≤0.1, or p≤0.05.

In certain embodiments, the predetermined level of predictability corresponds to a Receiver Operating Characteristic (ROC) curve that plots false positive rate (1-specificity) against true positive rate (sensitivity) having an AUC (area under curve) of at least 0.70.

In certain embodiments, the plurality of metabolites comprises at least two metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, and 3-hydroxyhippurate.

In another aspect, the invention is directed to a method of determining autism spectrum disorder (ASD) risk in a subject, comprising: (i) analyzing levels of a plurality of metabolites in a sample obtained from the subject, the plurality of metabolites comprising at least two metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, and 3-hydroxyhippurate; and (ii) determining the risk that the subject has ASD based on the quantified levels of the plurality of metabolites.

In certain embodiments, the subject is no greater than about 54 months of age. In certain embodiments, the subject is no greater than about 36 months of age.

In certain embodiments, the plurality of metabolites comprises at least two metabolites selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl)propionate, 3-indoxyl sulfate, pantothenate (Vitamin B5), and hydroxy-chlorothalonil.

In certain embodiments, the plurality of metabolites comprises at least three metabolites selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl)propionate, 3-indoxyl sulfate, pantothenate (Vitamin B5), and hydroxy-chlorothalonil.

In certain embodiments, the plurality of metabolites comprises at least one pair of metabolites selected from the pairs listed in Table 6.

In certain embodiments, the plurality of metabolites comprises at least one triplet of metabolites selected from the triplets listed in Table 7.

In certain embodiments, the plurality of metabolites comprises at least one pair of metabolites that, combined together as a set of two metabolites, provides an AUC of at least 0.62 (e.g., at least about 0.63, 0.64, or 0.65), where AUC is area under a ROC curve that plots false positive rate (1-specificity) against true positive rate (sensitivity) for a classifier based only on the set of two metabolites.

In certain embodiments, the plurality of metabolites comprises at least one triplet of metabolites that, combined together as a set of three metabolites, provide an AUC of at least 0.66 (e.g., at least about 0.67 or 0.68), where AUC is area under a ROC curve that plots false positive rate (1-specificity) against true positive rate (sensitivity) for a classifier based only on the set of three metabolites.

In certain embodiments, the sample is a plasma sample.

In certain embodiments, measuring the levels of metabolites comprises performing mass spectrometry. In certain embodiments, performing mass spectrometry comprises performing one or more members selected from the group consisting of pyrolysis mass spectrometry, Fourier-transform infrared spectrometry, Raman spectrometry, gas chromatography-mass spectroscopy, high pressure liquid chromatography/mass spectroscopy (HPLC/MS), liquid chromatography (LC)-electrospray mass spectroscopy, cap-LC-tandem electrospray mass spectroscopy, and ultrahigh performance liquid chromatography/electrospray ionization tandem mass spectrometry.

In another aspect, the invention is directed to a method of differentiating between autism spectrum disorder (ASD) and non-ASD developmental delay (DD) in a subject, comprising: (i) analyzing levels of a plurality of metabolites in a sample obtained from the subject, the plurality of metabolites comprising at least two metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, and 3-hydroxyhippurate, the levels and/or population distributions of the plurality of metabolites being previously characterized in a reference population; and (ii) determining with a predetermined level of predictability that (a) the subject has ASD and not DD or (b) the subject has DD and not ASD by comparing the levels of the plurality of metabolites from the sample from the subject with predetermined thresholds (e.g., thresholds determined from a reference population of samples having known classifications).

In certain embodiments, the invention provides methods for analyzing metabolites by assigning weights to different metabolites to reflect their respective functions in risk prediction. In some embodiments, the weight assignment can be deduced from the biological functions of the metabolites (e.g., the pathways to which they belong), their clinical utility, or their significance from statistical or epidemiology analyses.

In certain embodiments, the invention provides methods for measuring metabolites using different techniques, including, but not limited to, a chromatography assay, a mass spectrometry assay, a fluorimetry assay, an electrophoresis assay, an immune-affinity assay, and immunochemical assay.

In certain embodiments, the invention provides methods for determining autism spectrum disorder (ASD) risk in a subject, comprising analyzing levels of a plurality of metabolites from a sample from the subject; and determining with a predetermined level of predictability whether the subject has ASD instead of non-ASD developmental disorders based on the quantified levels of the plurality of metabolites.

In certain embodiments, the plurality of metabolites includes at least one metabolite selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, 3-hydroxyhippurate, and combinations thereof.

In certain embodiments, the plurality of metabolites include at least two metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, 3-hydroxyhippurate, and combinations thereof.

In certain embodiments, the plurality of metabolites includes at least 3, at least 4, at least 5, at least 6, at least 7, at least 8, at least 9, or at least 10 metabolites selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, 3-hydroxyhippurate, and combinations thereof.

In certain embodiments, the plurality of metabolites includes additional metabolites. In some embodiments, the plurality of metabolites includes more than 21 metabolites.

In certain embodiments, the invention provides methods for differentiating between autism spectrum disorder (ASD) and non-ASD developmental disorders in a subject, comprising steps of analyzing levels of a plurality of metabolites from a sample from the subject, comparing the levels of the metabolites to their respective population distributions in one reference population, and determining with a predetermined level of predictability whether the subject has ASD instead of non-ASD developmental disorders by comparing the levels of the plurality of metabolites from the sample from the subject to the previously-characterized levels and/or population distributions of the plurality of metabolites in the reference population.

For example, in certain embodiments, the invention provides a diagnostic criterion including at least one metabolite that could predict the risk of ASD in a subject with ROC curve having an AUC of at least 0.60, at least 0.65, at least 0.70, at least 0.75, at least 0.80, at least 0.85 or at least 0.90. AUC is area under a ROC curve that plots false positive rate (1-specificity) against true positive rate (sensitivity) for the classifier.

In certain embodiments, at least one metabolite for analysis is selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, 3-hydroxyhippurate, and combinations thereof.

In certain embodiments, the at least one metabolite for analysis comprises at least two or more members (e.g., 1, 2, 3, 4, 5, 6, 7, 8, 9, 10, 11, 12, 13, 14, 15, 16, 17, 18, 19, 20, 21) selected from the group consisting of 5-hydroxyindoleacetate (5-HIAA), 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, 8-hydroxyoctanoate, gamma-CEHC, hydroxyisovaleroylcarnitine (C5), indoleacetate, isovalerylglycine, lactate, N1-Methyl-2-pyridone-5-carboxamide, p-cresol sulfate, pantothenate (Vitamin B5), phenylacetylglutamine, pipecolate, xanthine, hydroxy-chlorothalonil, octenoylcarnitine, and 3-hydroxyhippurate, in which a non-ASD population distribution curve and an ASD population distribution curve is established for each of the metabolites (e.g., each of said metabolites demonstrating a tail effect).

In certain embodiments, a metabolite for analysis is selected from the group consisting of gamma-CEHC, xanthine, p-cresol sulfate, octenoylcarnitine, phenylacetylglutamine, and combinations thererof.

In certain embodiments, a metabolite for analysis is gamma-CEHC.

In certain embodiments, a metabolite for analysis is xanthine.

In certain embodiments, a metabolite for analysis is p-cresol sulfate.

In certain embodiments, a metabolite for analysis is octenoylcarnitine.

In certain embodiments, a metabolite for analysis is phenylacetylglutamine.

In certain embodiments, a metabolite for analysis is isovalerylglycine.

In certain embodiments, a metabolite for analysis is pipecolate.

In certain embodiments, a metabolite for analysis is indoleacetate.

In certain embodiments, a metabolite for analysis is octenoylcarnitine.

In certain embodiments, a metabolite for analysis is hydroxy-chlorothalonil.

In certain embodiments, the plurality of metabolites comprises at least a first metabolite and a second metabolite that are complementary (e.g., ASD tail samples for the first and second metabolites are substantially non-overlapping such that the predictors provided by the metabolites are partially disjoint and have low mutual information. In certain embodiments, risk prediction improves as multiple metabolites are incorporated with low mutual information.

In certain embodiments, the plurality of metabolites comprises two metabolites, wherein the two metabolites combined together as a set of two metabolites provide an AUC of at least 0.62, 0.63, 0.64, or 0.65.

In certain embodiments, the plurality of metabolites comprises three metabolites, wherein the three metabolites combined together as a set of three metabolites provide an AUC of at least 0.66, 0.67, or 0.68.

In certain embodiments, the invention provides methods of differentiating between autism spectrum disorder (ASD) and a non-ASD developmental disorder in a subject, by analyzing levels of two groups of previously defined metabolites. In certain embodiments, the first group of metabolites represents metabolites that are closely associated with ASD, while the second group of metabolites represents those that are associated with a control condition (e.g., DD). By analyzing both groups of metabolites from a sample from a subject, the risk of the subject having ASD instead of the control condition can be determined by a variety of methods described in the present disclosure. For example, this can be achieved by comparing the aggregated ASD tail effects for the first group of metabolites to the aggregated non-ASD tail effects for the second group of metabolites.

In certain embodiments, the invention provides methods for differentiating between autism spectrum disorder (ASD) and non-ASD developmental delay (DD) in a subject, the method comprising: (i) measuring the levels of a plurality of metabolites in a sample obtained from the subject, wherein the plurality of metabolites comprises at least two metabolites selected from the group consisting of xanthine, gamma-CEHC, hydroxy-chlorothalonil, 5-hydroxyindoleacetate (5-HIAA), indoleacetate, p-cresol sulfate, 1,5-anhydroglucitol (1,5-AG), 3-(3-hydroxyphenyl)propionate, 3-carboxy-4-methyl-5-propyl-2-furanpropanoate (CMPF), 3-indoxyl sulfate, 4-ethylphenyl sulfate, hydroxyisovaleroylcarnitine (C5), isovalerylglycine, lactate, N1-Methyl-2-pyridone-5-carboxamide, pantothenate (Vitamin B5), phenylacetylglutamine, pipecolate, 3-hydroxyhippurate, and combinations thereof; and (ii) calculating the number of metabolites in the sample with a level at or below a predetermined threshold concentration (a) indicative of ASD (ASD left tail effect) as defined in Table 9A, or (b) indicative of DD (DD left tail effect) as defined in Table 9B; and/or (iii) calculating the number of metabolites in the sample with a level at or above a predetermined threshold concentration (a) indicative of ASD (ASD right tail effect) as defined in Table 9A, or (b) indicative of DD (DD right tail effect) as defined in Table 9B; and (iv) determining that the subject has ASD or DD based on the number obtained in steps (ii) and/or (iii).

In certain embodiments, the invention provides methods for determining that a subject has or is at risk for ASD, the method comprising: (i) measuring the levels of a plurality of metabolites in a sample obtained from the subject, wherein the plurality of metabolites comprises at least two metabolites selected from the group consisting of xanthine, gamma-CEHC, hydroxy-chlorothalonil, 5-hydroxyindoleacetate (5-HIAA), indoleacetate, p-cresol sulfate, 1,5-anhydroglucitol (1,5-AG), 3-carboxy-4-methyl-5-propyl-2-furanpropanoate (CMPF), 3-indoxyl sulfate, 4-ethylphenyl sulfate, hydroxyisovaleroylcarnitine (C5), isovalerylglycine, lactate, N1-Methyl-2-pyridone-5-carboxamide, pantothenate (Vitamin B5), phenylacetylglutamine, pipecolate, 3-hydroxyhippurate, and combinations thereof; and (ii) detecting two or more of: (a) xanthine at a level at or above 182.7 ng/ml; (b) hydroxyl-chlorothalonil at a level at or above 20.3 ng/ml; (c) 5-hydroxyindoleacetate at a level at or above 28.5 ng/ml; (d) lactate at a level at or above 686600 ng/ml; (e) pantothenate at a level at or above 63.3 ng/ml; (f) pipecolate at a level at or above 303.6 ng/ml; (g) gamma-CEHC at a level at or below 32.0 ng/ml; (h) indoleacetate at a level at or below 141.4 ng/ml; (i) p-cresol sulfate at a level at or below 182.7 ng/ml; (j) 1,5-anhydroglucitol (1,5-AG) at a level at or below 11910.3 ng/ml; (k) 3-carboxy-4-methyl-5-propyl-2-furanpropanoate (CMPF) at a level at or below 7.98 ng/ml; (l) 3-indoxylsulfate at a level at or below 256.7 ng/ml; (m) 4-ethylphenyl sulfate at a level at or below 3.0 ng/ml; (n) hydroxyisovaleroylcarnitine (C5) at a level at or below 12.9 ng/ml; (o) N1-Methyl-2-pyridone-5-carboxamide at a level at or below 124.82 ng/ml; and (p) phenacetylglutamine at a level at or below 166.4 ng/ml; and (iii) determining that the subject has or is at risk for ASD based on the metabolite levels detected in step (ii).

In certain embodiments, the invention provides methods for determining ASD risk in a subject by measuring both levels of certain metabolites and genetic information from the subject. In some embodiments, the genetic information includes copy number variation (CNVs), and/or Fragile X (FXS) testing.

In additional embodiments, limitations described with respect to certain aspects of the invention can be applied to other aspects of the invention. For example, the limitations of a claim depending from one independent claim may, in some embodiments, be applied to another independent claim.

BRIEF DESCRIPTION OF THE DRAWINGS

FIG. 8B illustrates a plot of ASD and non-ASD tail effects for 180 samples using an exemplary 12-metabolite panel, and an exemplary method of binning the data.

DEFINITIONS

Figure 1:
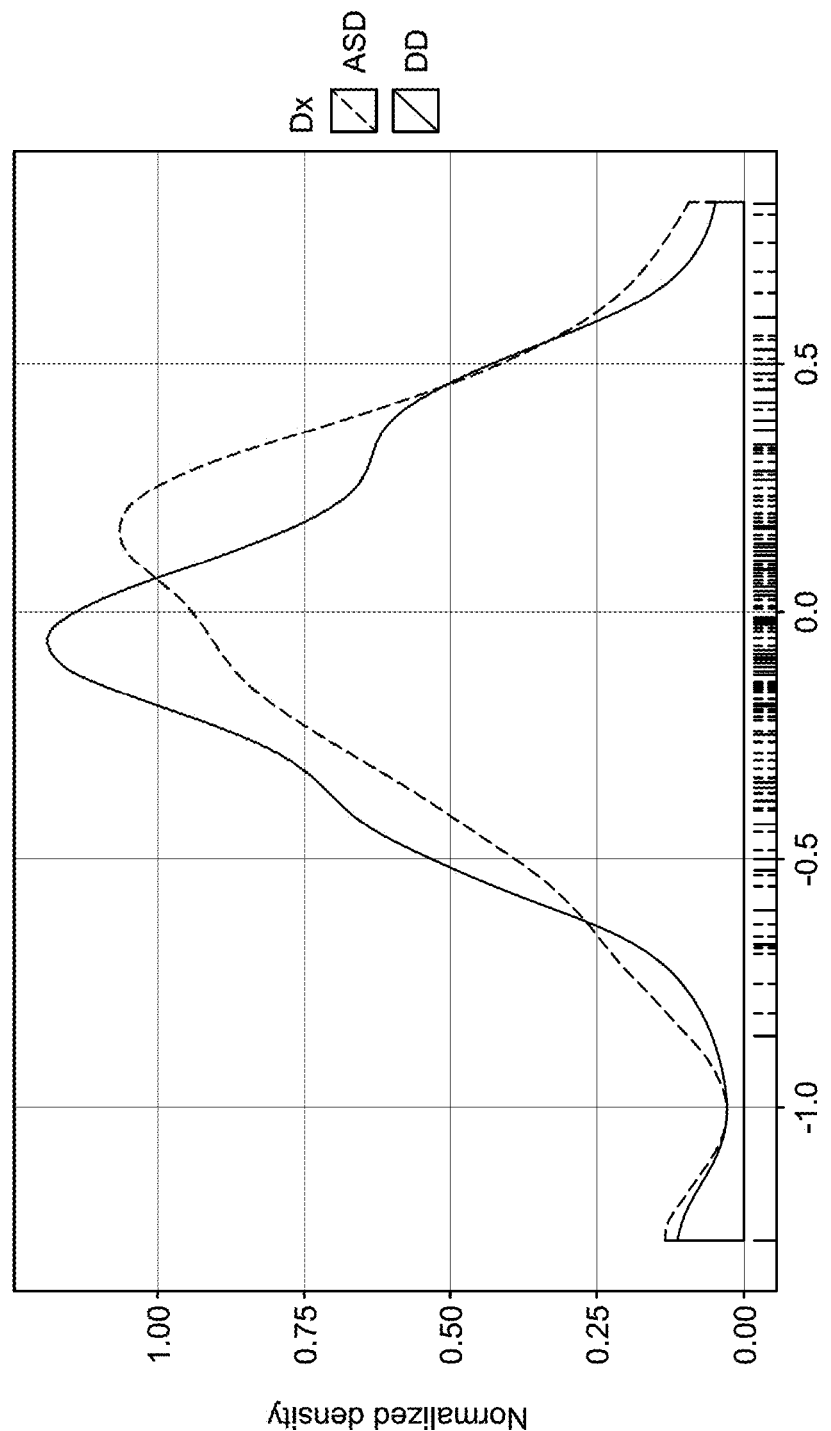
FIG. 1 illustrates the distribution of an exemplary metabolite in two populations (e.g., ASD and DD), and the mean shift of this metabolite between these two populations.

In order for the present invention to be more readily understood, certain terms are first defined below. Additional definitions for the following terms and other terms are set forth throughout the specification.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Agent: The term "agent" as used herein may refer to a compound or entity of any chemical class including, for example, polypeptides, nucleic acids, saccharides, lipids, small molecules, metals, or combinations thereof.

Approximately: As used herein, the term "approximately" and "about" is intended to encompass normal statistical variation as would be understood by those of ordinary skill in the art as appropriate to the relevant context. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Area under curve (AUC): A classifier has an associated ROC curve (Receiver Operating Characteristic curve) that plots false positive rate (1-specificity) against true positive rate (sensitivity). The area under the ROC curve (AUC) is a measure of how well the classifier can distinguish between two diagnostic groups. A perfect classifier has an AUC of 1.0, as compared with a random classifier, which has an AUC of 0.5.

Associated with: Two events or entities are "associated" with one another, as that term is used herein, if the presence, level and/or form of one is correlated with that of the other. For example, a particular entity is considered to be associated with a particular disease, disorder, or condition, if its presence, level and/or form correlates with incidence of and/or susceptibility of the disease, disorder, or condition (e.g., across a relevant population).

Autism spectrum disorder: As used herein, the term "autistic spectrum disorder" is recognized by those of skill in the art to refer to a developmental disorder on the autism "spectrum" characterized by one or more of reciprocal social interaction deficits, language difficulties, repetitive behaviors and restrictive interests. Autism spectrum disorder has been characterized in the DSM-V (May 2013) as a disorder comprising a continuum of symptoms including, for example, communication deficits, such as responding inappropriately in conversations, misreading nonverbal interactions, difficulty building friendships appropriate to age, overdependence on routines, highly sensitive to changes in their environment, and/or intensely focused on inappropriate items. Autism spectrum disorder has additionally been characterized, for example, by DSM-IV-TR, to be inclusive of Autistic Disorder, Asperger's Disorder, Rett's Disorder, Childhood Disintegrative Disorder, and Pervasive Developmental Disorder Not Otherwise Specified (including Atypical Autism). In some embodiments, autism spectrum disorder (ASD) is characterized using standardized testing instruments such as questionnaires and observation schedules. For example, in some embodiments, ASD is characterized by (i) a score meeting the cutoff for autism on Communication plus Social Interaction Total in the Autism Diagnostic Observation Schedule (ADOS) and a score meeting the cutoff value on Social Interaction, Communication, Patterns of Behavior, and Abnormality of Development at ≤36 months in Autism Diagnostic Interview-Revised (ADI-R); and/or (ii) a score meeting the ASD cutoff on Communication and Social Interaction Total in ADOS and a score meeting the cutoff value on Social Interaction, Communication, Patterns of Behavior, and Abnormality of Development at ≤36 months in ADI-R and (ii)(a) a score meeting the cutoff value for Social Interaction and Communication in ADI-R or (ii)(b) a score meeting the cutoff value for Social Interaction or Communication and within 2 points of the cutoff value on Social Interaction or Communication (whichever did not meet the cutoff value) in ADI-R or (ii)(c) a score is within 1 point of cutoff value for Social Interaction and Communication in ADI-R.

Classification: As used herein, "classification" is the process of learning to separate data points into different classes by finding common features between collected data points which are within known classes and then using mathematical methods or other methods to assign data points to one of the different classes. In statistics, classification is the problem of identifying the sub-population to which new observations belong, where the identity of the sub-population is unknown, on the basis of a training set of data containing observations whose sub-population is known. Thus the requirement is that new individual items are placed into groups based on quantitative information on one or more measurements, traits or characteristics, etc., and based on the training set in which previously decided groupings are already established. Classification has many applications. In some cases, it is employed as a data mining procedure, while in others more detailed statistical modeling is undertaken.

Classifier: As used herein, a "classifier" is a method, algorithm, computer program, or system for performing data classification. Examples of widely used classifiers include, but are not limited to, the neural network (multi-layer perceptron), logistic regression, support vector machines, k-nearest neighbors, Gaussian mixture model, Gaussian naive Bayes, decision tree, partial-least-squares determinant analysis (PSL-DA), Fisher's linear discriminant, Logistic regression, Naïve Bayes classifier, Perceptron, support vector machines, quadratic classifiers, Kernet estimation, Boosting, Neural networks, Bayesian networks, Hidden Markov models, and Learning vector quantization.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Determining risk: As used herein, determining risk includes calculating or quantifying a probability that a given subject has, or does not have, a particular condition or disorder. In some embodiments, a positive or negative diagnosis for a disorder or condition, for example, autism spectrum disorder (ASD) or developmental delay (DD) may be made based in whole or in part on a determined risk or risk score (e.g., an odds ratio, or range).

Developmental delay: As used herein, the phrase developmental delay (DD) refers to ongoing major or minor delay in one or more processes of child development, including, for example, physical development, cognitive development, communication development, social or emotional development, or adaptive development that is not due to autism spectrum disorder. Even though an individual with ASD may be considered to be developmentally delayed, the classification of ASD as used herein will be considered to trump that of DD such that the classifications of ASD and DD are mutually exclusive. In other words, unless indicated otherwise, the classification of DD is assumed to mean non-ASD developmental delay. In some embodiments, DD is characterized by non-autism (AU) and non-ASD, yet with (i) score of 69 or lower on a Mullen Scale, score of 69 or lower on Vineland Scale, and score of 14 or lower on SCQ, or (ii) score of 69 or lower on either Mullen or Vineland and within half a standard deviation of cutoff value on the other assessment (score 77 or lower).

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as autism spectrum disorder), state, staging or characteristic of the disease or condition as manifested in the subject, information related to the nature or classification of the disorder, information related to prognosis and/or information useful in selecting an appropriate treatment. Selection of treatment may include the choice of a particular therapeutic agent or other treatment modality such as behavioral therapy, diet modification, etc., a choice about whether to withhold or deliver therapy, a choice relating to dosing regimen (e.g., frequency or level of one or more doses of a particular therapeutic agent or combination of therapeutic agents), etc.

Marker: A marker, as used herein, refers to an agent whose presence or level is associated with, or has a correlation to, a particular disease or condition. Alternatively or additionally, in some embodiments, a presence or level of a particular marker correlates with activity (or activity level) of a particular signaling pathway, for example that may be characteristic of a particular disorder. The marker may or may not play an etiological role in the disease or condition. The statistical significance of the presence or absence of a marker may vary depending upon the particular marker. In some embodiments, detection of a marker is highly specific in that it reflects a high probability that the disorder is of a particular subclass. According to the present invention a useful marker need not distinguish disorders of a particular subclass with 100% accuracy.

Metabolite: As used herein, the term metabolite refers to a substance produced during a bodily chemical or physical process. The term "metabolite" includes any chemical or biochemical product of a metabolic process, such as any compound produced by the processing, cleavage or consumption of a biological molecule. Examples of such molecules include, but are not limited to: acids and related compounds; mono-, di-, and tri-carboxylic acids (saturated, unsaturated aliphatic and cyclic, aryl, alkaryl); aldo-acids, keto-acids; lactone forms; gibbereillins; abscisic acid; alcohols, polyols, derivatives, and related compounds; ethyl alcohol, benzyl alcohol, menthanol; propylene glycol, glycerol, phytol; inositol, furfuryl alcohol, menthol; aldehydes, ketones, quinones, derivatives, and related compounds; acetaldehyde, butyraldehyde, benzaldehyde, acrolein, furfural, glyoxal; acetone, butanone; anthraquinone; carbohydrates; mono-, di-, tri-saccharides; alkaloids, amines, and other bases; pyridines (including nicotinic acid, nicotinamide); pyrimidines (including cytidine, thymine); purines (including guanine, adenine, xanthines/hypoxanthines, kinetin); pyrroles; quinolines (including isoquinolines); morphinans, tropanes, cinchonans; nucieotides, oligonucleotides, derivatives, and related compounds; guanosine, cytosine, adenosine, thymidine, inosine; amino acids, oligopepides, derivatives, and related compounds; esters; phenols and related compounds; heterocyclic compounds and derivatives; pyrroles, tetrapyrroles (corrinoids and porphines/porphyrins, w/w/o metal-ion); flavonoids; indoles; lipids (including fatty acids and triglycerides), derivatives, and related compounds; carotenoids, phytoene; and sterols, isoprenoids including terpenes; and modified version of the above molecules. In some embodiments, a metabolite is the product of metabolism of an endogenous substance. In some embodiments, a metabolite is the product of metabolism of an exogenous substance. In some embodiments, a metabolite is the product of metabolism of an endogenous substance and an exogenous substance. As used herein, the term "metabolome" refers to the chemical profile or fingerprint of the metabolites in a bodily fluid, a cell, a tissue, an organ, or an organism.

Metabolite distribution curve: As used herein, a metabolite distribution curve is a probability distribution curve defined by a function derived from metabolite level plotted against population density (e.g., ASD or DD). In some embodiments, the distribution curve is a standard curve fit of the data. In some embodiments, the distribution curve is a least squares polynomial curve fit. In some embodiments, the distribution curve is asymmetric, or non-Gaussian. In some embodiments, the distribution curve is simply a plot of cases with associated diagnostic category vs. metabolite values (e.g., a 'rug plot'), where there is no curve fit.

Mutual information: As used herein, mutual information refers to a measure of the mutual dependence of two variables (i.e., a degree to which knowing one variable reduces uncertainty about another variable.) High mutual information indicates a large reduction in uncertainty; low mutual information indicates a small reduction; and zero mutual information between two random variables means the variables are independent.

Non-autism spectrum disorder (non-ASD): As used herein, non-autism spectrum disorder (non-ASD) refers to a classification that is not of a child or adult with an autistic spectrum disorder. In some embodiments, "non-ASD" is normally developing subjects. In some embodiments, a non-ASD population consists of or comprises subjects with developmental delay (DD). In some embodiments, "non-ASD" consists of or comprises both DD and normally developing subjects.

Patient: As used herein, the term "patient" or "subject" refers to any organism to which a test or composition is or may be administered, e.g., for experimental, diagnostic, prophylactic, and/or therapeutic purposes. In some embodiments, a patient is suffering from or susceptible to one or more disorders or conditions. In some embodiments, a patient displays one or more symptoms of a disorder or condition. In some embodiments, a patient is suspected to have one or more disorders or conditions.

Predictability: As used herein, predictability refers to the degree to which a correct prediction or forecast of a subject's disease status can be made either qualitatively or quantitatively. Perfect predictability implies strict determinism, but lack of predictability does not necessarily imply lack of determinism. Limitations on predictability could be caused by factors such as a lack of information or excessive complexity.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the likelihood that a patient will be cured of a disease, the likelihood that a patient's disease will respond to a particular therapy (wherein response may be defined in any of a variety of ways). Prognostic and predictive information are included within the broad category of diagnostic information.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Regression analysis: As used herein, "regression analysis" includes any techniques for modeling and analyzing several variables, when the focus is on the relationship between a dependent variable and one or more independent variables. More specifically, regression analysis helps understand how the typical value of the dependent variable changes when any one of the independent variables is varied, while the other independent variables are held fixed. Most commonly, regression analysis estimates the conditional expectation of the dependent variable given the independent variables—that is, the average value of the dependent variable when the independent variables are held fixed. Less commonly, the focus is on a quantile, or other location parameter of the conditional distribution of the dependent variable given the independent variables. In all cases, the estimation target is a function of the independent variables called the regression function. In regression analysis, it is also of interest to characterize the variation of the dependent variable around the regression function, which can be described by a probability distribution. Regression analysis is widely used for prediction and forecasting, where its use has substantial overlap with the field of machine learning. Regression analysis is also used to understand which among the independent variables are related to the dependent variable, and to explore the forms of these relationships. In restricted circumstances, regression analysis can be used to infer causal relationships between the independent and dependent variables. A large body of techniques for carrying out regression analysis has been developed. Familiar methods such as linear regression and ordinary least squares regression are parametric, in that the regression function is defined in terms of a finite number of unknown parameters that are estimated from the data. Non-parametric regression refers to techniques that allow the regression function to lie in a specified set of functions, which may be infinite-dimensional.

Risk: As will be understood from context, a "risk" of a disease, disorder or condition is a degree of likelihood that a particular individual will be diagnosed with or will develop the disease, disorder, or condition. In some embodiments, risk is expressed as a percentage. In some embodiments, risk is from 0, 1, 2, 3, 4, 5, 6, 7, 8, 9, or 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments, a reference sample or group of reference samples are from individuals comparable to a particular individual. In some embodiments, relative risk is 0, 1, 2, 3, 4, 5, 6, 7, 8, 9, 10 or more. In some embodiment, relative risk can be expressed as Relative Risk (RR) or Odds Ratio (OR).

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; plasma; serum; blood cells; ascites; tissue or fine needle biopsy samples; cell-containing body fluids; free floating nucleic acids; sputum; saliva; urine; cerebrospinal fluid; peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, such an individual is known to have one or more susceptibility factors that are statistically correlated with increased risk of development of the relevant disease, disorder, and/or condition. In some embodiments, an individual who is susceptible to a disease, disorder, or condition does not display any symptoms of the disease, disorder, or condition. In some embodiments, an individual who is susceptible to a disease, disorder, or condition has not been or not yet been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.)

Tail enrichment and tail effect: As used herein, the terms "tail enrichment" or "tail effect" refer to a classification-enhancing property exhibited by a metabolite (or other analyte) that has a relatively high concentration of samples from a particular population at a distal portion of a distribution curve of metabolite levels. An "upper tail" or "right tail" refers to a distal portion of a distribution curve that is greater than the mean. A "lower tail" or "left tail" refers to a distal portion of a distribution curve that is lower than the mean. In some embodiments, a tail is determined by a predetermined threshold value based on ranking. For example, a sample is designated to be within a tail if its measurement for a certain metabolite is higher than the value corresponding to a percentile from $85^{th}$ to $95^{th}$ (e.g., $90^{th}$) in a population for that metabolite, or is lower than the value corresponding to a percentile from $10^{th}$ to $20^{th}$ (e.g., $15^{th}$) in the population for that metabolite.

Therapeutic agent: As used herein, the phrase "therapeutic agent" refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

Training set: As used herein, a "training set" is a set of data used in various areas of information science to discover potentially predictive relationships. Training sets are used in artificial intelligence, machine learning, genetic programming, intelligent systems, and statistics. In all these fields, a training set has much the same role and is often used in conjunction with a test set.

Test set: As used herein, a "test set" is a set of data used in various areas of information science to assess the strength and utility of a predictive relationship. Test sets are used in artificial intelligence, machine learning, genetic programming, intelligent systems, and statistics. In all these fields, a test set has much the same role.

Treatment: As used herein, the term "treatment" (also "treat" or "treating") refers to any administration of a substance or therapy (e.g., behavioral therapy) that partially or completely alleviates, ameliorates, relieves, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present invention provides methods and systems for determining risk of autism spectrum disorder (ASD) in a subject based on specific analysis of metabolite levels in a sample, e.g., a blood sample or a plasma sample. Various aspects of the invention are described in detail in the following sections. The use of sections and headers is not meant to limit the invention. Each section can apply to any aspect of the invention. In this application, the use of "or" means "and/or" unless otherwise apparent.

Autism Spectrum Disorder

Criteria for a clinical diagnosis of autism spectrum disorder (ASD) has been set forth in the Diagnostics and Statistical Manual of Mental Disorders, version 5 (DSM-V, published in May 2013).

ASD has additionally been characterized, for example, by DSM-IV-TR, to be inclusive of Autistic Disorder, Asperger's Disorder, Rett's Disorder, Childhood Disintegrative Disorder, and Pervasive Developmental Disorder Not Otherwise Specified (including Atypical Autism).

In some embodiments, ASD is characterized by (i) a score meeting the cutoff for autism on Communication plus Social Interaction Total in ADOS and a score meeting the cutoff value on Social Interaction, Communication, Patterns of Behavior, and Abnormality of Development at ≤36 months in ADI-R; and/or (ii) a score meeting the ASD cutoff on Communication and Social Interaction Total in ADOS and a score meeting the cutoff value on Social Interaction, Communication, Patterns of Behavior, and Abnormality of Development at ≤36 months in ADI-R and (ii)(a) a score meeting the cutoff value for Social Interaction and Communication in ADI-R or (ii)(b) a score meeting the cutoff value for Social Interaction or Communication and within 2 points of the cutoff value on Social Interaction or Communication (whichever did not meet the cutoff value) in ADI-R or (ii)(c) a score is within 1 point of cutoff value for Social Interaction and Communication in ADI-R.

Developmental Delay

Development delay is a major or minor delay in one or more processes of child development, including, for example, physical development, cognitive development, communication development, social or emotional development, or adaptive development that is not due to ASD. In some embodiments, DD is characterized by non-Autism (AU) and non-ASD with (i) score of 69 or lower on a Mullen Scale, score of 69 or lower on Vineland Scale, and score of 14 or lower on SCQ, or (ii) score of 69 or lower on either Mullen or Vineland and within half a standard deviation of cutoff value on the other assessment (score 77 or lower). Even though an individual with ASD may be considered to be developmentally delayed, the classification of ASD as used herein will be considered to trump that of DD such that the classifications of ASD and DD are mutually exclusive.

Risk Assessment of ASD

Children who present with symptoms of impaired language, behavioral, or social development are often seen by clinicians, most commonly in a primary care setting, who are unable to determine whether that child has ASD, or some other condition, disorder, or classification (e.g., DD). It is difficult to diagnose children, particularly at an age prior to extensive language development, and many primary care physicians do not have the ability or resources to make a differential diagnosis of their patients. For example, ASD may not be easily distinguished from other developmental disorders, conditions, or classifications, such as DD.

It is useful to assess risk of ASD in a subject (including probability of non-ASD and DD), and to differentiate ASD from DD. Risk assessment of ASD provides opportunities for early intervention and treatment. For example, a non-specialist physician may use ASD risk assessment to initiate a referral to a specialist. A specialist may use ASD risk assessment to prioritize further evaluation of patients. Assessment of ASD risk may also be used to establish a provisional diagnosis, prior to a final diagnosis, during which time facilitative services can be provided to a high risk child and his or her family.

Described herein are methods for determining risk of ASD in a subject. In some embodiments, determining ASD risk includes determining that the subject has a greater than about a 50% chance of having ASD. In some embodiments, determining ASD risk includes determining the subject has a greater than about 60%, 65%, 70%, 74%, 80%, 85%, 90%, 95%, or 98% chance of having ASD. In some embodiments determining ASD risk includes determining that a subject has ASD. In some embodiments, determining ASD risk includes determining that a subject does not have ASD (i.e., non-ASD).

In some embodiments, the invention provides methods for differentiating ASD from a non-ASD classification (e.g., DD) in a subject. In some embodiments, differentiating ASD from the non-ASD classification/condition includes determining the subject has a greater than about 60%, 65%, 70%, 74%, 80%, 85%, 90%, 95%, or 98% chance of having ASD instead of the non-ASD classification (i.e., chance of having ASD and not having the non-ASD classification). In some embodiments, the non-ASD classification is DD. In some embodiments, the non-ASD classification is "normal".

In some embodiments, the invention provides methods for determining that a subject does not have either ASD or DD.

Analytical Methods

Described herein are methods for assessing ASD risk, or differentiating ASD from other non-ASD developmental disorders. In some embodiments, the risk assessment is based (at least in part) on measurement and characterization of metabolites in a sample from a subject, e.g., a blood sample. In some embodiments, a plasma sample is derived from the blood sample, and the plasma sample is analyzed.

Metabolites can be detected in a variety of ways, including assays based on chromatography and/or mass spectrometry, fluorimetry, electrophoresis, immune-affinity, hybridization, immunochemistry, ultra-violet spectroscopy (UV), fluorescence analysis, radiochemical analysis, near-infrared spectroscopy (nearIR), nuclear magnetic resonance spectroscopy (NMR), light scattering analysis (LS), and nephelometry.

In some embodiments, the metabolites are analyzed by liquid or gas chromatography or ion mobility (electrophoresis) alone or coupled with mass spectrometry or by mass spectrometry alone. Such methods have been used to identify and quantify biomolecules, such as cellular metabolites. (See, for example, Li et al., 2000; Rowley et al., 2000; and Kuster and Mann, 1998). Mass spectrometry methods may be based on, for example, quadrupole, ion-trap, or time-of-flight mass spectrometry, with single, double, or triple mass-to-charge scanning and/or filtering (MS, MS/MS, or $MS^3$) and preceded by appropriate ionization methods such as electrospray ionization, atmospheric pressure chemical ionization, atmospheric pressure photo ionization, matrix-assisted laser desorption ionization (MALDI), or surface-enhanced laser desorption ionization (SELDI). (See, for example, International Patent Application Publication Nos. WO 2004056456 and WO 2004088309). In some embodiments, the first separation of metabolites from a biological sample can be achieved by using gas or liquid chromatography or ion mobility/electrophoresis. In some embodiments, the ionization for mass spectrometry procedures can be achieved by electrospray ionization, atmospheric pressure chemical ionization, or atmospheric pressure photoionization. In some embodiments, mass spectrometry instruments include quadrupole, ion-trap, or time-of-flight, or Fourier transform instruments.

In some embodiments, metabolites are analyzed on a mass scale via a non-targeted ultrahigh performance liquid or gas chromatography/electrospray or atmospheric pressure chemical ionization tandem mass spectrometry platform optimized for the identification and relative quantification of the small-molecule complement of biological systems. (See, for example, Evans et al., Anal. Chem., 2009, 81, 6656-6667).

In some embodiments, the first separation of metabolites from a biological sample can be achieved by using gas or liquid chromatography or ion mobility/electrophoresis. In some embodiments, the ionization for mass spectrometry procedures can be achieved by electrospray ionization, atmospheric pressure chemical ionization, or atmospheric pressure photoionization. In some embodiments, mass spectrometry instruments include quadrupole, ion-trap, or time-of-flight, or Fourier transform instruments.

In some embodiments, a blood sample containing metabolites of interest is centrifuged to separate plasma from other blood components. In certain embodiments, internal standards are unnecessary. In some embodiments, defined amounts of internal standards are added to (a portion of) the plasma, and then methanol is added to precipitate plasma components such as proteins. Precipitates are separated from supernatant by centrifugation, and the supernatant is harvested. If the concentration of a metabolite of interest is to be increased for more accurate detection, the supernatant is evaporated and the residual dissolved in the appropriate amount of solvent. If the concentration of a metabolite of interest is undesirably high, the supernatant is diluted in the appropriate solvent. An appropriate amount of metabolite-containing sample is loaded onto a liquid-chromatography column equilibrated with the appropriate mixture of mobile phase A and mobile phase B. In the case of reversed-phase liquid chromatography, mobile phase A typically is water with or without a small amount of an additive such as formic acid, and mobile phase B typically is methanol or acetonitrile. An appropriate gradient of mobile phase A and mobile phase B is pumped through the column to achieve separation of metabolites of interest by retention time—or time of elution from the column. As metabolites elute from the column, they are ionized and brought into the gas phase, and the ions are detected and quantified by mass spectrometry. Specificity of detection is achieved by double-filtering for a specific precursor ion and a specific product ion generated from the precursor ion. Absolute quantification may be achieved by normalizing ion counts derived from the metabolite of interest to the ion counts derived from known amounts of an internal standard for a given metabolite and by comparing the normalized ion count to a calibration curve established with known amounts of pure metabolite and internal standards. Internal standards typically are stable-isotope labeled forms of the pure metabolite or pure forms of a structural analogue of the metabolite. Alternatively, relative quantification of a given metabolite in arbitrary units may be calculated by normalization to a selected internal reference value (e.g., the median value for metabolite levels on all samples run from a given group).

In some embodiments, one or more metabolites are measured by immunoassay. Numerous specific immunoassay formats and variations thereof may be utilized for measurement of metabolites. (See, for example, E. Maggio, Enzyme-Immunoassay, (1980) (CRC Press, Inc., Boca Raton, Fla.); see also U.S. Pat. No. 4,727,022 "Methods for Modulating Ligand-Receptor Interactions and their Application"; U.S. Pat. No. 4,659,678 "Immunoassay of Antigens"; U.S. Pat. No. 4,376,110, "Immunometric Assays Using Monoclonal Antibodies,"; U.S. Pat. No. 4,275,149, "Macromolecular Environment Control in Specific Receptor Assays,"; U.S. Pat. No. 4,233,402, "Reagents and Method Employing Channeling," and U.S. Pat. No. 4,230,767, "Heterogenous Specific Binding Assay Employing a Coenzyme as Label."). Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radio labels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein) in accordance with known techniques.

Determination of ASD Risk

In some embodiments, methods of the present invention allow one of skill in the art to identify, diagnose, or otherwise assess subjects based at least in part on measuring metabolite levels in samples obtained from subjects who may not presently exhibit signs or symptoms of ASD and/or other developmental disorders, but who nonetheless may be at risk for having or developing ASD and/or other developmental disorders.

In certain embodiments, levels of metabolites, or other analytes (e.g., proteomic or genomic information) can be measured in a test sample and compared to normal control levels, or to levels in subjects having a developmental disorder, condition, or classification that is not ASD (e.g., non-ASD developmental delay, DD). In some embodiments, the term "normal control level" refers to the level of one or more metabolites, or other analytes, or indices, typically found in subjects not suffering from ASD or not likely to have ASD or other developmental disorder. In some embodiments, a normal control level is a range or an index. In some embodiments, a normal control level is determined from a database of previously tested subjects. A difference in the level of one or more metabolites, or other analytes, compared to a normal control level can indicate that a subject has ASD or is at risk of developing ASD. Conversely, a lack of difference in the level of one or more metabolites compared to a normal control level of one or more metabolites, or other analytes, can indicate that the subject does not have ASD, or is at low risk of developing ASD.

In some embodiments, a reference value is that which has been obtained from a control subject or population whose diagnosis is known (i.e., has been diagnosed with or identified as suffering from ASD, or has not been diagnosed with or identified as suffering from ASD). In some embodiments, a reference value is an index value or baseline value, such as, for example, a "normal control level" as described herein. In some embodiments, a reference sample or index value or baseline value is taken or derived from one or more subjects who have been exposed to treatment for ASD, or may be taken or derived from one or more subjects who are at low risk of developing ASD, or may be taken or derived from subjects who have shown improvements in ASD risk factors as a result of exposure to treatment. In some embodiments, a reference sample or index value or baseline value is taken or derived from one or more subjects who have not been exposed to a treatment for ASD. In some embodiments, samples are collected from subjects who have received initial treatment for ASD and/or subsequent treatment for ASD to monitor the progress of the treatment. In some embodiments, a reference value has been derived from risk prediction algorithms or computed indices from population studies of ASD. In some embodiments, a reference value is from subjects or populations that have a disease or disorder other than ASD, such as another developmental disorder, e.g., non-ASD Developmental Delay (DD).

In some embodiments, differences in the level of metabolites measured by the methods of the present invention comprise increases or decreases in the level of the metabolites as compared to a normal control level, reference value, index value, or baseline value. In some embodiments, increases or decreases in levels of metabolites relative to a reference value from a normal control population, a general population, or from a population with another disease, is indicative of presence of ASD, progression of ASD, exacerbation of ASD or amelioration of ASD or ASD symptoms. In some embodiments, increases or decreases in levels of metabolites relative to a reference value from a normal control population, a general population, or from a population with another disease, is indicative of an increase or decrease in the risk of developing ASD, or complications relating thereto. The increase or decrease can be indicative of the success of one or more treatment regimens for ASD, or can indicate improvements or regression of ASD risk factors. The increase or decrease can be, for example, at least 5%, at least 10%, at least 15%, at least 20%, at least 25%, at least 30%, at least 35%, at least 40%, at least 45%, or at least 50% of a reference value.

In some embodiments, differences in the level of metabolites as described herein are statistically significant differences. "Statistically significant" refers to differences that are greater than what might be expected to happen by chance alone. Statistical significance can be determined by any method known in the art. For example, statistical significance can be determined by p-value. The p-value is a measure of probability that a difference between groups during an experiment happened by chance. For example, a p-value of 0.01 means that there is a 1 in 100 chance the result occurred by chance. The lower the p-value, the more likely it is that a measured difference between groups is not by chance. A difference is considered to be statistically significant if the p-value is at or below 0.05. In some embodiments, a statistically significant p-value is at or below 0.04, 0.03, 0.02, 0.01, 0.005, or 0.001. In some embodiments, a statistically significant p-value is at or below 0.30, 0.25, 0.20, 0.15, or 0.10 (e.g., in the case of identifying whether a single particular metabolite has additive predictive value when used in a classifier including other metabolites). In some embodiments, a p value is determined by t-test. In some embodiments, a p value is obtained by Fisher's test. In some embodiments statistical significance is achieved by analysis of combinations of several metabolites in panels and combined with mathematical algorithms to achieve a statistically significant risk prediction.

A classification test, assay, or method has an associated ROC curve (Receiver Operating Characteristic curve) that plots false positive rate (1-specificity) against true positive rate (sensitivity). The area under the ROC curve (AUC) is a measure of how well the classifier can distinguish between two diagnostic groups. The maximum AUC is 1.0 (a perfect test) and the minimum area is 0.5 (e.g. the area where there is no discrimination of normal versus disease). It is appreciated that as an AUC approaches one, the accuracy of a test increases.

In some embodiments, a high degree of risk prediction accuracy is a test or assay wherein the AUC is at least 0.60. In some embodiments, a high degree of risk prediction accuracy is a test or assay wherein the AUC at least 0.65, at least 0.70, at least 0.75, at least 0.80, at least 0.85, at least 0.90, or at least 0.95.

Predicting ASD Risk by Assessment of Tail Effects

In some embodiments, a mean difference of metabolite levels is assessed among or between populations, e.g., between an ASD population and a DD population, or compared to a normal control population. In some embodiments, metabolites from samples of a given population (i.e., ASD) are assessed for enrichment in a tail of a distribution curve. That is, determining whether a greater proportion of samples from a designated population (e.g., ASD) as compared to a second population (e.g., DD) reside in a tail of the distribution curve (i.e., a "tail effect"). In some embodiments, both mean differences and tail effects are identified and utilized. In some embodiments, a tail is determined by a predetermined threshold value. For example, a sample is designated to be within a tail if its measurement for a certain metabolite is higher than the value corresponding to a $90^{th}$ percentile in a population for that metabolite (right tail, or upper tail), or is lower than the value corresponding to a $15^{th}$ percentile (left tail, or lower tail). In some embodiments, the threshold for a right (upper) tail for a given metabolite is the value corresponding to the $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, or $99^{th}$ percentile (e.g., where a sample is designated to be within a right tail if its measurement for the given metabolite is higher than the value associated with this percentile). In some embodiments, the threshold for a left (lower) tail for a given metabolite is the value corresponding to the $25^{th}$, $24^{th}$, $23^{th}$ $22^{nd}$ $21^{st}$ $20^{th}$, $19^{th}$, $18^{th}$, $17^{th}$, $16^{th}$, $15^{th}$, $14^{th}$, $13^{th}$, $12^{th}$, $11^{th}$, $10^{th}$, $9^{th}$, $8^{th}$, $7^{th}$, $6^{th}$, $5^{th}$, $4^{th}$, $3^{rd}$, $2^{nd}$, or $1^{st}$ percentile (e.g., where a sample is designated to be within a left tail if its measurement for the given metabolite is lower than the value associated with this percentile). Percentile values shown are inclusive of fractional values.

In some embodiments, a distribution curve is generated from a plot of metabolite levels for one or more populations. In some embodiments, a distribution curve is generated from a single reference population, e.g., a general population. In some embodiments, distribution curves are generated from two populations, e.g., an ASD population and a non-ASD population, such as DD. In some embodiments, distribution curves are generated from three or more populations, e.g., an ASD population, a non-ASD population but with another developmental disorder/condition/classification such as DD, and a healthy (e.g., no developmental disorder) control population. Metabolite distribution curves from each of the populations may be utilized to make more than one risk assessment (e.g. diagnosing ASD, diagnosing DD, differentiating between ASD and DD). The methods for assessment of utilizing tail effects described herein may be applied to more than two populations.

In some embodiments, a plurality of metabolites and their distributions are used for risk assessment. In some embodiments, levels of two or more metabolites are utilized to predict ASD risk. In some embodiments, at least two of the metabolites are selected from the metabolites listed in Table 1. In some embodiments, at least three of the metabolites are selected from the metabolites listed in Table 1. In some embodiments, 4, 5, 6, 7, 8, 9, 10, 11, 12, 13, 14, 15, 16, 17, 18, 19, 20, or 21 metabolites selected from the metabolites listed in Table 1 are used to predict ASD risk.

Further discussion of Table 1 (Tables 1A through 1C) appears in the Examples section below.

TABLE 1A

Exemplary 21-metabolite panel with tail effects predictive of ASD vs. DD
Metabolite 3-(3-hydroxyphenyl)propionate
3-carboxy-4-methyl-5-propyl-2-furanpropanoate (CMPF)
3-indoxyl sulfate
4-ethylphenyl sulfate
5-hydroxyindoleacetate
8-hydroxyoctanoate
gamma-CEHC
hydroxyisovaleroylcarnitine (C5)
indoleacetate
isovalerylglycine
lactate
N1-Methyl-2-pyridone-5-carboxamide
p-cresol sulfate
pantothenate (Vitamin B5)
phenylacetylglutamine
pipecolate
xanthine
hydroxy-chlorothalonil
octenoylcarnitine
3-hydroxyhippurate
1,5-anhydroglucitol (1,5-AG)

TABLE 1B

Exemplary metabolites with tail enrichment predictive of ASD

| Metabolite | Tail Effect | Odds Ratio | Confidence Interval (90%) |
|---|---|---|---|
| 3-carboxy-4-methyl-5-propyl-2-furanpropanoate (CMPF) | Left; p = 0.23 | 1.61 | 1.19-3.65 |
| 3-indoxyl sulfate | Left; p = 0.01 | 3.03 | 1.91-6.12 |
| 4-ethylphenyl sulfate | Left; p = 0.02 | 2.54 | 1.70-5.37 |
| 5-hydroxyindoleacetate | Right; p < 0.01 | 4.91 | 2.22-15.35 |
| 8-hydroxyoctanoate | Left; p = 0.01 | 3.03 | 1.64-5.34 |
| gamma-CEHC | Left; p = 0.01 | 3.03 | 2.08-8.09 |
| hydroxyisovaleroylcarnitine (C5) | Left; p = 0.23 | 1.61 | 1.01-2.73 |
| indoleacetate | Left; p = 0.06 | 2.16 | 1.40-4.17 |
| isovalerylglycine | Left; p = 0.12 | 1.86 | 1.09-3.14 |
| lactate | Right; p = 0.06 | 2.64 | 1.23-4.64 |
| N1-Methyl-2-pyridone-5-carboxamide | Left; p = 0.23 | 1.61 | 0.98-2.73 |
| p-cresol sulfate | Left; p < 0.01 | 3.69 | 1.94-6.68 |
| pantothenate (Vitamin B5) | Right; p = 0.06 | 2.64 | 1.58-7.04 |
| phenylacetylglutamine | Left; p = 0.06 | 2.16 | 1.38-4.03 |

TABLE 1B-continued

Exemplary metabolites with tail enrichment predictive of ASD

| Metabolite | Tail Effect | Odds Ratio | Confidence Interval (90%) |
|---|---|---|---|
| pipecolate | Right; p < 0.01 | 4.91 | 1.79-15.32 |
| xanthine | Right; p = 0.15 | 2.08 | 1.25-4.92 |
| hydroxy-chlorothalonil | Right; p < 0.01 | 4.94 | 2.77-17.71 |
| octenoylcarnitine | Left; p = 0.01 | 3.03 | 1.84-7.31 |
| 1,5-anhydroglucitol (1,5-AG) | Left; p = 0.01 | 3.03 | 1.76-6.44 |

TABLE 1C

Exemplary metabolites with tail enrichment predictive of DD

| Metabolite | Tail Effect | Odds Ratio | Confidence Interval (90%) |
|---|---|---|---|
| 3-(3-hydroxyphenyl)propionate | Left; p < 0.01 | 0.36 | 0.24-0.62 |
| 3-indoxyl sulfate | Right; p = 0.1 | 0.52 | 0.32-0.91 |
| isovalerylglycine | Right; p = 0.01 | 0.33 | 0.19-0.66 |
| p-cresol sulfate | Right; p < 0.01 | 0.28 | 0.17-0.50 |
| phenylacetylglutamine | Right; p < 0.01 | 0.20 | 0.15-0.46 |
| pipecolate | Left; p = 0.30 | 0.69 | 0.40-0.95 |
| xanthine | Left; p = 0.01 | 0.40 | 0.28-0.70 |
| 3-hydroxyhippurate | Left; p = 0.02 | 0.45 | 0.29-0.71 |

In some embodiments, at least two metabolites for analysis are selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl) propionate, 3-indoxyl sulfate, pantothenate (Vitamin B5), hydroxy-chlorothalonil, and combinations thereof.

In some embodiments, at least three metabolites for analysis are selected from the group consisting of phenylacetylglutamine, xanthine, octenoylcarnitine, p-cresol sulfate, isovalerylglycine, gamma-CEHC, indoleacetate, pipecolate, 1,5-anhydroglucitol (1,5-AG), lactate, 3-(3-hydroxyphenyl) propionate, 3-indoxyl sulfate, pantothenate (Vitamin B5), hydroxy-chlorothalonil, and combinations thereof.

In some embodiments, information on the lack of a tail effect for a particular set of metabolites is used for risk assessment. In some embodiments, a lack of tail effects is determined to provide a null result (i.e., no information as opposed to negative information). In some embodiments, a lack of tail effects is determined to be indicative of one classification over another (e.g., more indicative of DD over ASD).

In some embodiments, the distribution curve is asymmetrical, or non-Gaussian. In some embodiments, the distribution curve does not follow a parametric distribution pattern.

In some embodiments, information from mean differences (e.g., mean shifts) is combined with tail effect information for risk assessment. In some embodiments, information from mean differences is used for risk assessment without use of tail effect information.

In some embodiments, analysis of metabolites is combined with other types of information, e.g., genetic information, demographic information, and/or behavior assessment to determine a subject's risk for ASD or other disorders.

In some embodiments, ASD risk-assessment is performed based at least in part on measured amounts of certain metabolites in a biological sample (e.g., blood, plasma, urine, saliva, stool) obtained from a subject, where the certain metabolites are found herein to exhibit "tail effects." It has been found by the inventors that there is not necessarily a statistically significant mean shift between two populations associated with a tail effect. Thus, a tail effect is a specific phenomenon distinct from mean shift.

In certain embodiments, a particular metabolite exhibits a right tail effect indicative of ASD over a non-ASD population (e.g., a DD population) when the metabolite is characterized as follows:
  a non-ASD population distribution curve is established for the metabolite in a non-ASD population (e.g., a DD population) with x-axis indicative of the level of the first metabolite and y-axis indicative of corresponding population;
  an ASD population distribution curve is established for the metabolite in an ASD population with x-axis indicative of the level of the first metabolite and y-axis indicative of corresponding population; and
  the non-ASD population distribution curve and the ASD population distribution curve are characterized in that one or both of (A) and (B) hold(s):
    (A) the ratio of (i) area under the ASD population distribution curve for x>level n of the metabolite to (ii) area under the non-ASD population distribution curve for x>level n of the metabolite is greater than 150% (e.g., >200%, >300%, >500%, >1000%, etc.), thereby providing predictive utility for differentiating between an ASD classification and a non-ASD classification for samples having>level n of the metabolite, and
    (B) where n' is the minimum threshold metabolite level corresponding to the top decile (or, any cutoff from about 5% to about 20%) of combined non-ASD and ASD populations used to create the distribution curves, then for an unknown sample (e.g. a random sample selected from a population having an equal number of ASD and non-ASD members) having a metabolite level of at least n', the odds of the sample being ASD as opposed to non-ASD are no less than 1.6:1 (e.g., no less than 2:1, no less than 3:1, no less than 4:1, no less than 5:1, no less than 6:1, no less than 7:1, no less than 8:1, no less than 9:1, or no less than 10:1) (e.g., where p<0.3, p<0.2, p<0.1, p<0.05, p<0.03, or p<0.01, e.g., statistically significant classification), thereby providing predictive utility for differentiating between an ASD classification and a non-ASD classification for samples having >level n' of the metabolite.

In certain embodiments, a particular metabolite exhibits a left tail effect indicative of ASD over a non-ASD population (e.g., a DD population) when the metabolite is characterized as follows:
  a non-ASD population distribution curve is established for the metabolite in a non-ASD population (e.g., a DD population) with x-axis indicative of the level of the first metabolite and y-axis indicative of corresponding population;
  an ASD population distribution curve is established for the metabolite in an ASD population with x-axis indicative of the level of the first metabolite and y-axis indicative of corresponding population; and
  the non-ASD population distribution curve and the ASD population distribution curve are characterized in that one or both of (A) and (B) hold(s):
    (A) the ratio of (i) area under the ASD population distribution curve for x<level m of the metabolite to (ii) area under the non-ASD population distribution curve for x<level m of the metabolite is greater than 150% (e.g., >200%, >300%, >500%, >1000%, etc.), thereby providing predictive utility for differentiating between an ASD classification and a non-ASD classification for samples having<level m of the metabolite, and (B) where m' is the maximum threshold metabolite level corresponding to the bottom decile (or, any cutoff from about 5% to about 20%) of combined non-ASD and ASD populations used to create the distribution curves, then for an unknown sample (e.g. a random sample selected from a population having an equal number of ASD and non-ASD members) having a metabolite level of less than m', the odds of the sample being ASD as opposed to non-ASD are no less than 1.6:1 (e.g., no less than 2:1, no less than 3:1, no less than 4:1, no less than 5:1, no less than 6:1, no less than 7:1, no less than 8:1, no less than 9:1, or no less than 10:1) (e.g., where $p<0.3$, $p<0.2$, $p<0.1$, $p<0.05$, $p<0.03$, or $p<0.01$, e.g., statistically significant classification), thereby providing predictive utility for differentiating between an ASD classification and a non-ASD classification for samples having <level m' of the metabolite.

In certain embodiments, a particular metabolite exhibits a right tail effect indicative of non-ASD (e.g., DD) over an ASD population when the metabolite is characterized as follows:

a non-ASD population distribution curve is established for the metabolite in a non-ASD population (e.g., a DD population) with x-axis indicative of the level of the first metabolite and y-axis indicative of corresponding population;

an ASD population distribution curve is established for the metabolite in an ASD population with x-axis indicative of the level of the first metabolite and y-axis indicative of corresponding population; and the non-ASD population distribution curve and the ASD population distribution curve are characterized in that one or both of (A) and (B) hold(s):

(A) the ratio of (i) area under the non-ASD population distribution curve for x>level n of the metabolite to (ii) area under the ASD population distribution curve for x>level n of the metabolite is greater than 150% (e.g., >200%, >300%, >500%, >1000%, etc.), thereby providing predictive utility for differentiating between a non-ASD classification and an ASD classification for samples having>level n of the metabolite, and (B) where n' is the minimum threshold metabolite level corresponding to the top decile (or, any cutoff from about 5% to about 20%) of combined non-ASD and ASD populations used to create the distribution curves, then for an unknown sample (e.g. a random sample selected from a population having an equal number of ASD and non-ASD members) having a metabolite level of greater than n', the odds of the sample being non-ASD as opposed to ASD are no less than 1.6:1 (e.g., no less than 2:1, no less than 3:1, no less than 4:1, no less than 5:1, no less than 6:1, no less than 7:1, no less than 8:1, no less than 9:1, or no less than 10:1) (e.g., where $p<0.3$, $p<0.2$, $p<0.1$, $p<0.05$, $p<0.03$, or $p<0.01$, e.g., statistically significant classification), thereby providing predictive utility for differentiating between a non-ASD classification and an ASD classification for samples having>level n' of the metabolite.

In certain embodiments, a particular metabolite exhibits a left tail effect indicative of non-ASD (e.g., DD) over an ASD population when the metabolite is characterized as follows:

a non-ASD population distribution curve is established for the metabolite in a non-ASD population (e.g., a DD population) with x-axis indicative of the level of the first metabolite and y-axis indicative of corresponding population;

an ASD population distribution curve is established for the metabolite in an ASD population with x-axis indicative of the level of the first metabolite and y-axis indicative of corresponding population; and the non-ASD population distribution curve and the ASD population distribution curve are characterized in that one or both of (A) and (B) hold(s):

(A) the ratio of (i) area under the non-ASD population distribution curve for x<level m of the metabolite to (ii) area under the ASD population distribution curve for x<level m of the metabolite is greater than 150% (e.g., >200%, >300%, >500%, >1000%, etc.), thereby providing predictive utility for differentiating between a non-ASD classification and an ASD classification for samples having<level m of the metabolite, and (B) where m' is the maximum threshold metabolite level corresponding to the bottom decile (or, any cutoff from about 5% to about 20%) of combined non-ASD and ASD populations used to create the distribution curves, then for an unknown sample (e.g. a random sample selected from a population having an equal number of ASD and non-ASD members) having a metabolite level of less than m', the odds of the sample being non-ASD as opposed to ASD are no less than 1.6:1 (e.g., no less than 2:1, no less than 3:1, no less than 4:1, no less than 5:1, no less than 6:1, no less than 7:1, no less than 8:1, no less than 9:1, or no less than 10:1) (e.g., where $p<0.3$, $p<0.2$, $p<0.1$, $p<0.05$, $p<0.03$, or $p<0.01$, e.g., statistically significant classification), thereby providing predictive utility for differentiating between a non-ASD classification and an ASD classification for samples having <level m' of the metabolite.

In certain embodiments, a risk assessment is performed using a plurality of metabolites that exhibit tail effects. It has been observed that, for assessment of ASD, there are particular groups of metabolites (e.g., two or more metabolites) which provide complementary diagnostic/risk assessment information. For example, ASD-positive individuals who are identifiable by analysis of the level of a first metabolite (e.g., individuals within an identified tail of the first metabolite) are not the same ASD-positive individuals who are identifiable by analysis of a second metabolite (or there may be a low, non-zero degree of overlap). The tail of a first metabolite is predictive of certain ASD individuals, while the tail of the second metabolite is predictive of other ASD individuals. Without wishing to be bound to a particular theory, this discovery may be reflective of the multi-faceted nature of ASD, itself.

Thus, in certain embodiments, the risk assessment method includes identifying whether a subject falls within any of a multiplicity of identified metabolite tails involving a plurality of metabolites, e.g., where the predictors of the different metabolite tails are at least partially disjoint, e.g., they have low mutual information, such that risk prediction improves as multiple metabolites are incorporated with low mutual information.

EXAMPLES

Subjects

Blood samples were collected from subjects between the ages of 18 and 60 months who were referred to nineteen developmental evaluation centers for evaluation of a possible developmental disorder other than isolated motor problems. Informed consent was obtained for all subjects. Subjects with a prior diagnosis of ASD from a clinic specialized in pediatric development evaluation or who were unable or unwilling to complete study procedures were excluded from the study.

The subjects are those who enrolled in the SynapDx Autism Spectrum Disorder Gene Expression Analysis (STORY) study. The STORY study was performed in accordance with current ICH guidelines on Good Clinical Practice (GCP), and applicable regulatory requirements. GCP is an international ethical and scientific quality standard for designing, conducting, recording, and reporting studies that involve the participation of human subjects. Compliance with this standard provides public assurance that the rights, safety, and wellbeing of study subjects are protected, consistent with the principles that have originated in the Declaration of Helsinki and that the clinical study data are credible.

Results shown in FIGS. 1 to 12 are based on 180 blood samples from males in the STORY study. The sample set included 122 ASD samples, and 58 DD (non-ASD) samples. ASD diagnosis followed DSM-V diagnostic criteria. Additional results are based on a broader set of 299 blood samples from male subjects in the STORY study. The broader sample set included 198 ASD samples and 101 DD samples.

For all tests, approximately 3 mL blood samples were collected in EDTA tubes, and plasma was prepared by centrifuging the tubes. The plasma was then frozen and shipped to a laboratory for analysis. At the laboratory, methanol extraction of the samples was conducted, and the extracts were analyzed by an optimized ultrahigh performance liquid or gas chromatography/tandem mass spectrometry (UHPLC/MS/MS or GC/MS/MS) method (See, for example, Anal. Chem., 2009, 81, 6656-6667).

Data Analysis

Metabolites in blood samples were quantified for both male and female subjects. Samples were assayed for levels of metabolites and quantified as a concentration in arbitrary units normalized to a median concentration for all samples measured on a given day. For example, a unit of greater than 1 refers to a quantity of metabolite that is greater than the median of samples for the day, and a unit of less than 1 refers to a quantity that is less than the median. A cross-validation was then carried out, where samples were randomly divided into non-overlapping training/testing sets on which the unbiased performance of machine learning classifiers was evaluated. Twenty-one metabolites have been identified that are highly informative individually and collectively for predicting ASD, particularly in male subjects.

Example 1

Discerning Metabolite Level Information

This example shows that valuable information for risk assessment for ASD can be discerned from identification and analysis of tail effects in a sample distribution that would otherwise be missed by traditional analyses (e.g., mean shift-based analysis).

Once a metabolite level is determined, there are multiple ways to implement the information for risk assessment, including mean shifts and tail effects. Singularly, mean shifts were found to provide some, but not optimal, predictive information. An exemplary mean shift is shown in FIG. 1. In this figure, the ASD distribution shifts to the right of the non-ASD distribution (DD).

Figure 2:
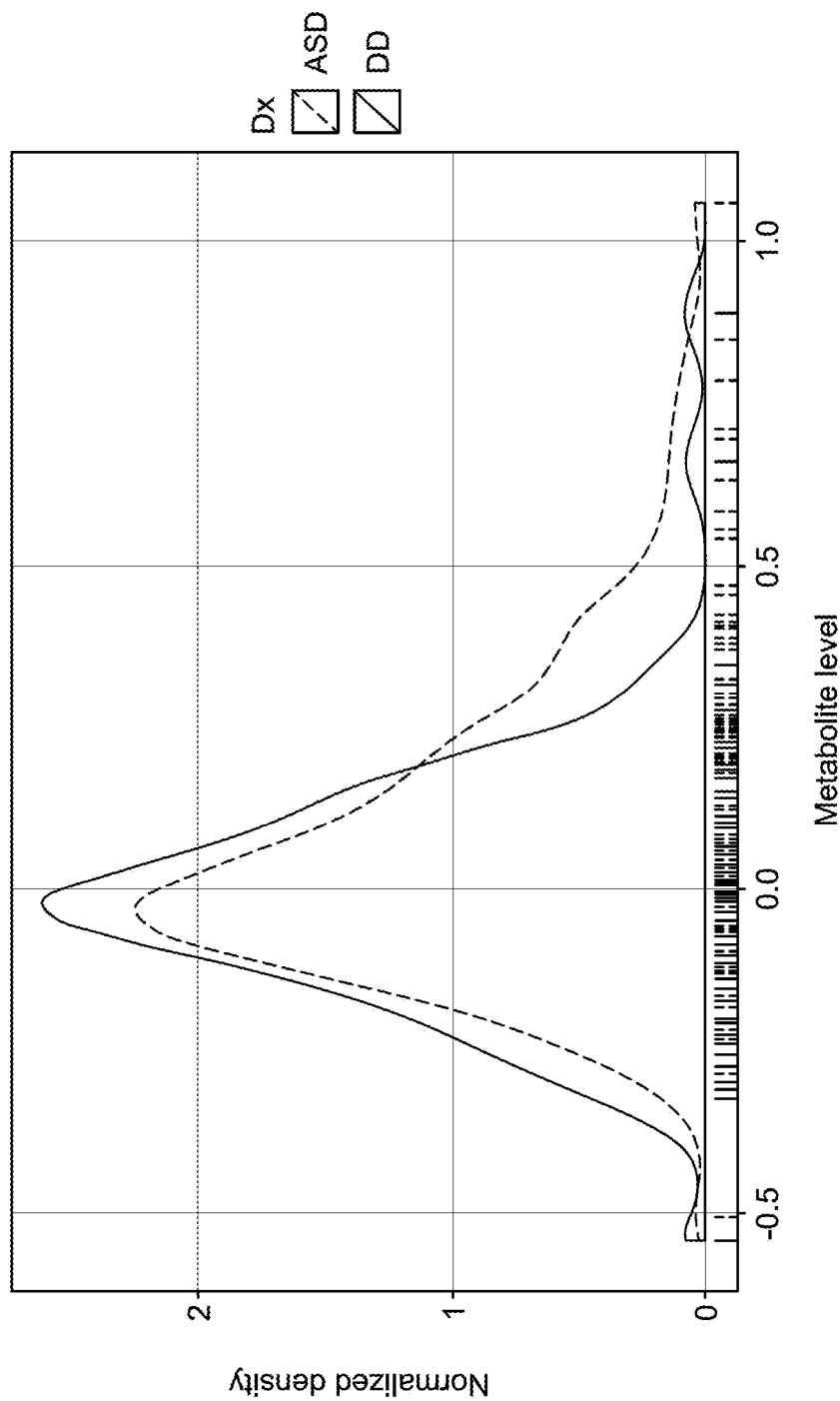
FIG. 2 illustrates the distribution of an exemplary metabolite in two populations (e.g., ASD and DD), and a tail effect (e.g., the ASD distribution has a more densely populated tail) of this metabolite between these two populations.

In addition to traditional mean shift analysis, the inventors discerned additional information from the samples. Metabolite distribution curves were plotted for ASD and non-ASD (here, DD) samples, and it was discovered that for a subset of metabolites measured, samples from either the ASD or the DD population were enriched in a right (upper) or left (lower) tail (i.e., a tail effect). A representative tail effect is shown in FIG. 2. Notably, the two distributions shared nearly identical mean values (i.e., there was minimal or no mean shift). Thus, the predictive value of the metabolite would not be discernible from traditional analysis of mean shifts.

Figure 3:
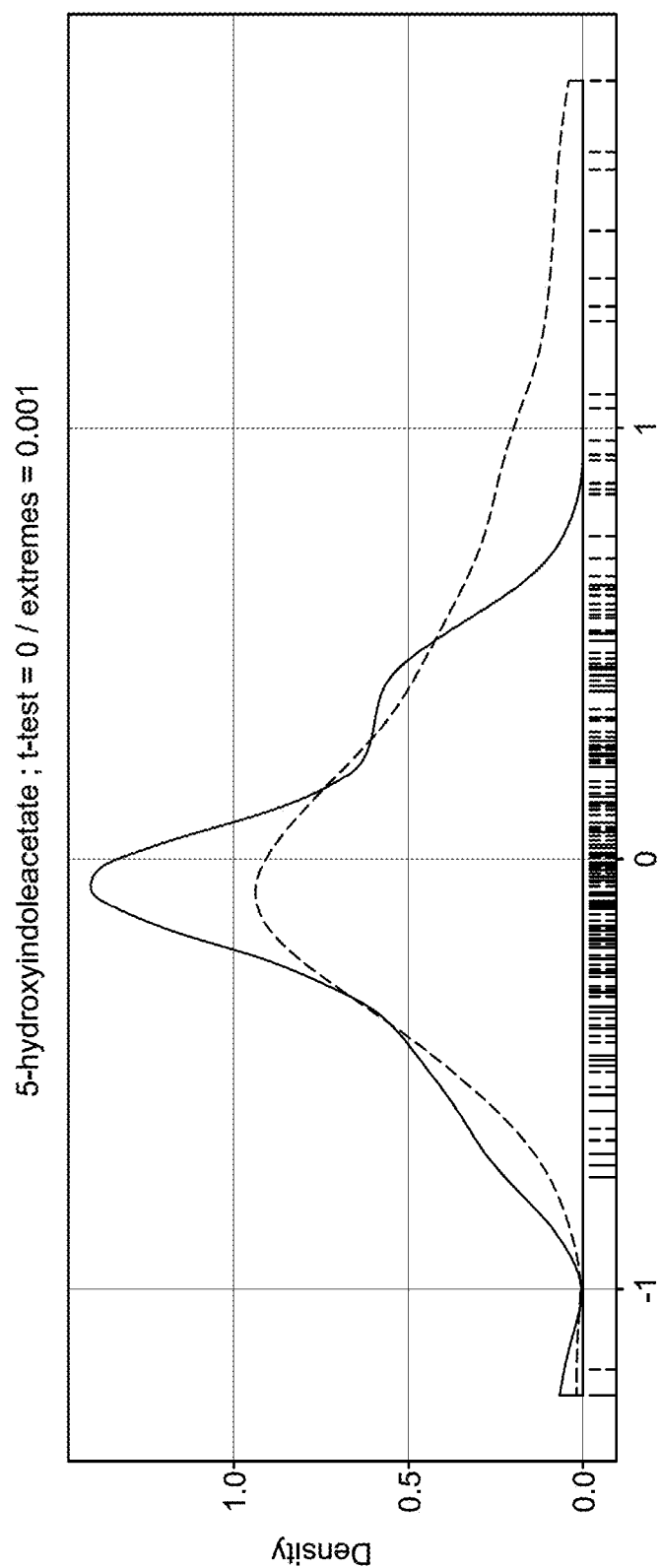
FIG. 3 illustrates the distribution of the metabolite 5-hydroxyindoleacetate, in two populations (e.g., ASD and DD), which exhibits a statistically significant mean shift (t-test; p<0.01) and a statistically significant right tail effect between the two populations. (extremes' signifies tail effect, Fisher's test; p=0.001)

Metabolites may exhibit a right (upper) tail effect, or a left (lower) tail effect, or both. ASD and non-ASD (here, DD) distribution curves for a representative metabolite, 5-HIAA are shown in FIG. 3. A clear right tail effect is observed, e.g., the ASD distribution has a larger AUC on the right tail. Thus, it is demonstrated that samples with high levels of this metabolite are highly enriched with ASD-population members. With this metabolite, both the mean shift (indicated by t-test value) and the right tail (indicated by 'extremes' Fisher test value) are statistically significant.

Figure 4:
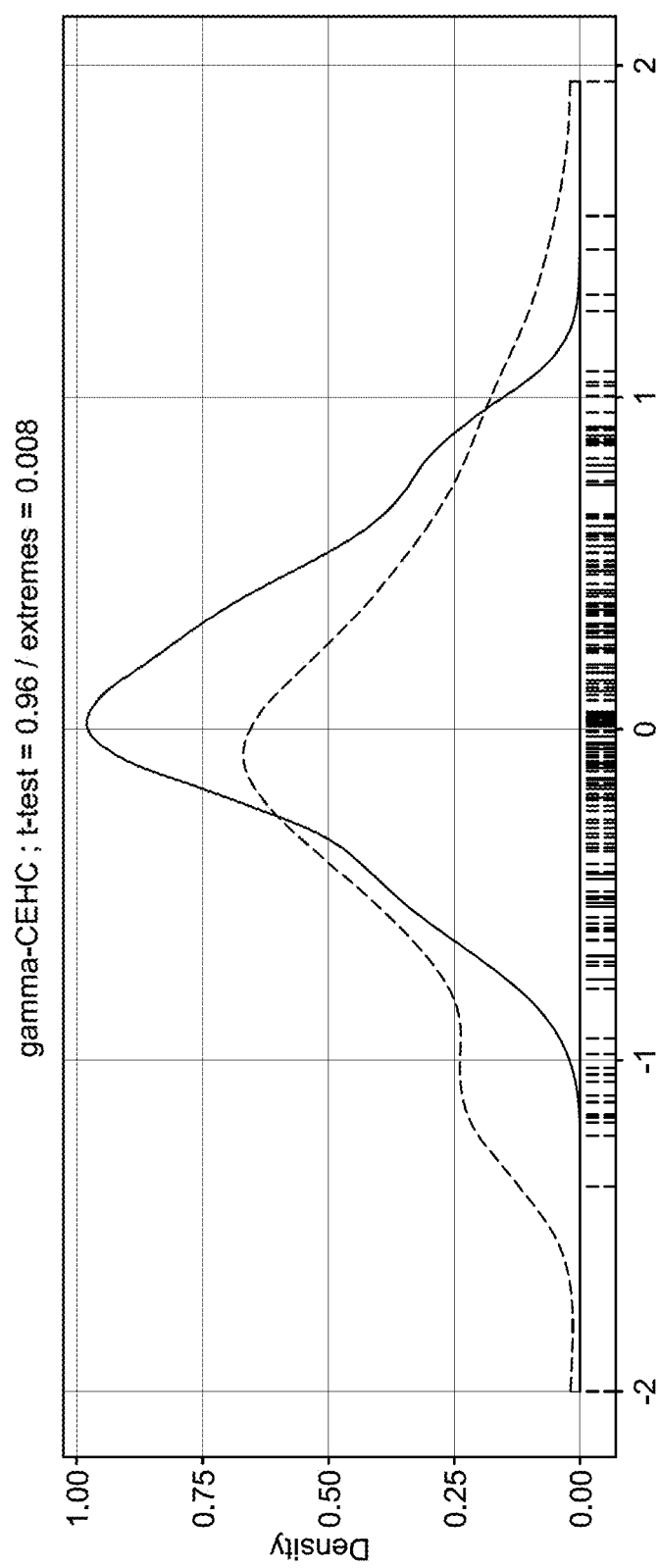
FIG. 4 illustrates the distribution of the metabolite, gamma-CEHC, in two populations (e.g., ASD and DD), which exhibits a statistically significant left tail effect between the two populations. (extremes' signifies tail effect, Fisher's test; p=0.008)

ASD and non-ASD (here, DD) distribution curves for another illustrative metabolite, gamma-CEHC, are shown in FIG. 4. A clear left tail effect is observed, e.g., the ASD distribution has a larger AUC on the left tail. Thus, it is demonstrated that samples with low levels of this metabolite are highly enriched with ASD-population members. With this metabolite, the mean shift (indicated by t-test value) is not statistically significant, while the left tail is statistically significant.

These data illustrate that identification and analysis of tail effects provides additional information for risk assessment that cannot be obtained via traditional mean shift analysis.

Example 2

Strong Prediction of ASD from Selected Metabolites Demonstrating Tail Effects

This example illustrates the assessment of tail effects for prediction of ASD. The inventors identified statistically significant tail effects for a number of metabolites in samples obtained from male subjects. The tail effects were singly and cumulatively informative about which population the subject belonged to—i.e., the ASD population or the DD population. Table 1 shows an exemplary panel of twenty-one metabolites exhibiting ASD vs. DD tail effects with high predictive power.

Table 1B shows metabolites of the 21-metabolite panel that have tail effects predictive of ASD. The statistical significance (p-value) of each tail effect as well as its location on a distribution curve (i.e., left tail effect or right tail effect) is indicated. An odds ratio of greater than one indicates predictive power for ASD. For example, 5HIAA has a right tail with an odds ratio of 4.91, indicating that in the STORY study data set (in which the ratio of ASD to DD samples was 2:1), approximately 10 ASD samples for every DD sample was in the right tail. The confidence intervals were estimated by bootstrap methods. One thousand individual bootstraps were generated from the STORY data by resampling with replacement. For each bootstrap, the position of the tail and corresponding odds ratio was determined. The 90% confidence interval was calculated from the distribution of observed odds ratios.

Based on these criteria, nineteen metabolites of the 21-metabolite panel were found to be predictive of ASD.

Table 1C shows metabolites having tail effects that are predictive of DD. The statistical significance (p-value) of each tail effect as well as its location on a distribution curve (i.e., left tail effect or right tail effect) is indicated. An odds ratio of less than one indicates predictive power for DD. Based on these criteria, eight metabolites of the 21-metabolite panel were found to be predictive of DD. The odds ratio and 90% confidence intervals were determined similarly for ASD, taking into account the 1:2 ratio of DD to ASD samples in the STORY study.

Notably, certain metabolites demonstrate a single tail effect (either left or right) with predictive power for either ASD or DD, whereas other metabolites demonstrate both a left and right tail effect, together providing predictive power for both ASD and DD. For example, phenylacetylglutamine and p-cresol sulfate demonstrate both right and left tail effects.

Figure 13A:
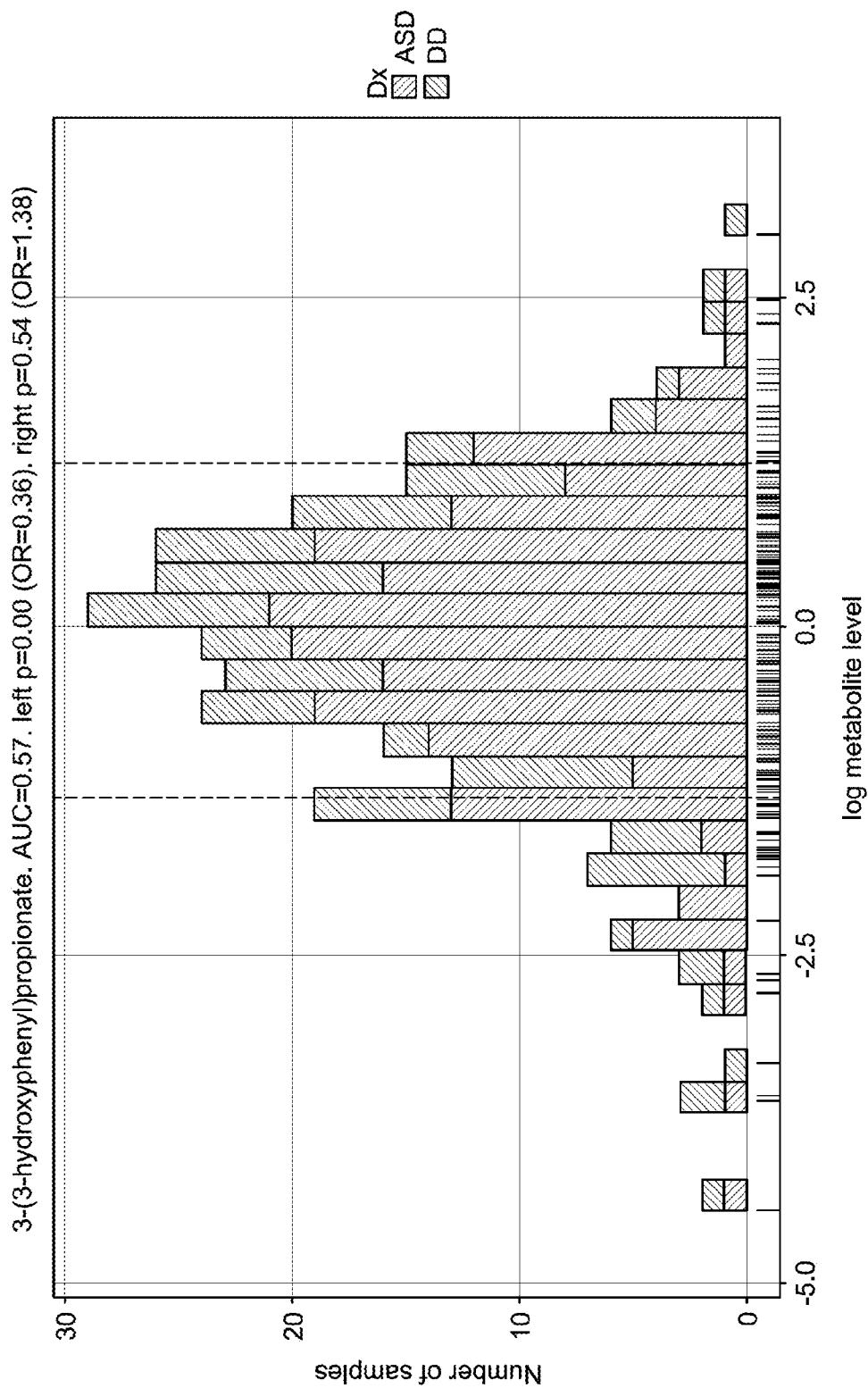
FIGS. 13A-13U illustrate the population distribution of 21 exemplary metabolites in an ASD population and a non-ASD population.
Figure 13B:
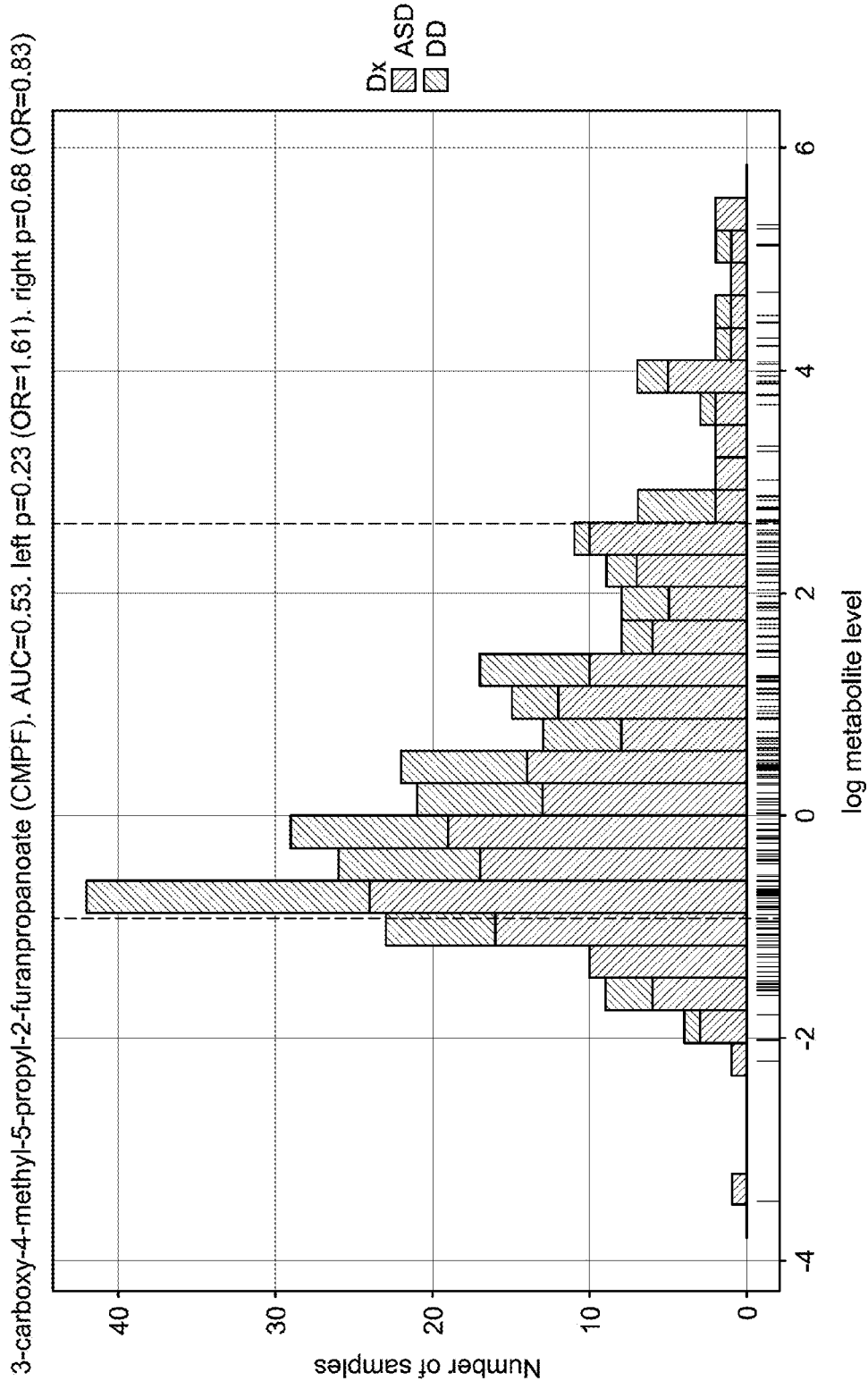
Figure 13C:
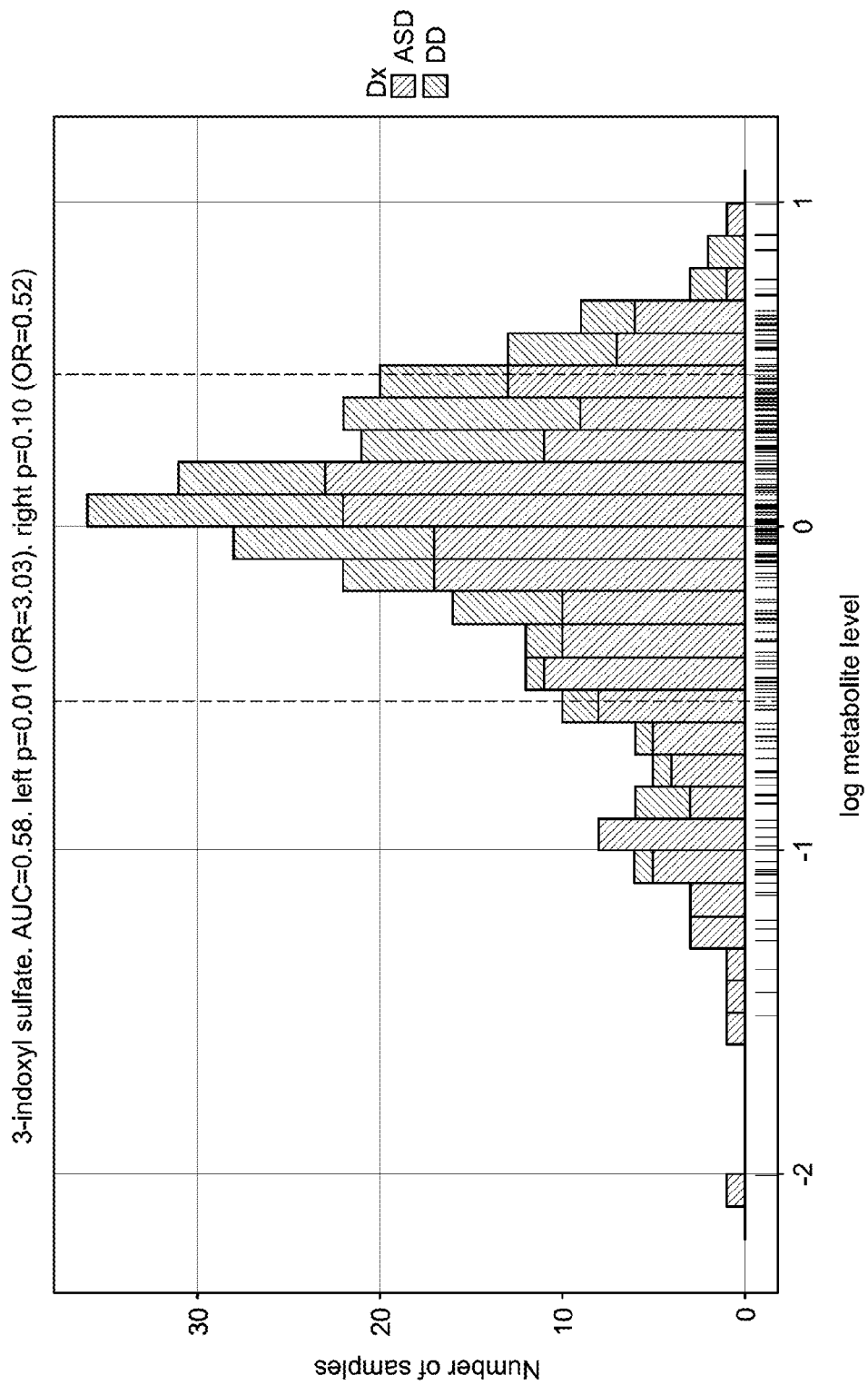
Figure 13D:
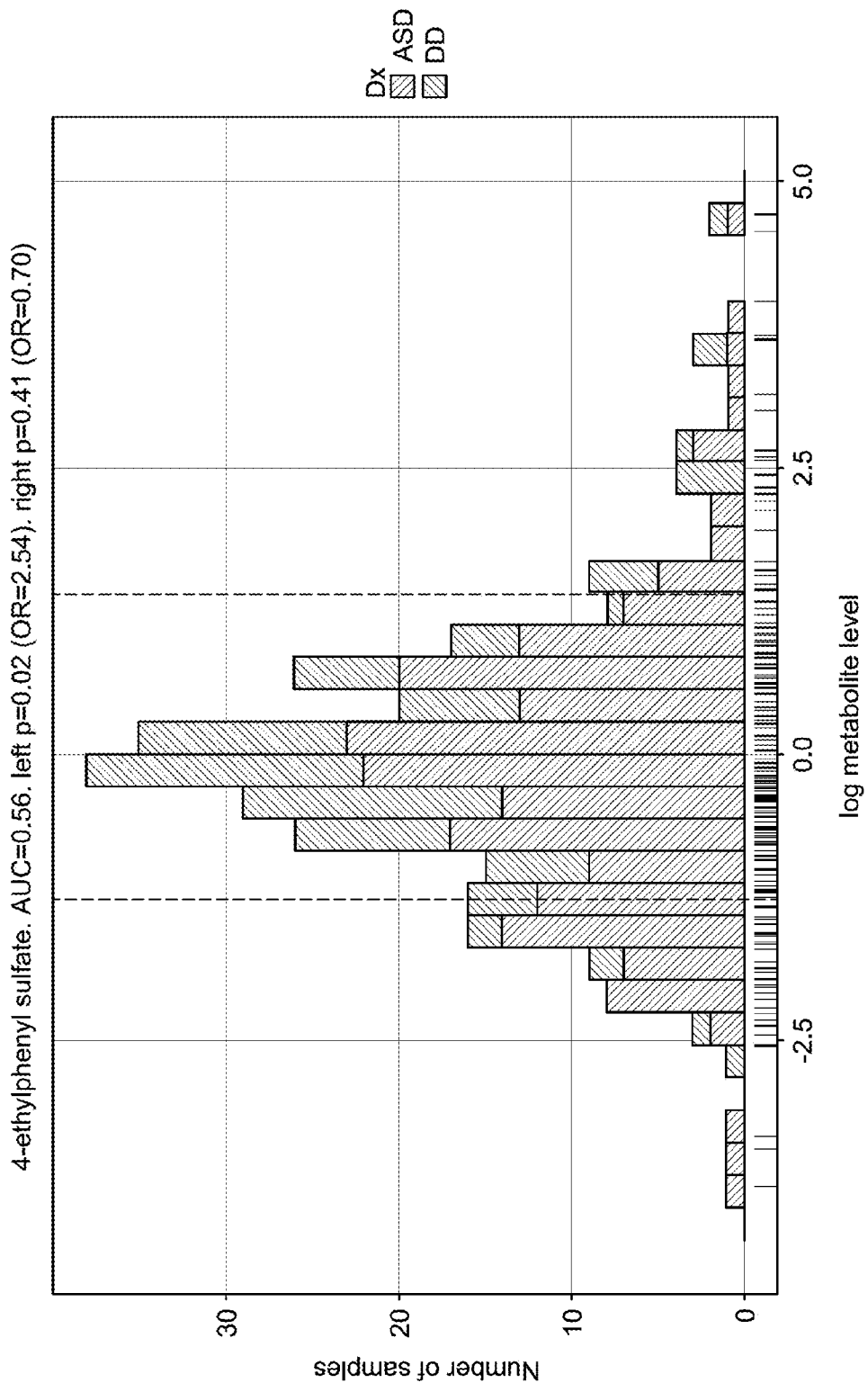
Figure 13E:
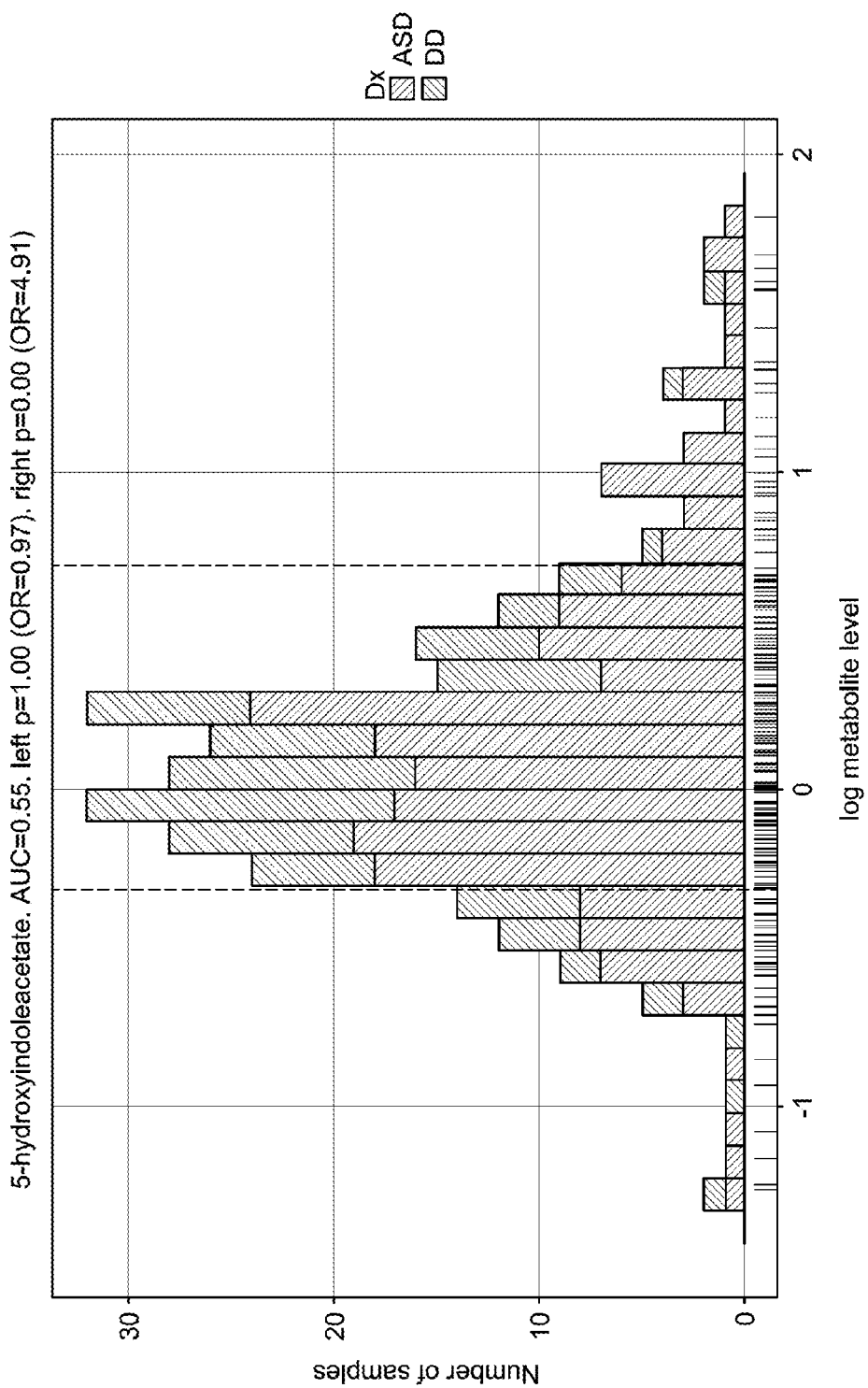
Figure 13F:
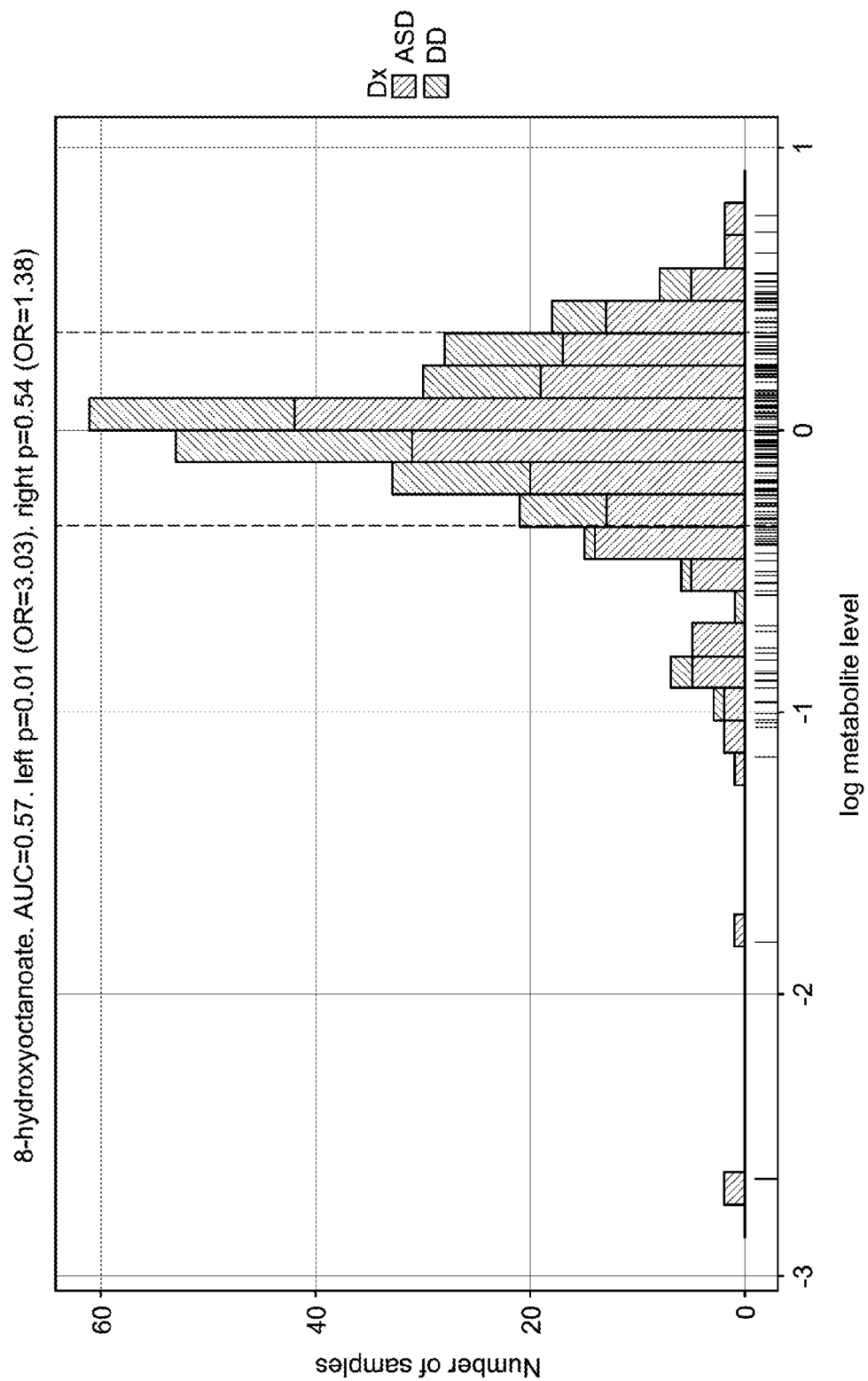
Figure 13G:
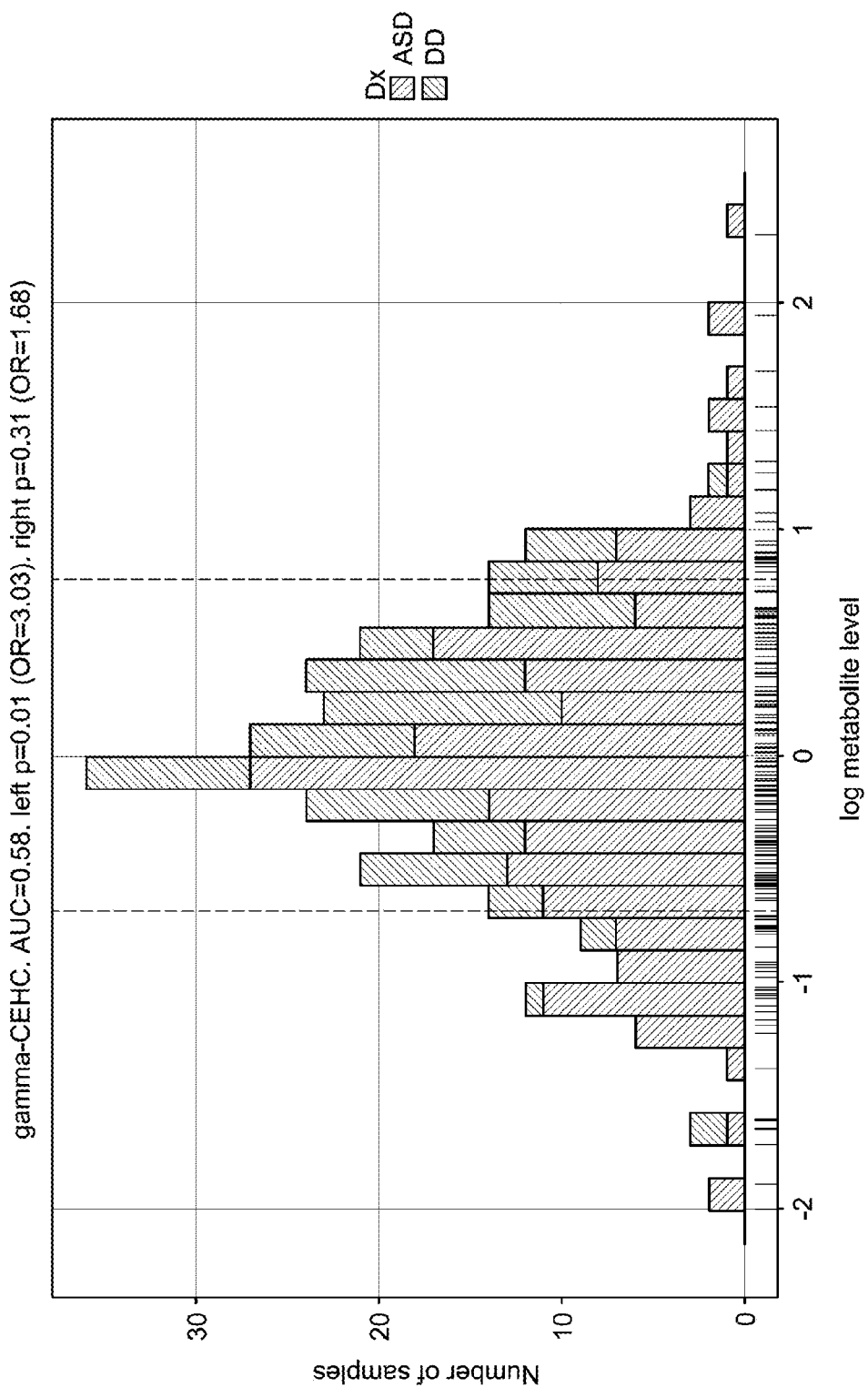
Figure 13H:
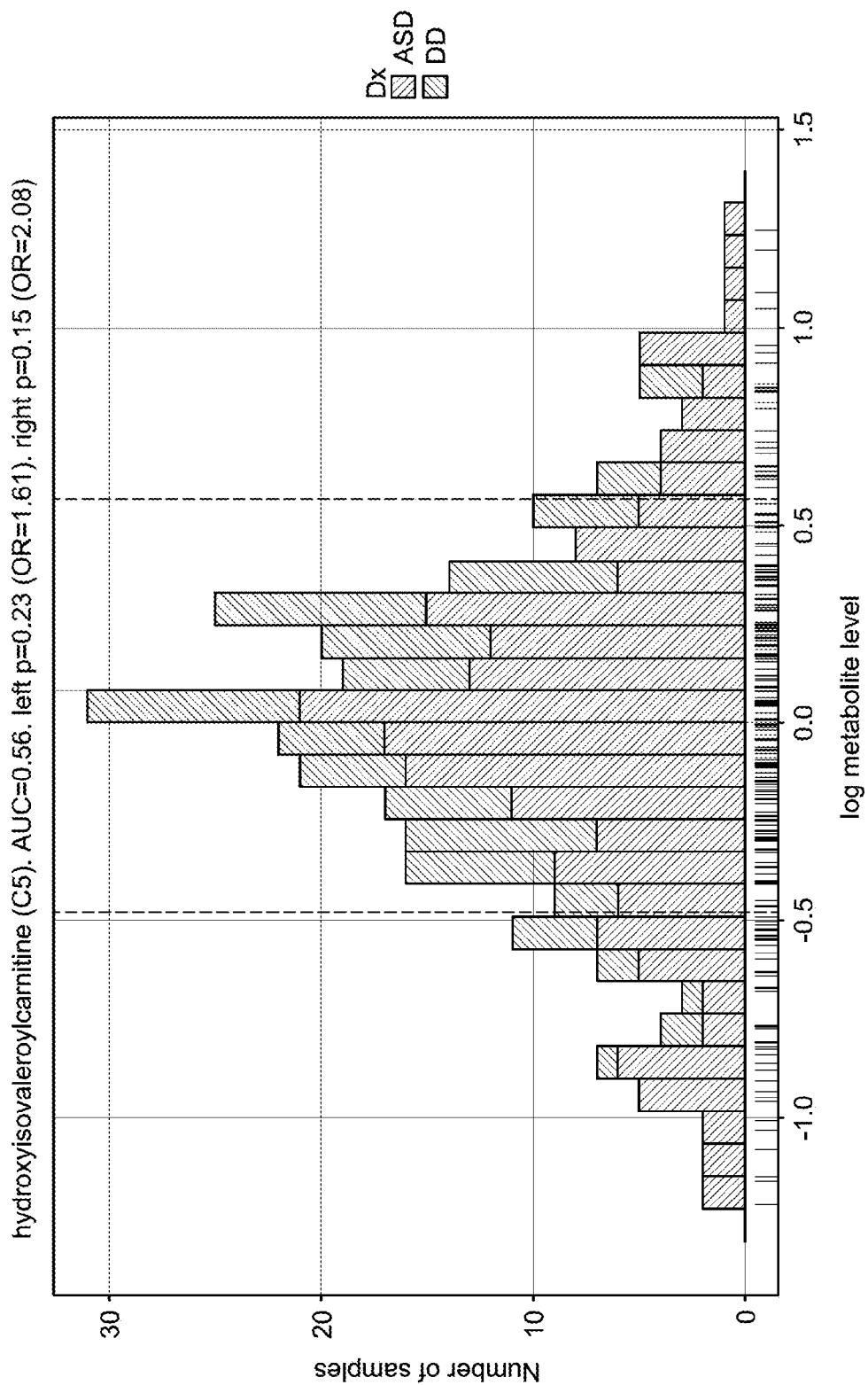
Figure 13I:
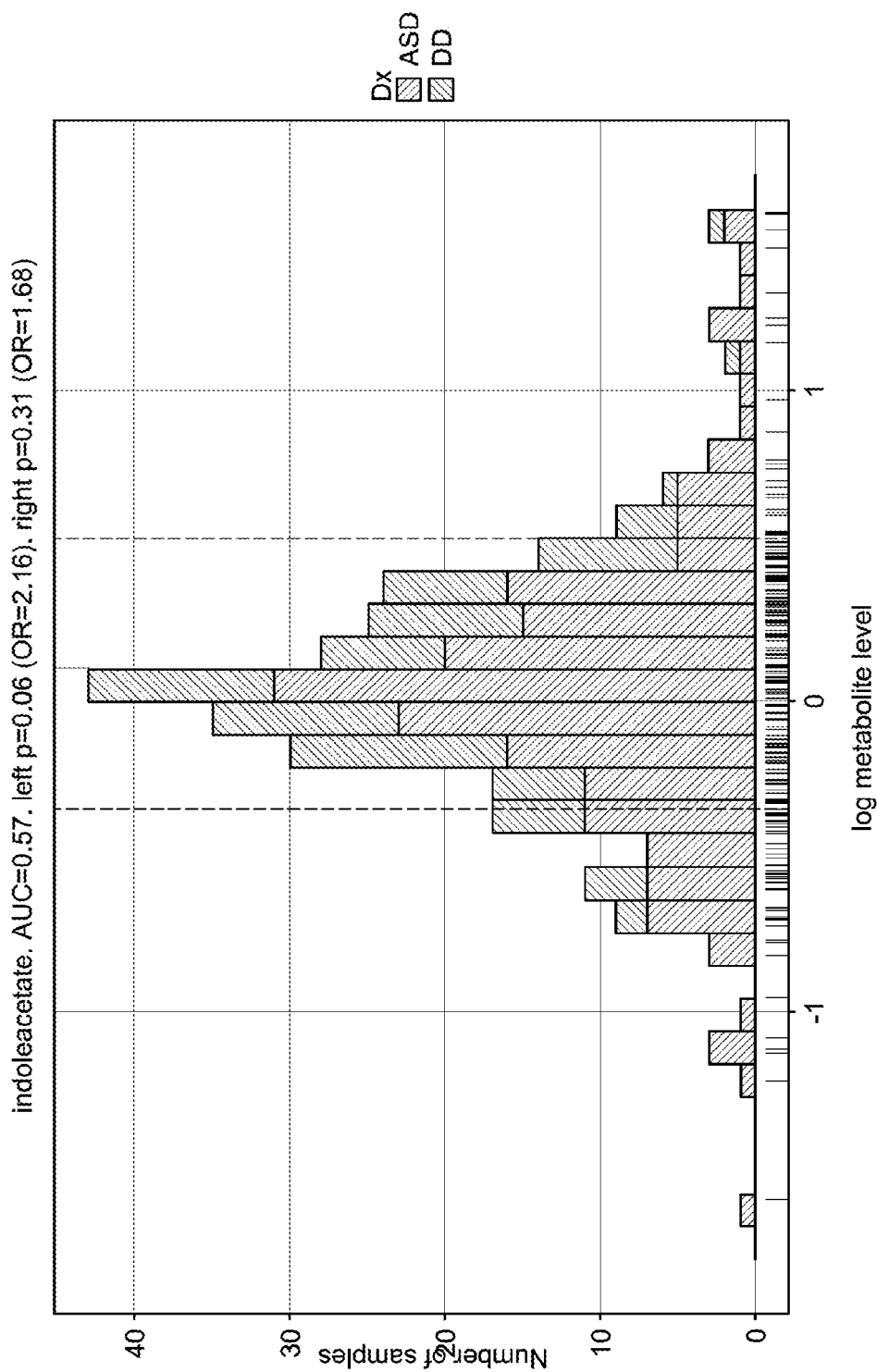
Figure 13J:
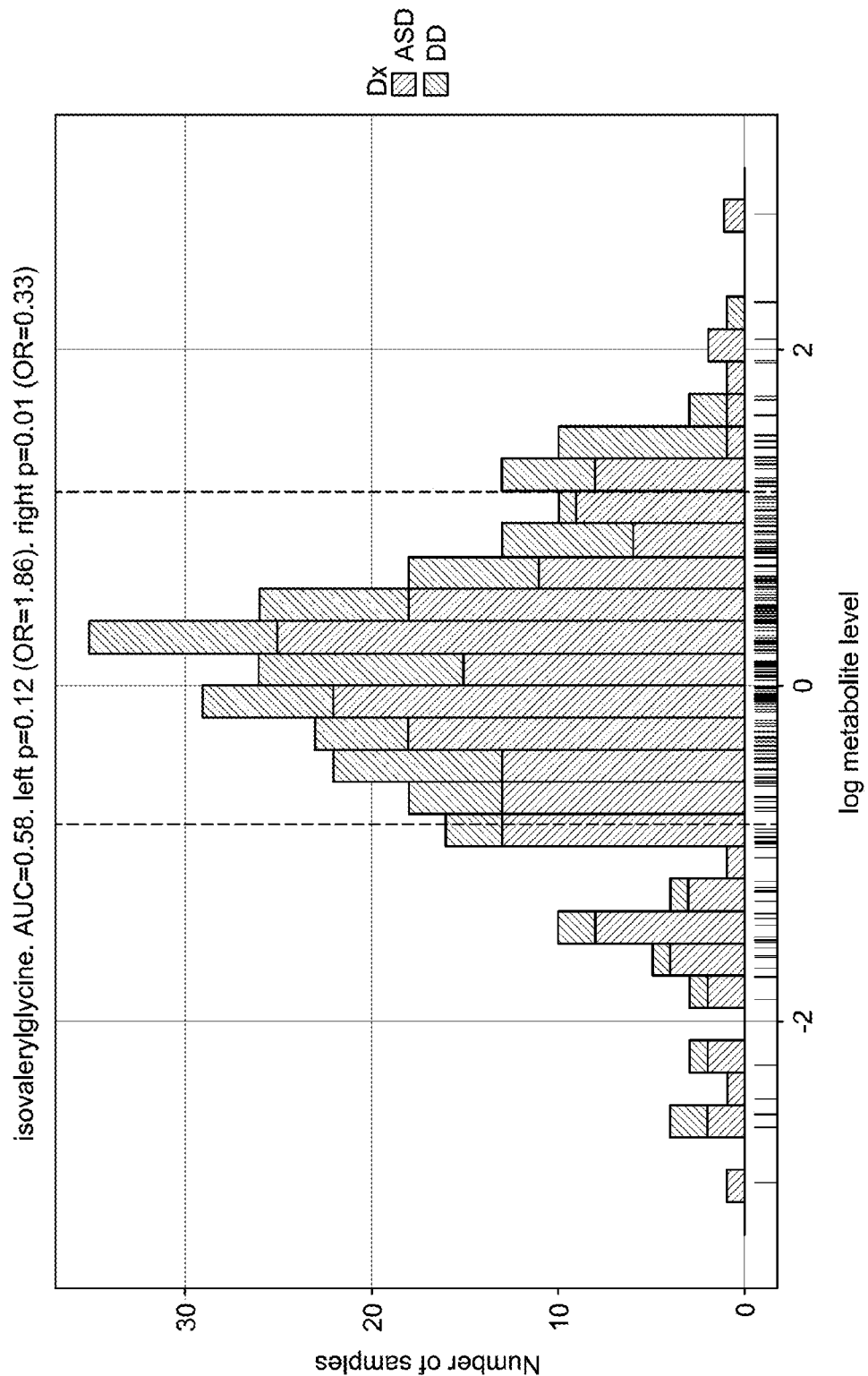
Figure 13K:
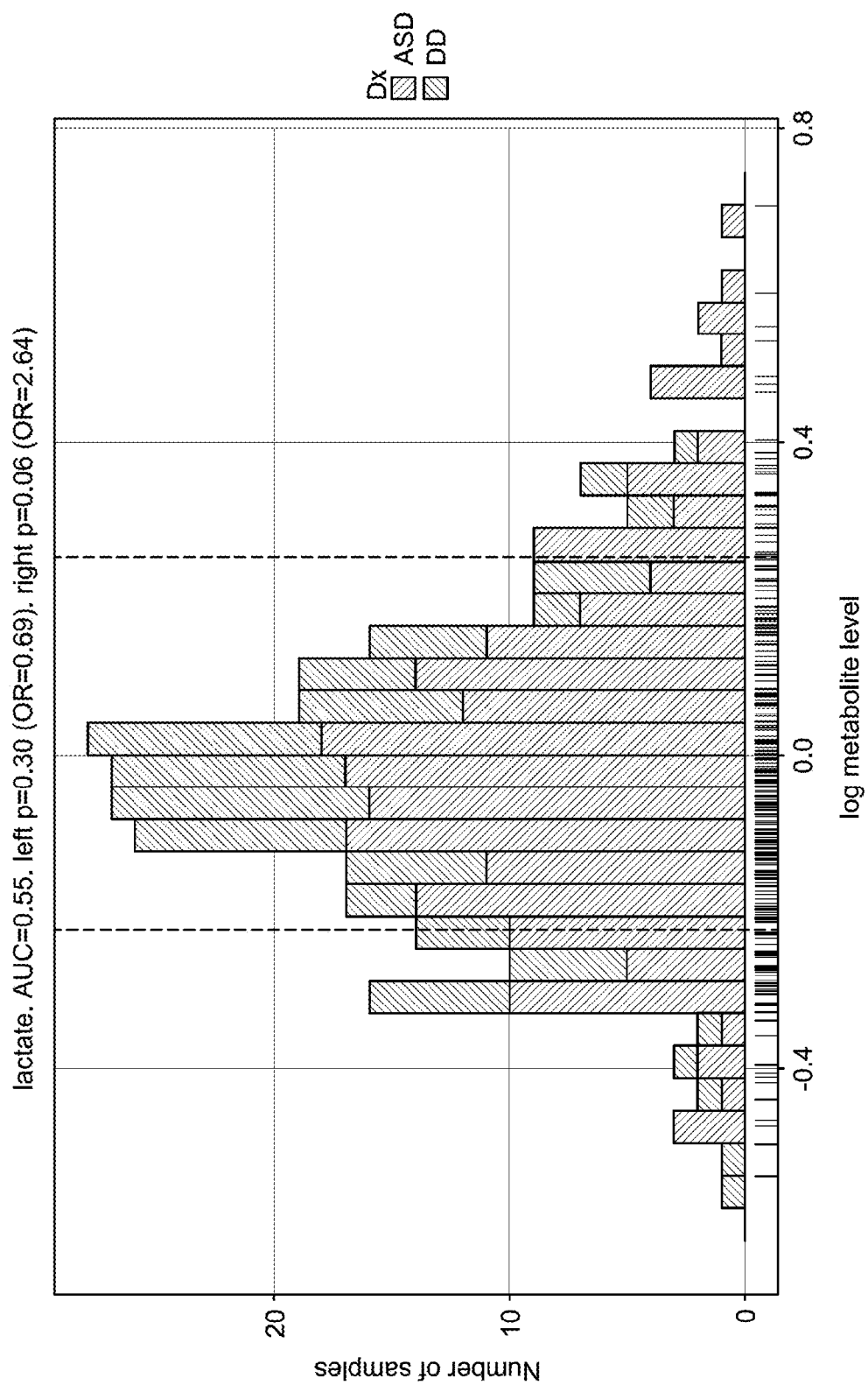
Figure 13L:
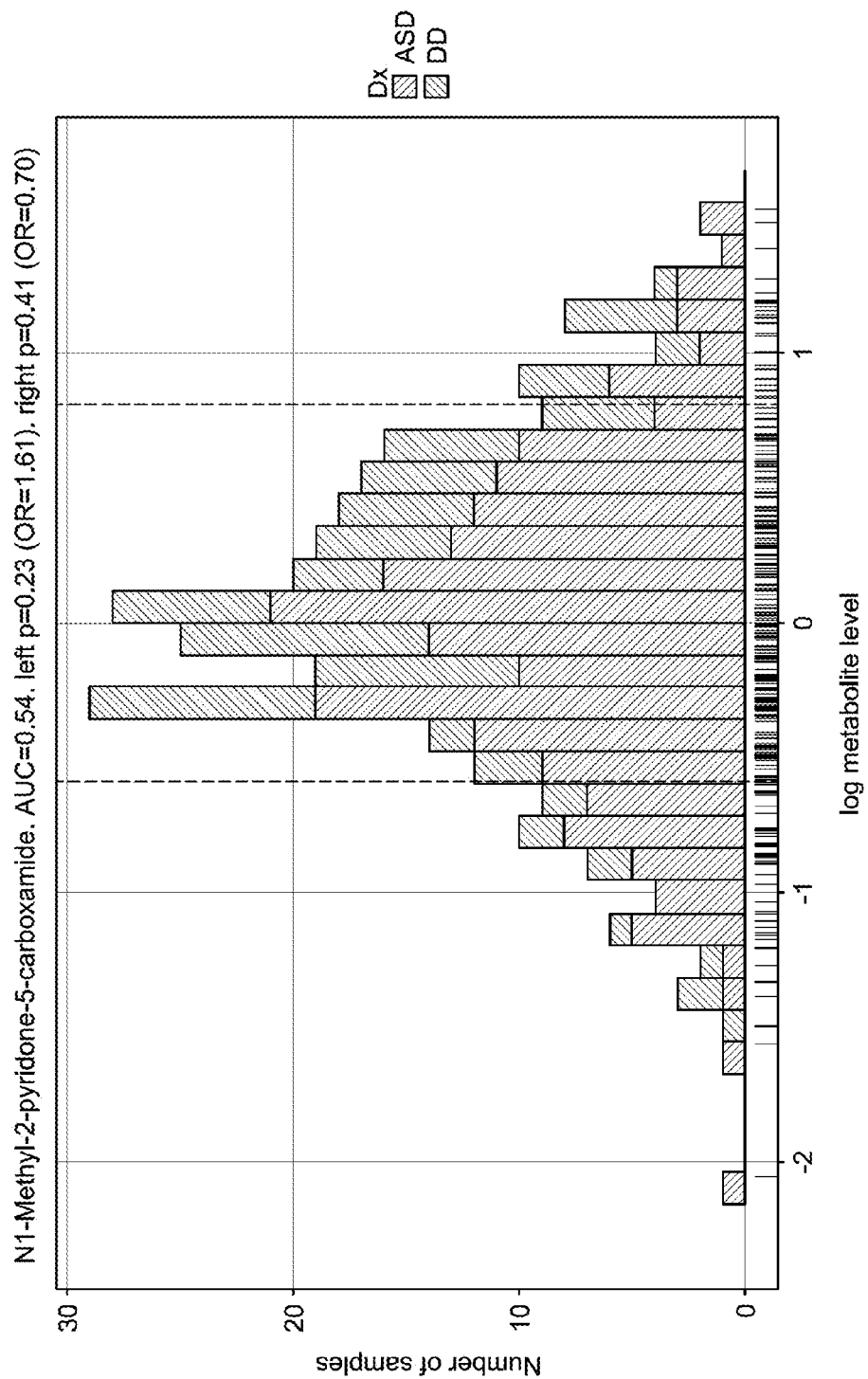
Figure 13M:
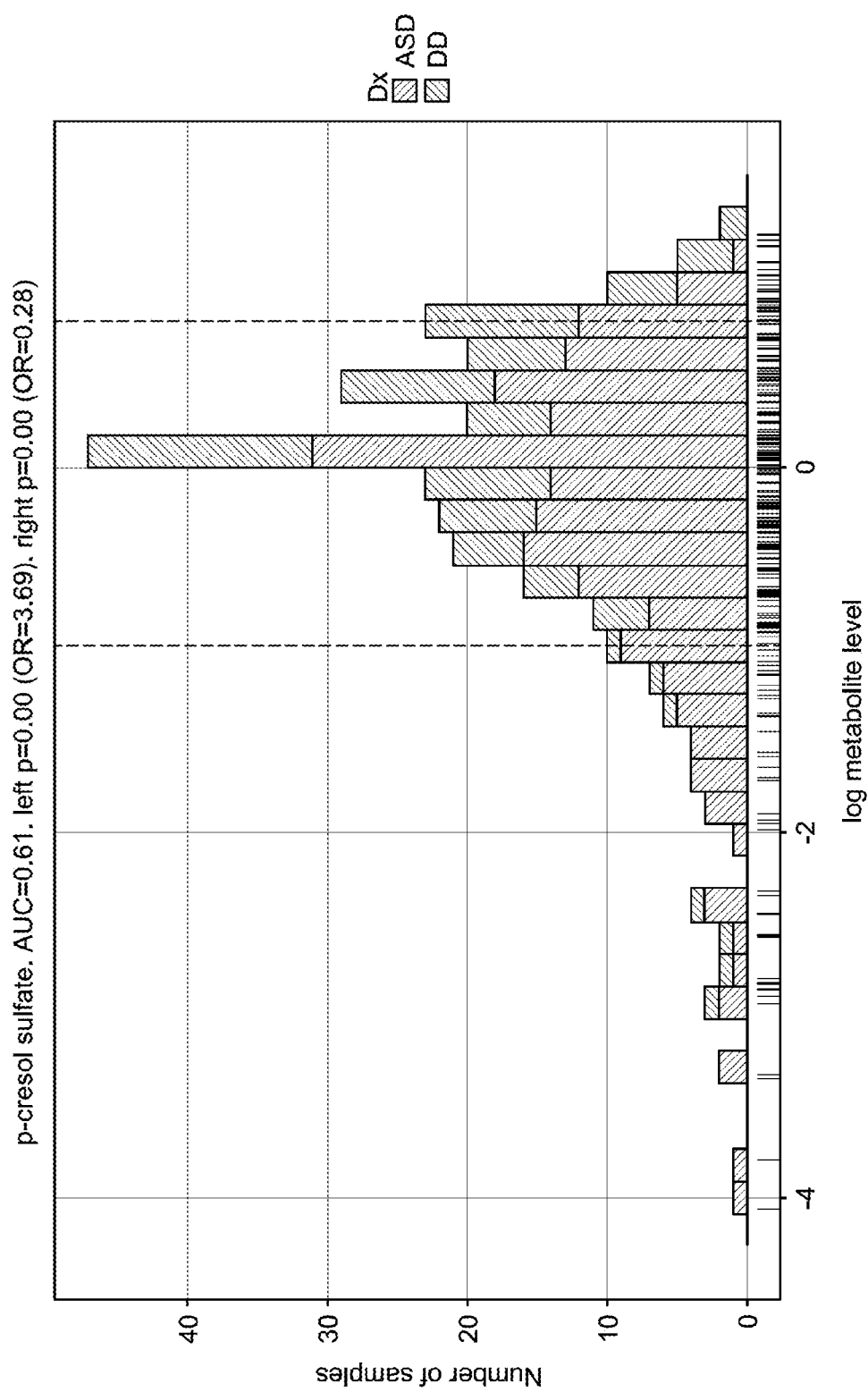
Figure 13N:
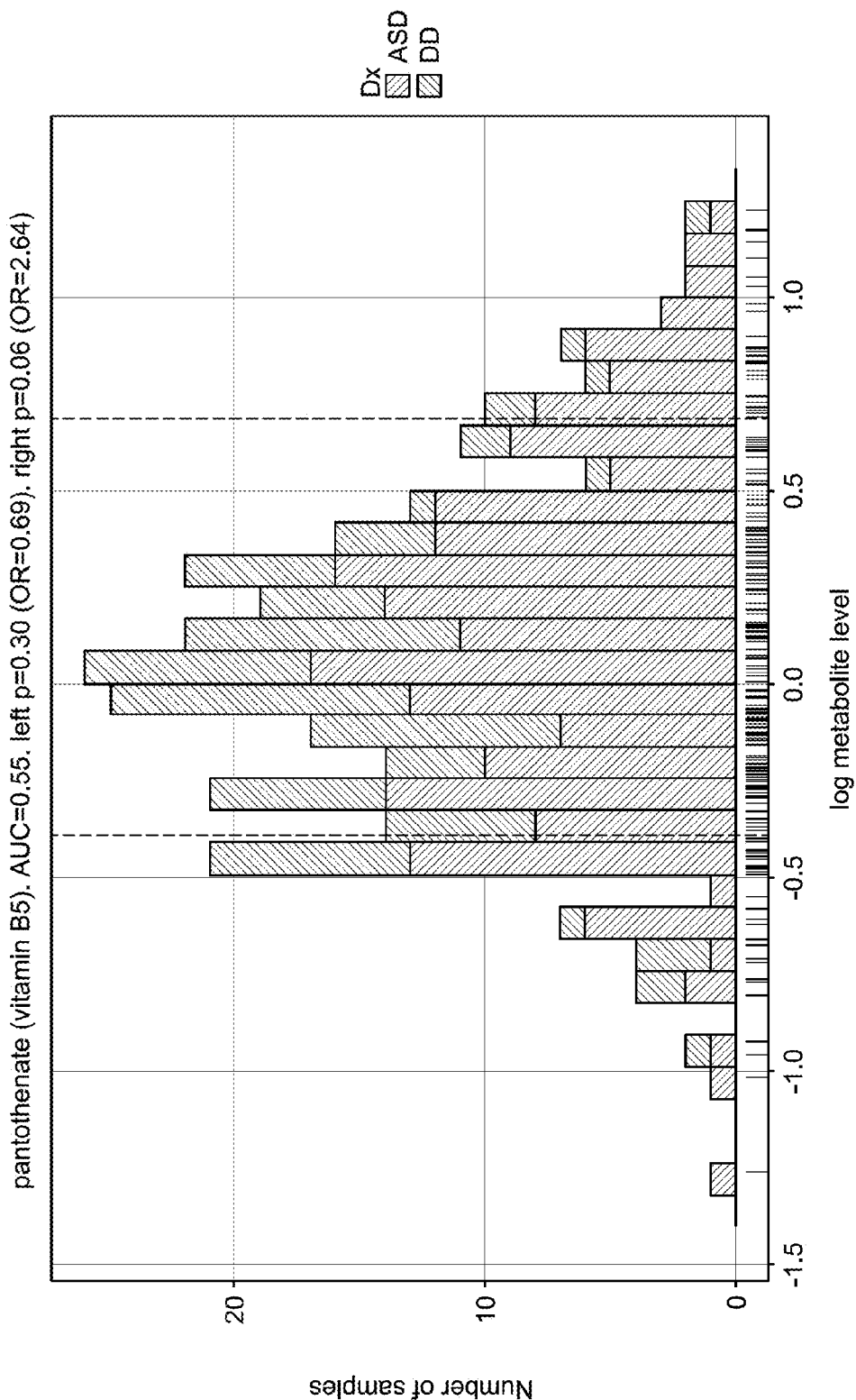
Figure 13O:
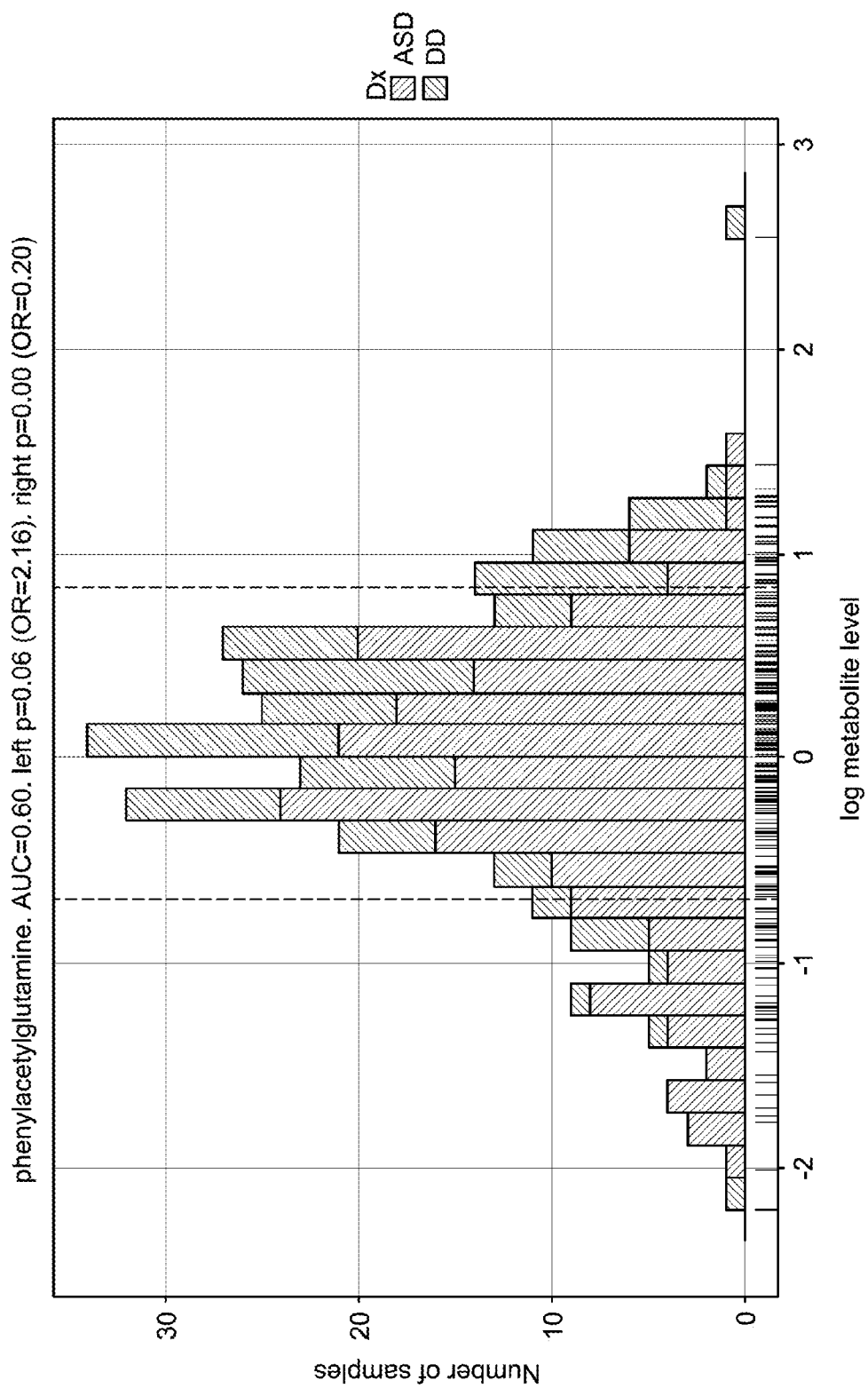
Figure 13P:
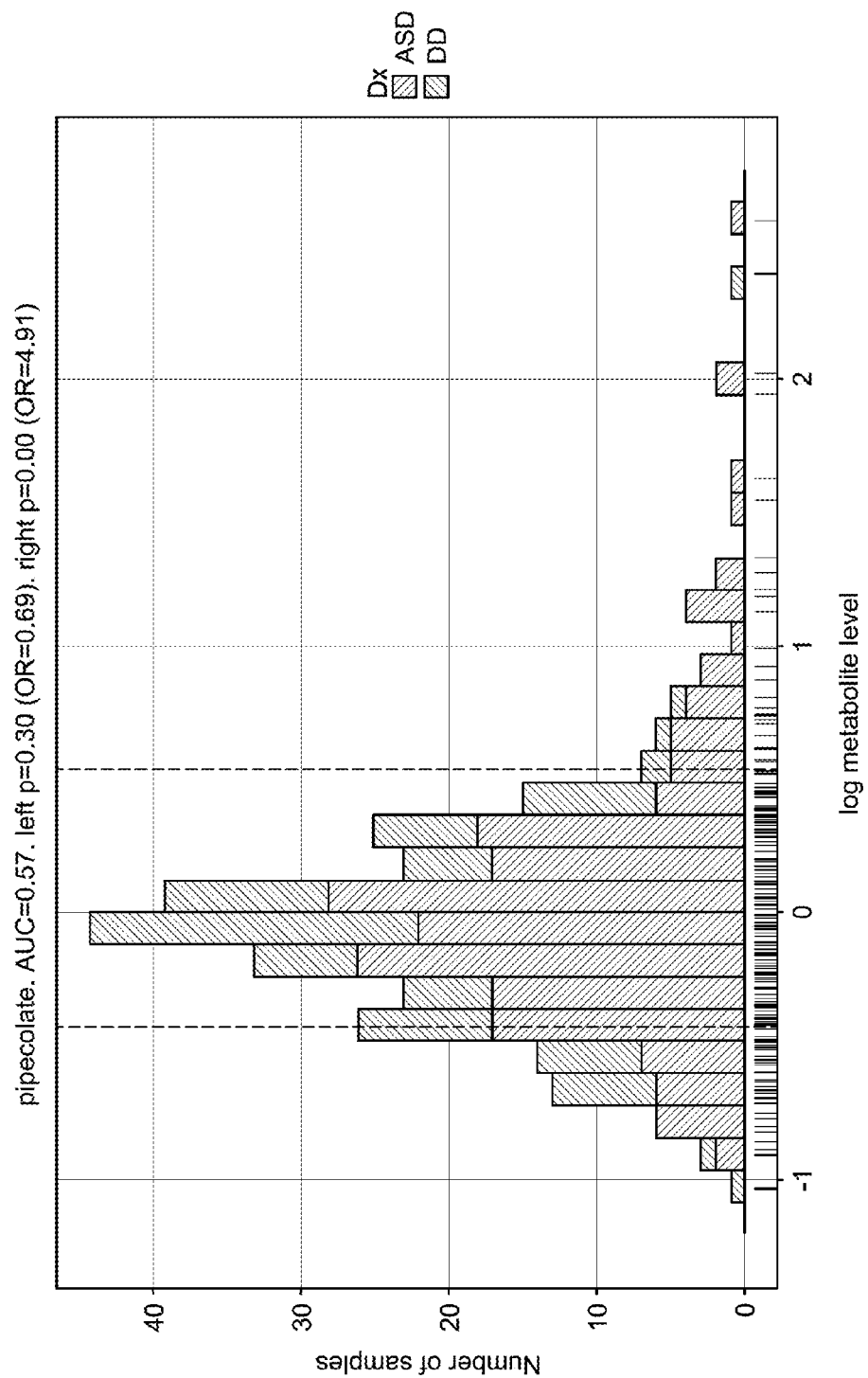
Figure 13Q:
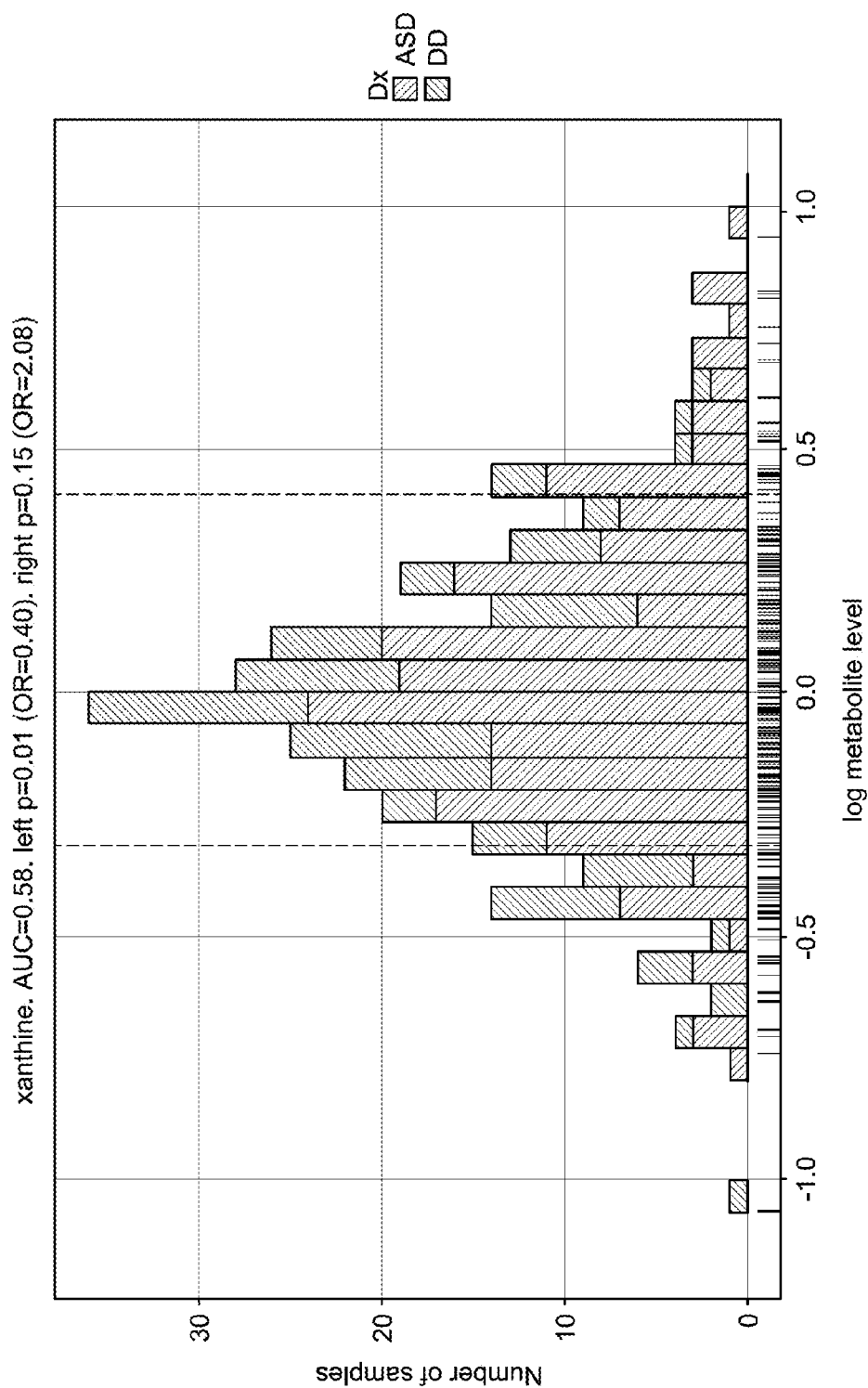
Figure 13R:
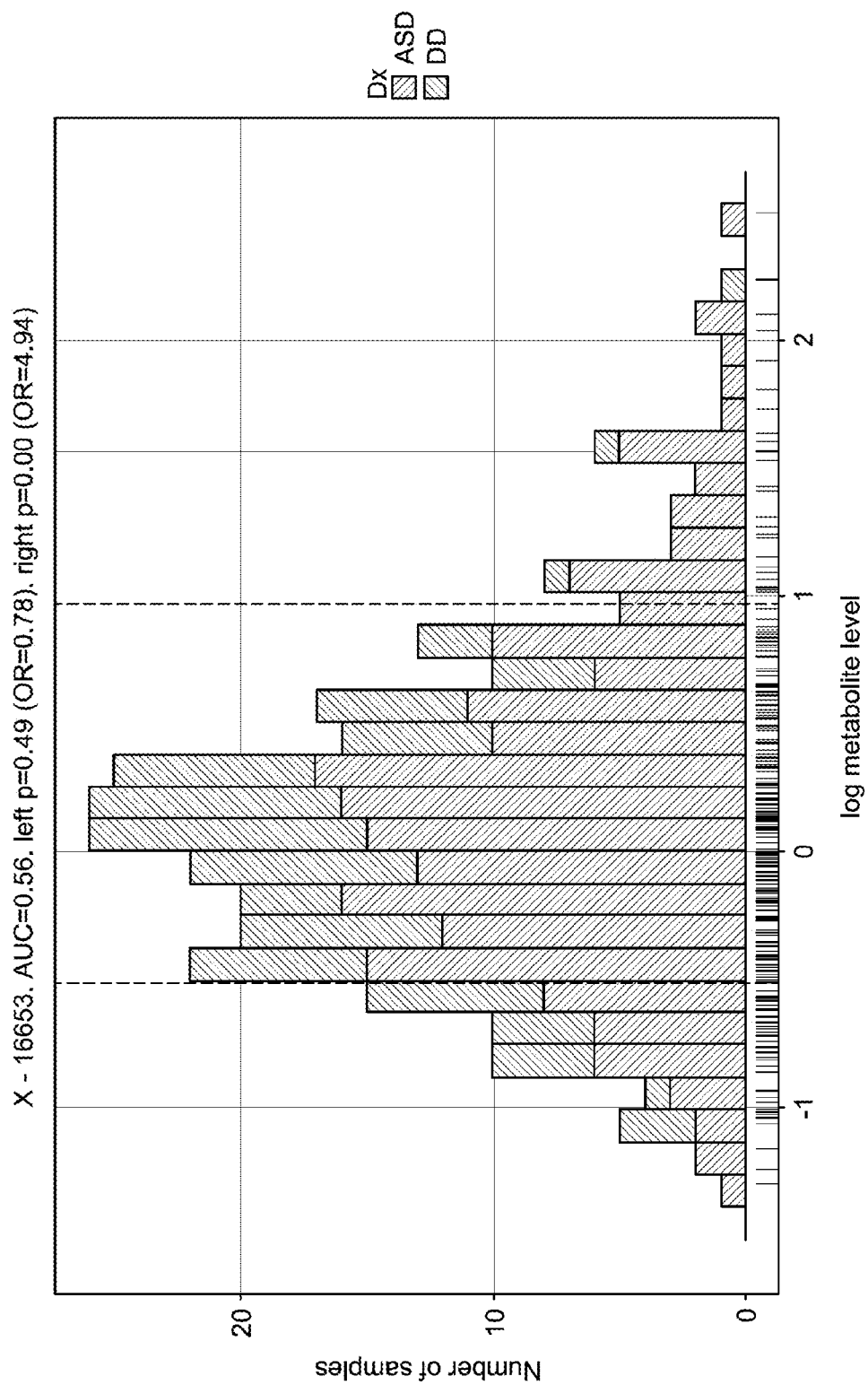
Figure 13S:
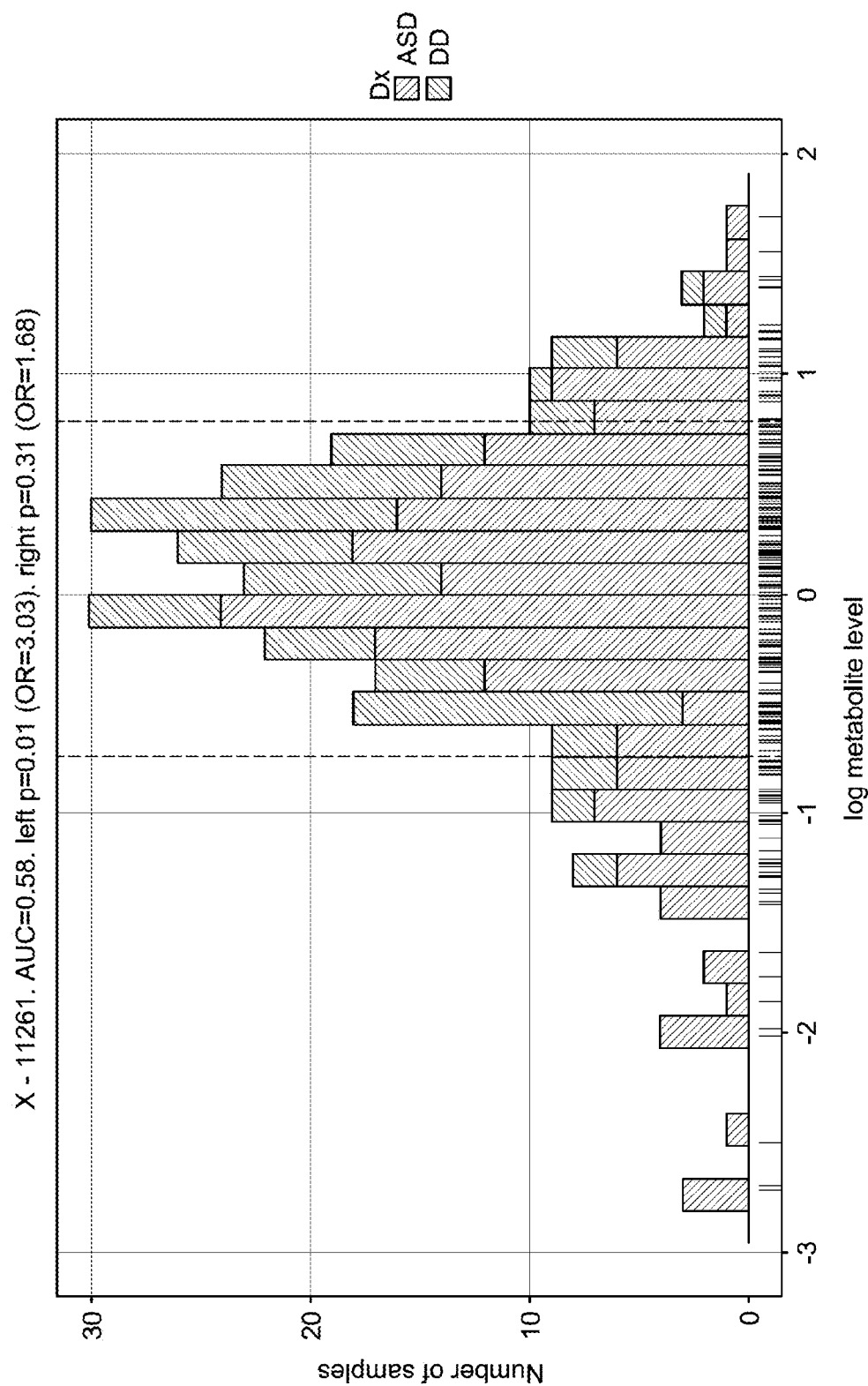
Figure 13T:
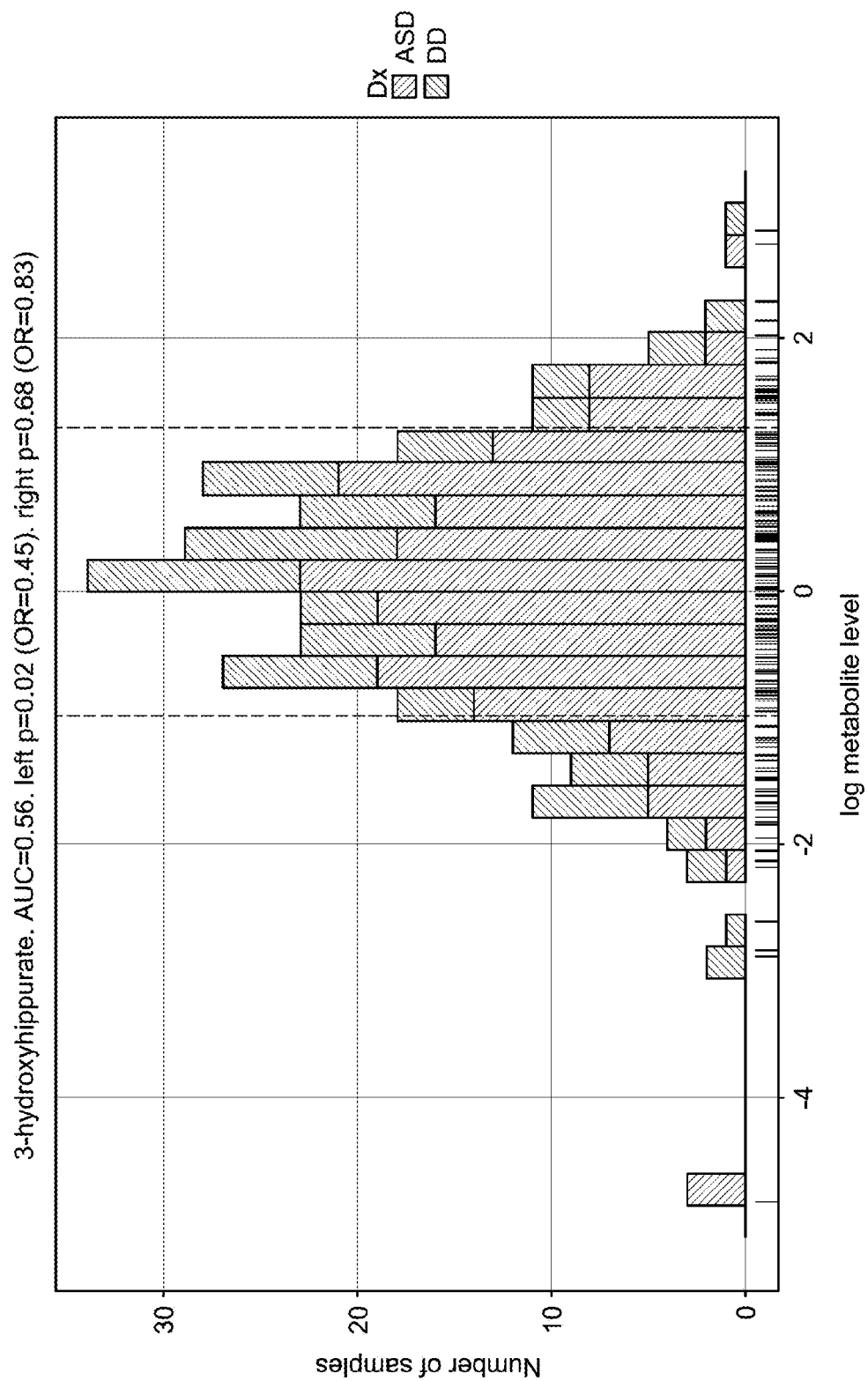
Figure 13U:
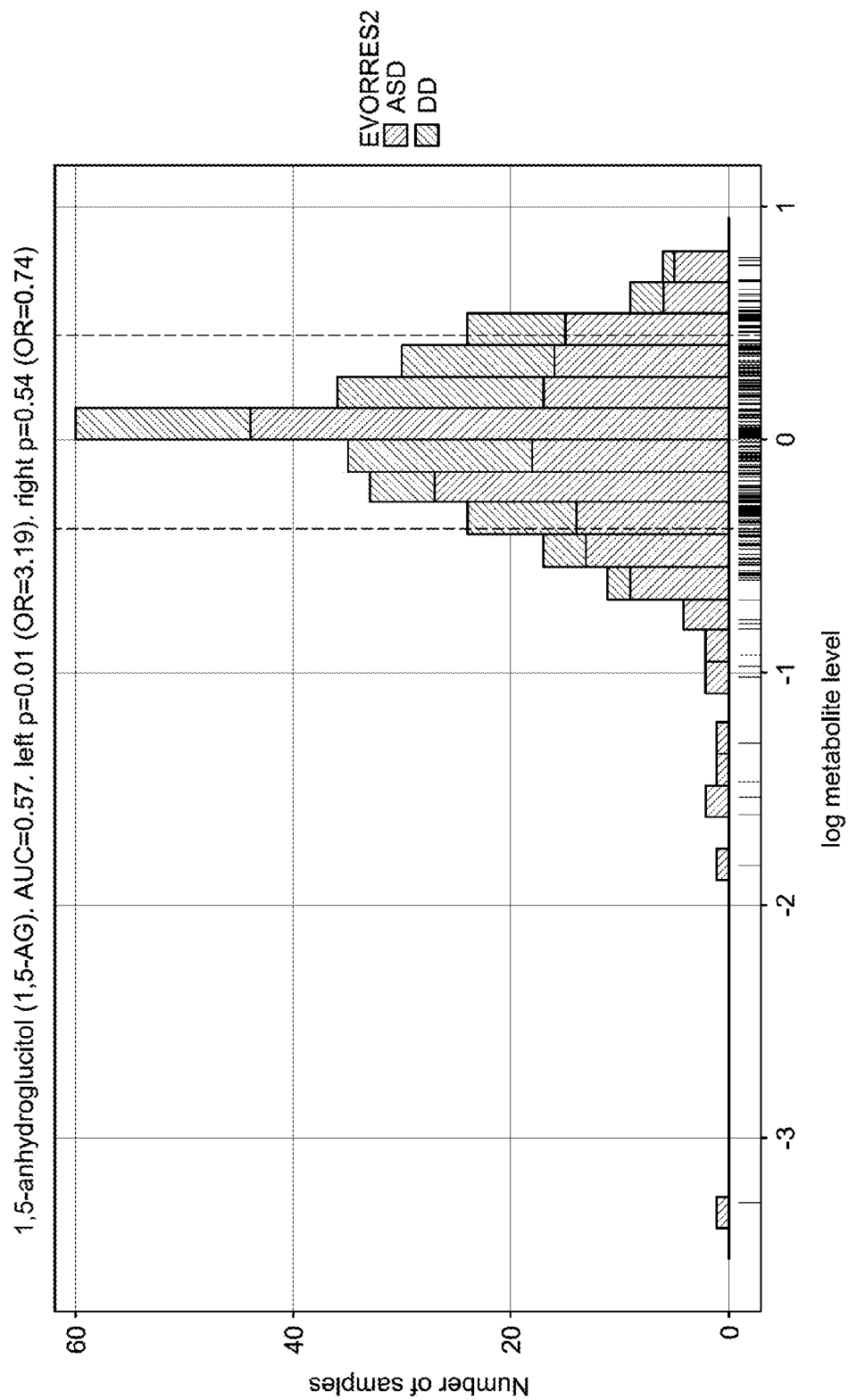

The tail effects of the 21 metabolites listed in Table 1 are shown individually in the graphs of FIGS. 13A to 13U. For each graph, distributions of one metabolite in both the ASD and DD populations are shown. The legend at the top of each panel shows the statistical significance of the left and right tails for the metabolite (p-value generated by Fisher's test).

Figure 5:
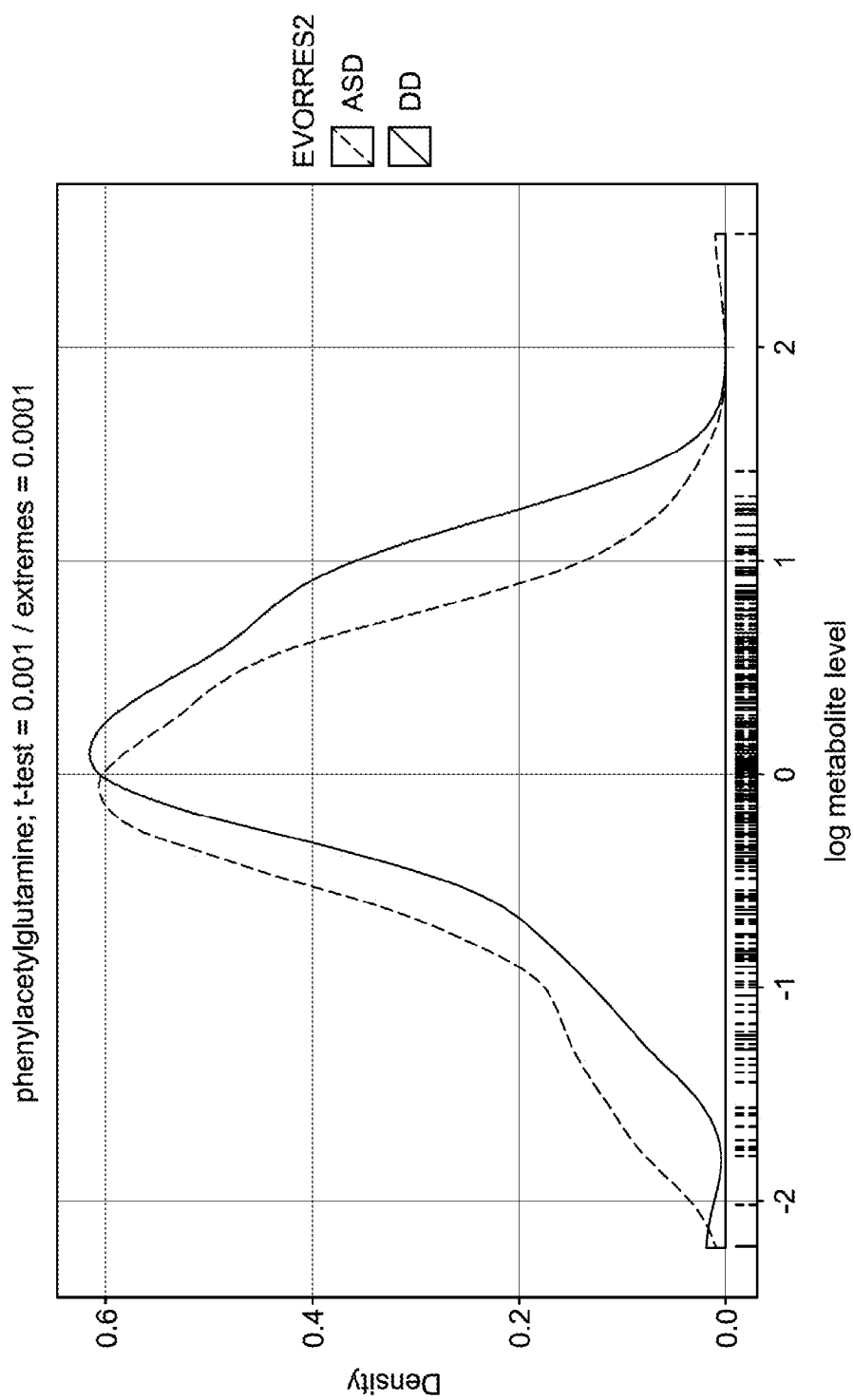
FIG. 5 illustrates the distribution of the metabolite, phenylacetylglutamine, in two populations (e.g., ASD and DD), which exhibits a statistically significant mean shift (t-test; p=0.001), and statistically significant left and right tail effects between the two populations (extremes' signifies tail effect, Fisher's test; p=0.0001). The distributions appear as shifted Gaussian curves in the two populations.

Some metabolites, e.g., phenylacetylglutamine, exhibit mean shifts and tail effects. As shown in FIG. 5, phenylacetylglutamine exhibits a statistically significant mean shift (t-test; p=0.001), and statistically significant left and right tail effects between the two populations (extremes' signifies tail effect, Fisher's test; p=0.0001). The distributions appear as shifted Gaussian curves between the ASD and DD populations.

Table 2 shows threshold values used to determine the tail effects for the 21-metabolite panel, based on the underlying population distribution of each metabolite in the ASD and non-ASD populations. Illustratively, the upper threshold value corresponds to the $90^{th}$ percentile distribution, while the lower threshold value corresponds to the $15^{th}$ percentile distribution. The absolute measurements of the threshold values (e.g., ng/mL, nM, etc.) can be calculated by using values in Table 2 with average concentrations of the metabolites in a population.

TABLE 2

Threshold levels for left tail (at or below $15^{th}$ percentile) and right tail (at or above $90^{th}$ percentile) of metabolite distribution curve

| Metabolite | Left tail cut-off | Right tail cut-off |
| --- | --- | --- |
| 1,5-anhydroglucitol (1,5-AG) | 0.680 | 1.561 |
| 3-(3-hydroxyphenyl)propionate | 0.270 | 3.462 |
| 3-carboxy-4-methyl-5-propyl-2-furanpropanoate (CMPF) | 0.396 | 13.734 |
| 3-indoxyl sulfate | 0.584 | 1.601 |
| 4-ethylphenyl sulfate | 0.281 | 4.054 |
| 5-hydroxyindoleacetate | 0.729 | 2.027 |
| 8-hydroxyoctanoate | 0.711 | 1.411 |
| gamma-CEHC | 0.505 | 2.199 |
| hydroxyisovaleroylcarnitine (C5) | 0.619 | 1.767 |
| indoleacetate | 0.707 | 1.690 |
| isovalerylglycine | 0.438 | 3.182 |
| lactate | 0.801 | 1.288 |
| N1-Methyl-2-pyridone-5-carboxamide | 0.554 | 2.254 |
| p-cresol sulfate | 0.378 | 2.231 |
| pantothenate (Vitamin B5) | 0.675 | 1.980 |
| phenylacetylglutamine | 0.498 | 2.305 |
| pipecolate | 0.651 | 1.711 |
| xanthine | 0.731 | 1.507 |
| hydroxy-chlorothalonil | 0.597 | 2.645 |
| octenoylcarnitine | 0.479 | 2.214 |
| 3-hydroxyhippurate | 0.375 | 3.651 |

Example 3

Predicting ASD with Multiple Metabolites

Figure 6:
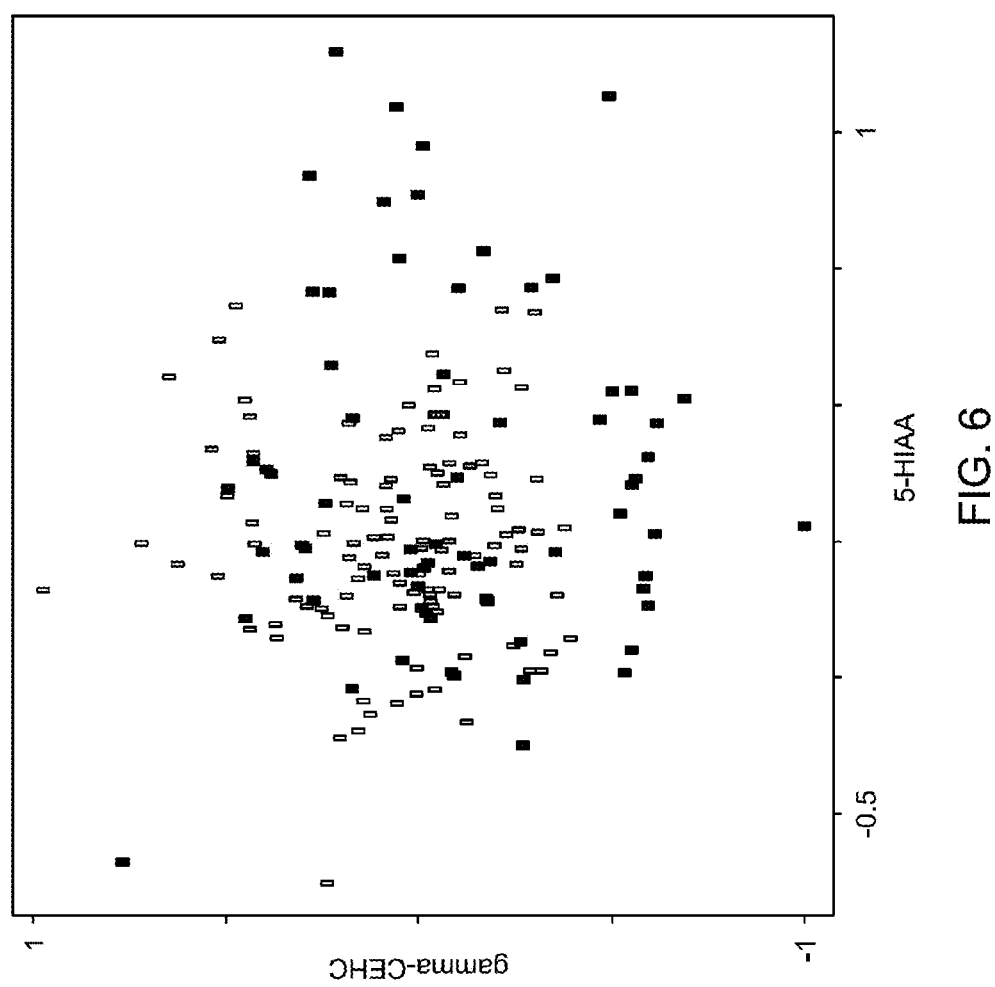
FIG. 6 illustrates the correlation of two exemplary metabolites and demonstrates that these two metabolites possess distinct profiles of tail effects and are complementary.

The information provided by multiple metabolites (e.g., those listed in Table 1) can be used individually or as a group to assist in disease risk prediction. Particularly informative sets of metabolites include members that do not correlate to each other well and have low collinearity (i.e. low mutuality). For example, FIG. 6 shows 5HIAA levels compared against gamma-CEHC levels demonstrating a lack of correlation between informative levels of the two metabolites. For example, the ASD individuals identified in the tail of 5HIAA (FIG. 3) are generally not the same ASD individuals identified in the tail of gamma-CEHC. Thus, the metabolites 5HIAA and gamma-CEHC are deemed to provide complementary information. Tail enriched metabolites with low mutuality provide complementary classification information.

Figure 7:
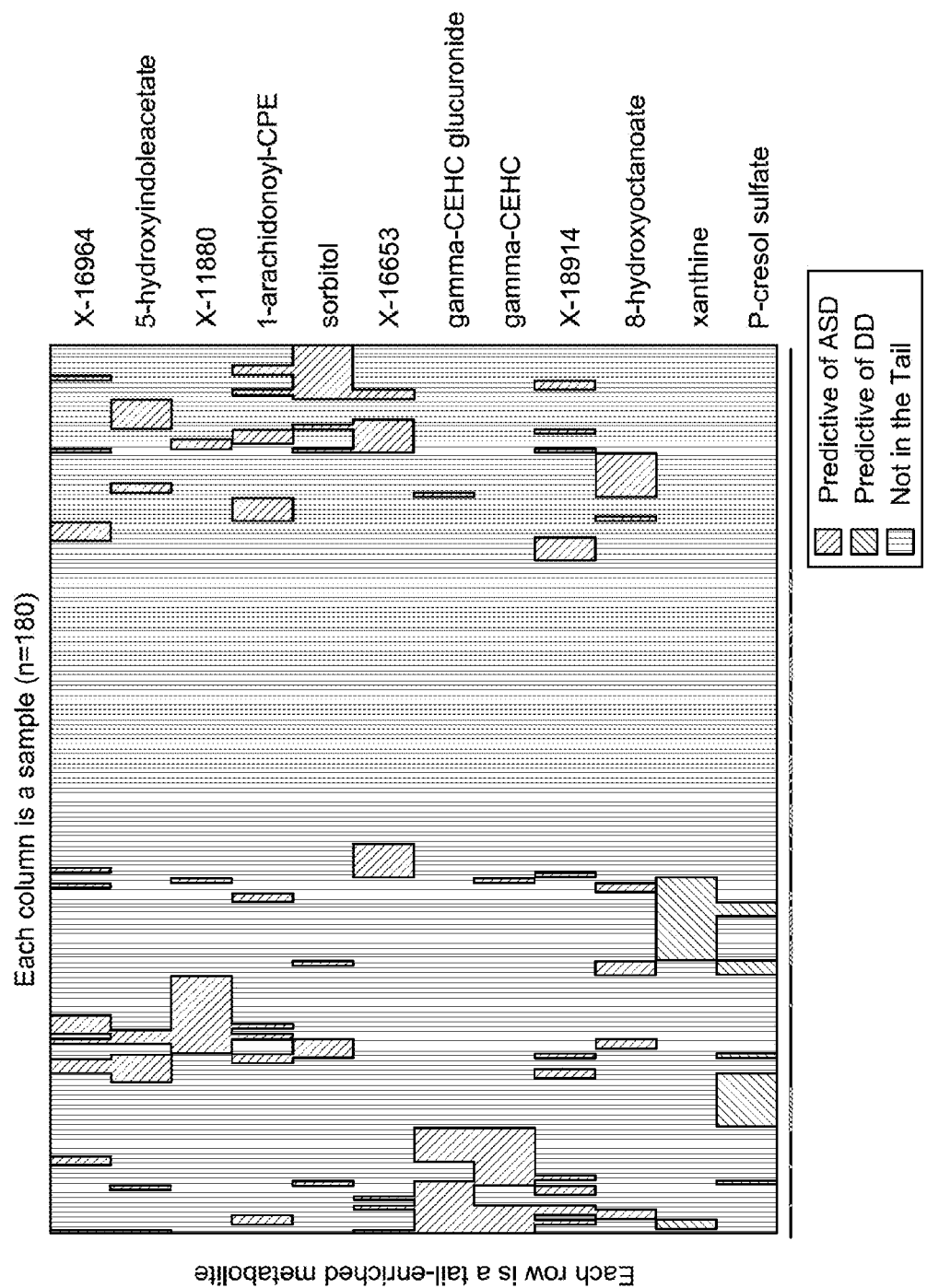
FIG. 7 illustrates the tail effects of 12 exemplary metabolites in 180 subjects, and their predictive power for ASD and DD.

FIG. 7 is a chart indicating, for each of the 180 samples, whether the sample was within a tail or not within a tail of each of the metabolites of a 12-metabolite panel. In this exemplary panel, tails for two metabolites, xanthine and P-cresol sulfate, are predictive of non-ASD (e.g., DD), while tails for the other ten metabolites are predictive of ASD.

Figure 8A:
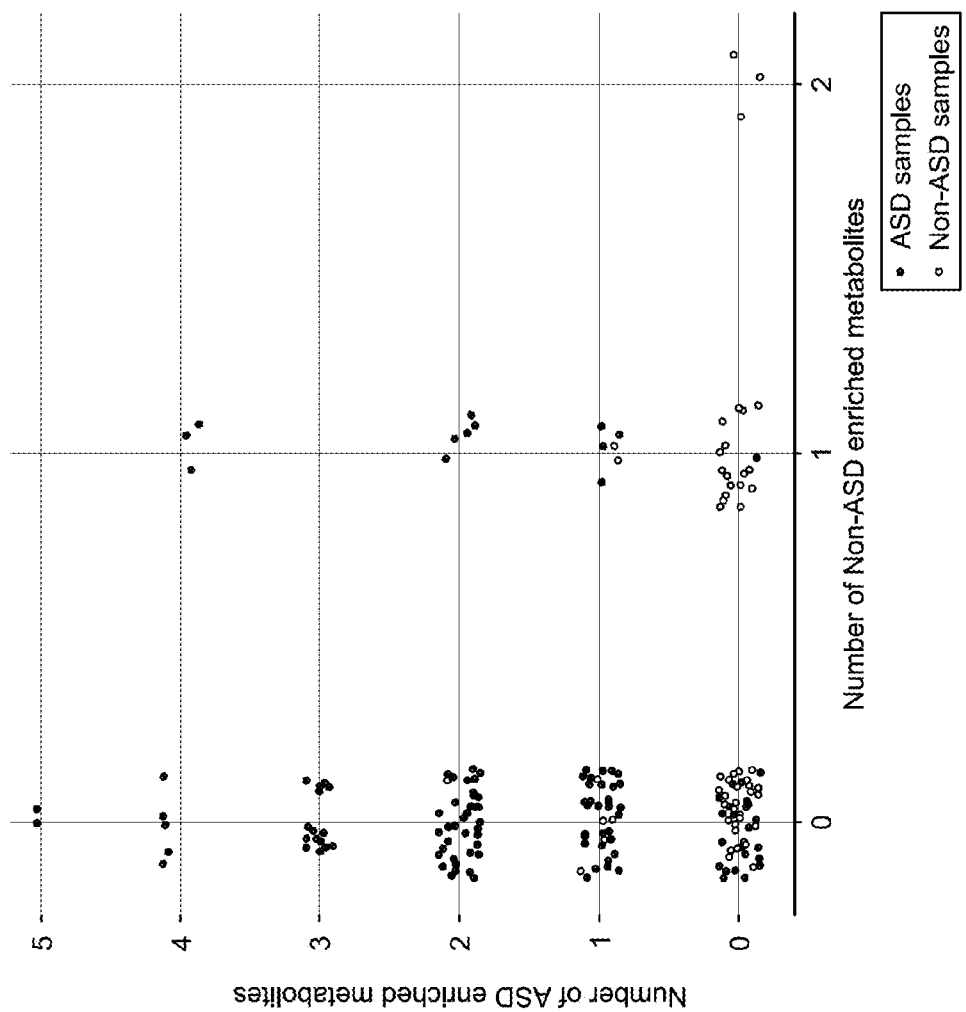
FIG. 8A illustrates a plot of ASD and non-ASD tail effects for 180 samples using an exemplary 12-metabolite panel, demonstrating that samples from ASD patients show aggregation of ASD tail effects.

When multiple metabolites are assessed, the number of combinations of the aggregated tail effect counts increase, as well as the potential aggregated tail effect count. The distribution of aggregated tail effect counts from ASD and from non-ASD populations can be plotted and the resulting distribution can be used to determine suitable separation between ASD and non-ASD when an unknown sample is measured. As shown in FIG. 8A, ASD and non-ASD (here, DD) samples can be further analyzed by employing a voting (e.g., binning) scheme to further utilize the complementary information provided by the metabolites for which a tail effect was observed. Data for a total of 12 metabolites are shown. In one particular scheme, for a given sample, the number of metabolites for which the sample fell within an ASD-predictive tail was summed, as was the number of metabolites for which the sample fell within a non-ASD (here, DD)-predictive tail. These two values are shown plotted as x- and y-coordinates (FIG. 8A). Notably, as the number of ASD enriched metabolites increase (higher in y-axis) and as the number of non-ASD enriched metabolites decrease (lower in x-axis), there appeared to be less mixing of non-ASD dots among ASD dots, e.g., suggesting a lower likelihood for a false positive diagnosis for ASD. On the other hand, as the number of ASD enriched metabolites decreased (lower in y-axis) and as the number of non-ASD enriched metabolites increased (higher in x-axis), there was less mixing of ASD dots among non-ASD dots, e.g., suggesting a lower likelihood for a false positive diagnosis of DD.

The samples were divided into four different bins, shown in FIG. 8B. The bins on the top and on the bottom right in particular showed clear separation, facilitative of ASD or DD risk evaluation.

Of the four bins shown in FIG. 8, the bin most strongly predictive of ASD included samples having 2 or more ASD-enriched features and either 0 or 1 non-ASD enriched features. The bin having 1 ASD-enriched feature and either 0 or 1 non-ASD enriched features was also predictive of ASD, though less strongly than the bin above. The bin having 1 or more non-ASD enriched features and 0 ASD-enriched feature was strongly predictive of non-ASD. A bin of samples having no ASD-enriched features and no non-ASD-enriched features may also provide predictive information in some circumstances.

In one exemplary voting scheme, votes are tallied for a given sample, for example, with ASD-enriched metabolites scoring a point and non-ASD-enriched metabolites subtracting a point. A sample with a positive result (e.g., equal to or greater than 1) may be considered ASD (or having significant risk of ASD), a sample with a negative result (equal to or less than −1) may be considered non-ASD (or having a significant likelihood of non-ASD). A sample with a zero result may be considered likely non-ASD or ASD, depending on the distribution of ASD to non-ASD in the samples, or may be returned as an indeterminate or "no classification result" sample. Similarly, FIG. 8C shows vote tallying results for the 21-metabolite panel described in Table 1.

Figure 21:
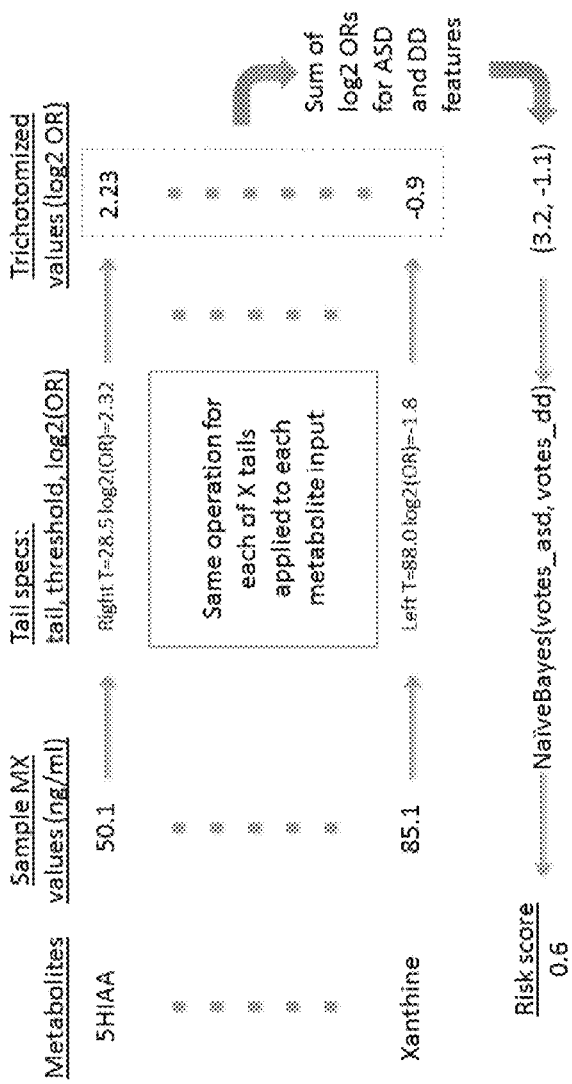
FIG. 21 illustrates a scoring system in which a risk score for ASD or DD is calculated based on the sum of the log 2 values of odds ratios for ASD and DD predictive metabolites.

In another exemplary scoring system (shown in FIG. 21), the log 2 value of the odds ratio (log 2 OR) for ASD and DD features are summed for each metabolite to calculate a risk score for ASD or DD.

Tail effect information may be used to differentiate a subject having ASD or a non-ASD condition. Likewise, tail effect information may be used to predict the risk for another disease or condition, e.g., DD, for a subject.

Figure 8C:
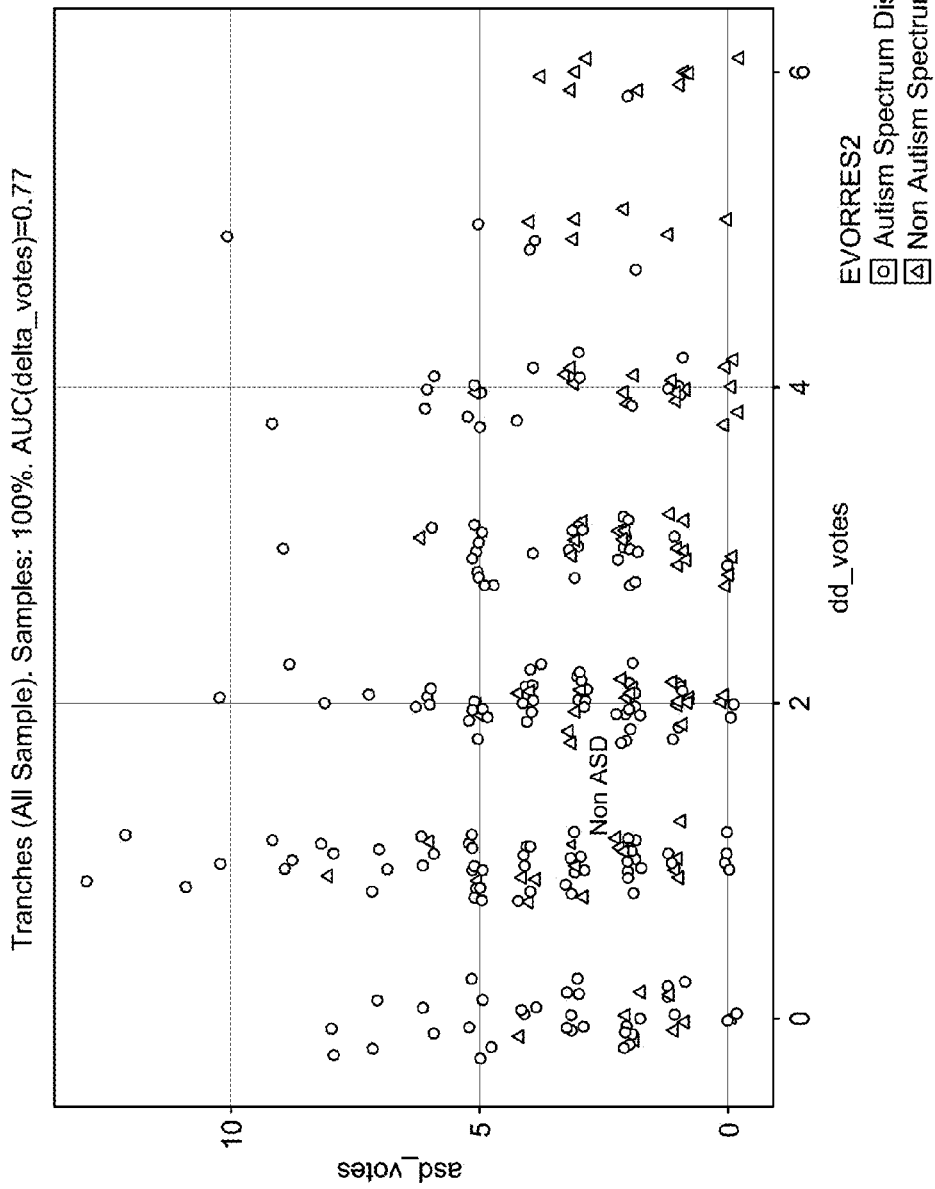
FIG. 8C illustrates a plot of ASD and non-ASD tail effects for 180 samples using an exemplary 21-metabolite panel, demonstrating that samples from ASD patients show aggregation of ASD tail effects.

For example, tail effect distribution for a non-ASD population, e.g, DD, as shown in FIGS. 8A and 8C, can be used to establish a reference value for the average tail effect sum for a given number of metabolites in that population. This average value can be used as a reference to compare to the sum of average tail effects from a sample from an unknown subject, and can be used to assess the subject's risk for ASD without having to obtain the population distribution curves of metabolites in both ASD and non-ASD populations.

Tail effect information, e.g., as described in the above exemplary voting schemes, or similar schemes, may also be combined with traditional mean-shift information and/or other classification information for improved classification results.

Figure 9:
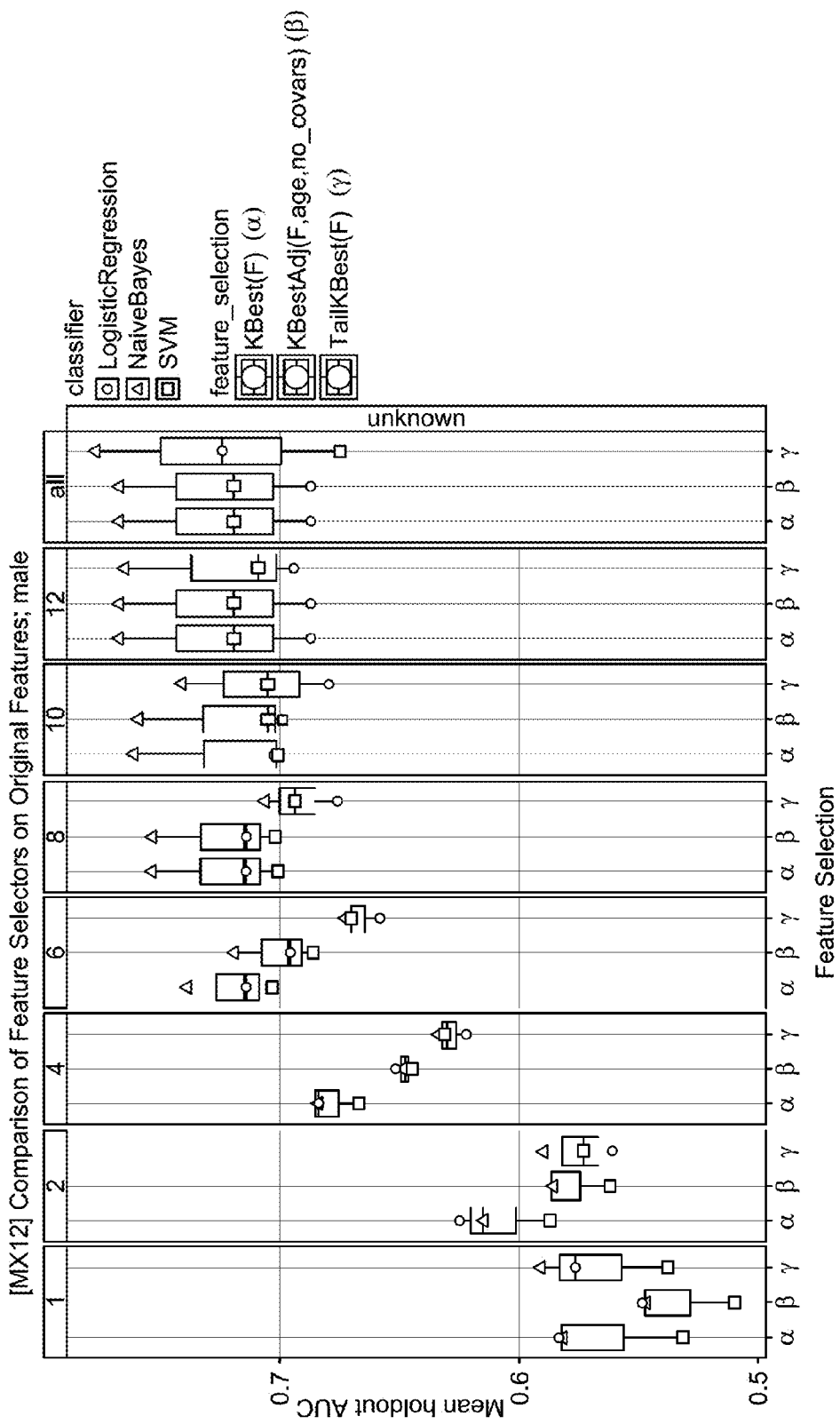
FIG. 9 illustrates increases in the predictability of ASD for an exemplary 12-metabolite panel as the number of metabolites assessed increases.
Figure 10A:
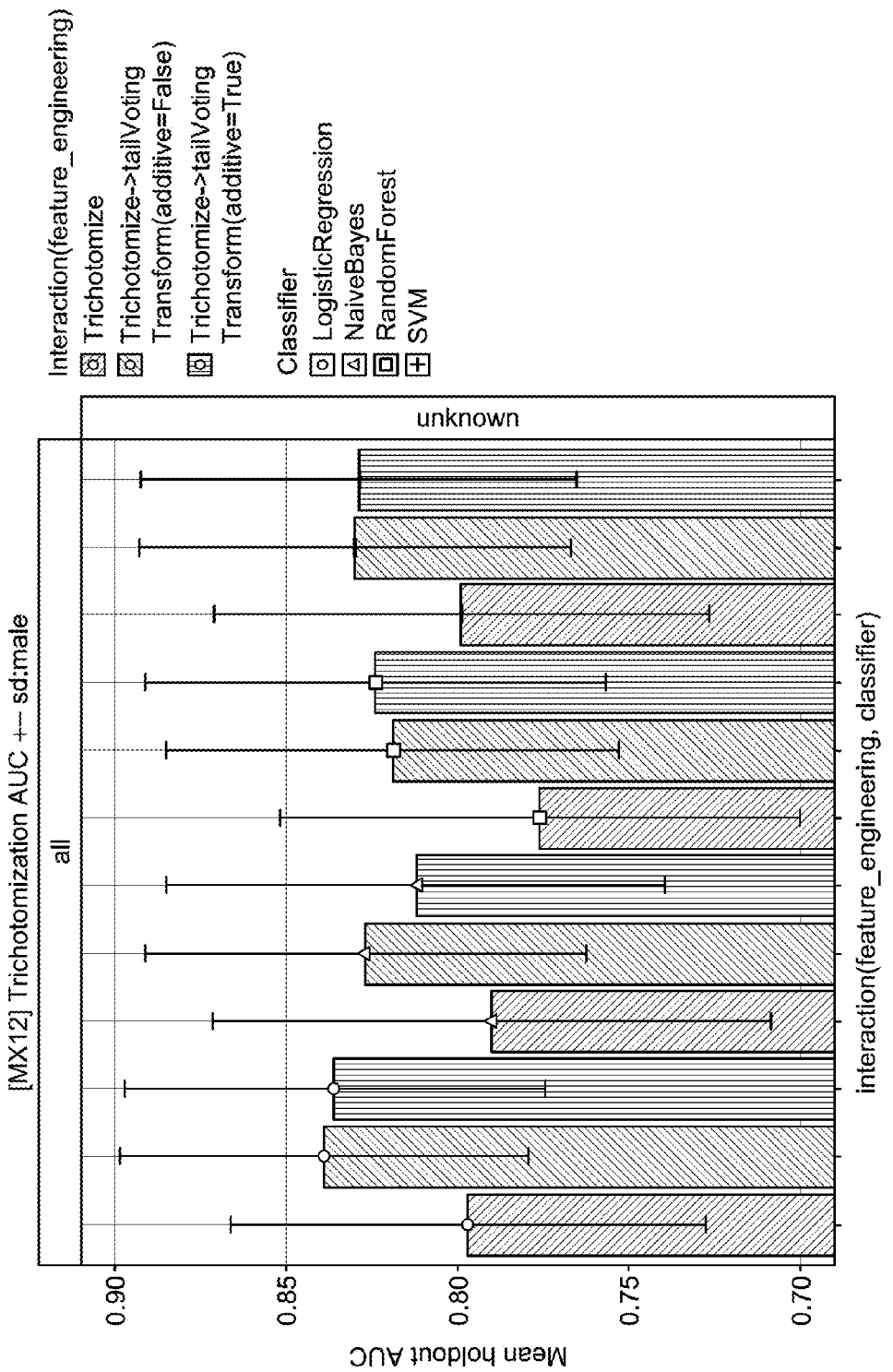
FIG. 10A illustrates the effects of trichotomization on the predictability of ASD using an exemplary 12-metabolite panel.
Figure 10B:
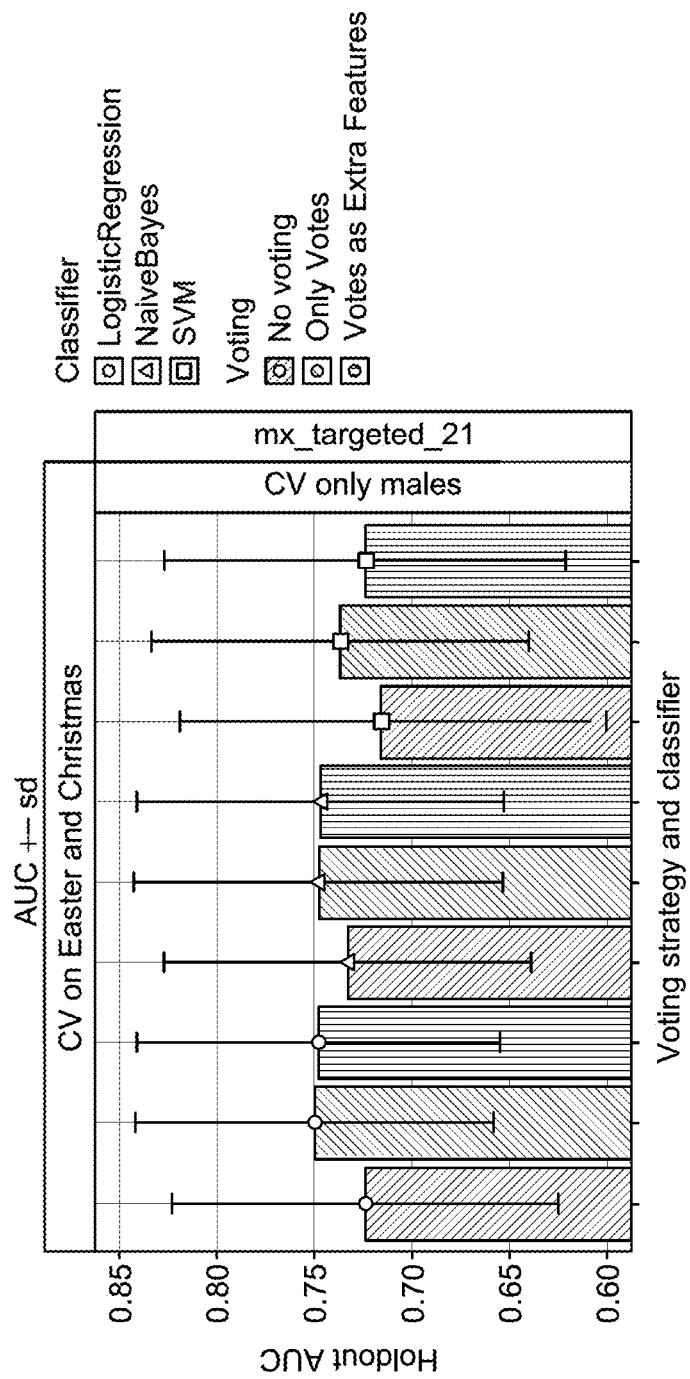
FIG. 10B illustrates the effects of trichotomization on the predictability of ASD in the analysis of an exemplary 21-metabolite panel.
Figure 11A:
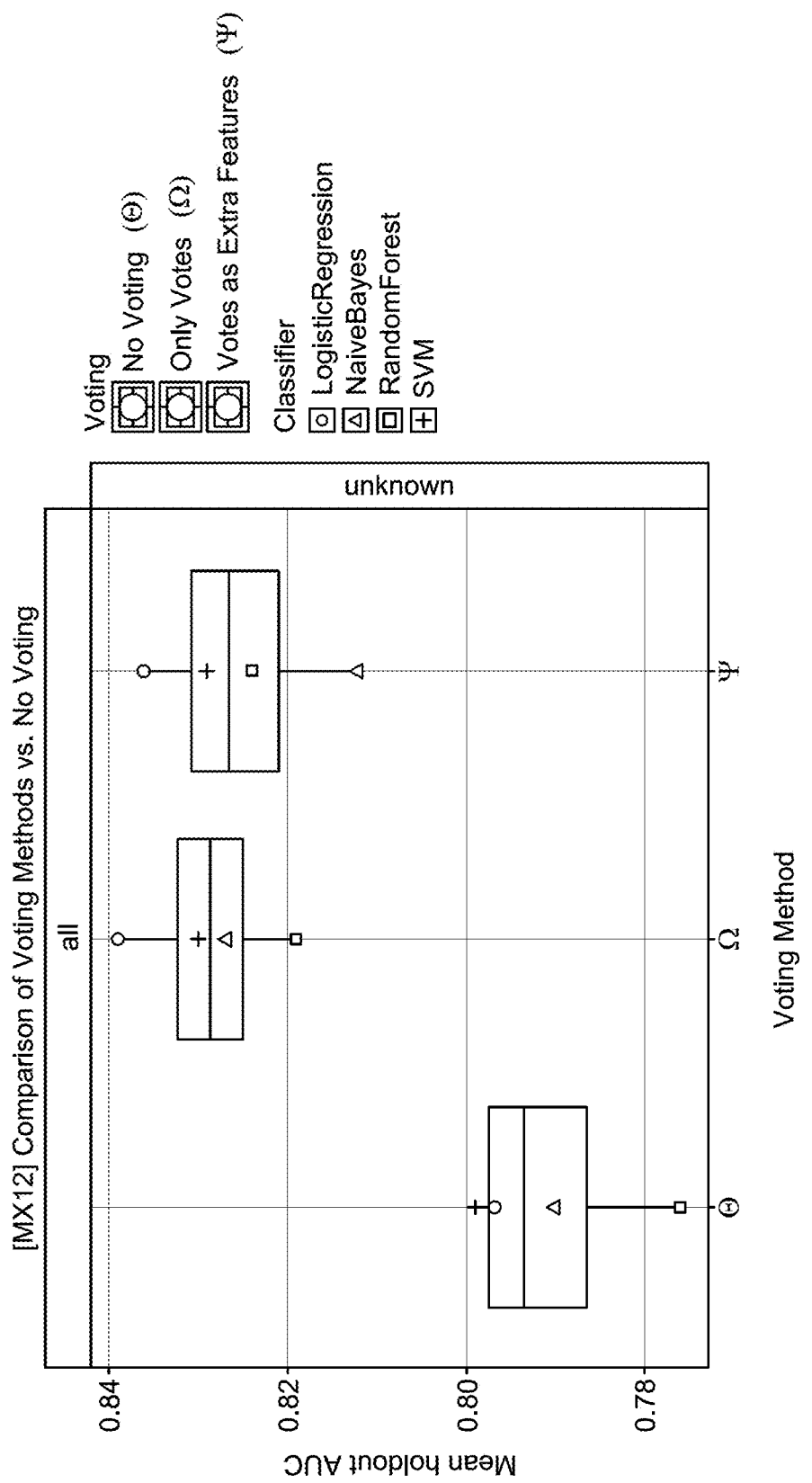
FIG. 11A illustrates an improvement in the predictability of ASD using voting methods compared to a non-voting method for analysis of an exemplary 12-metabolite panel.
Figure 11B:
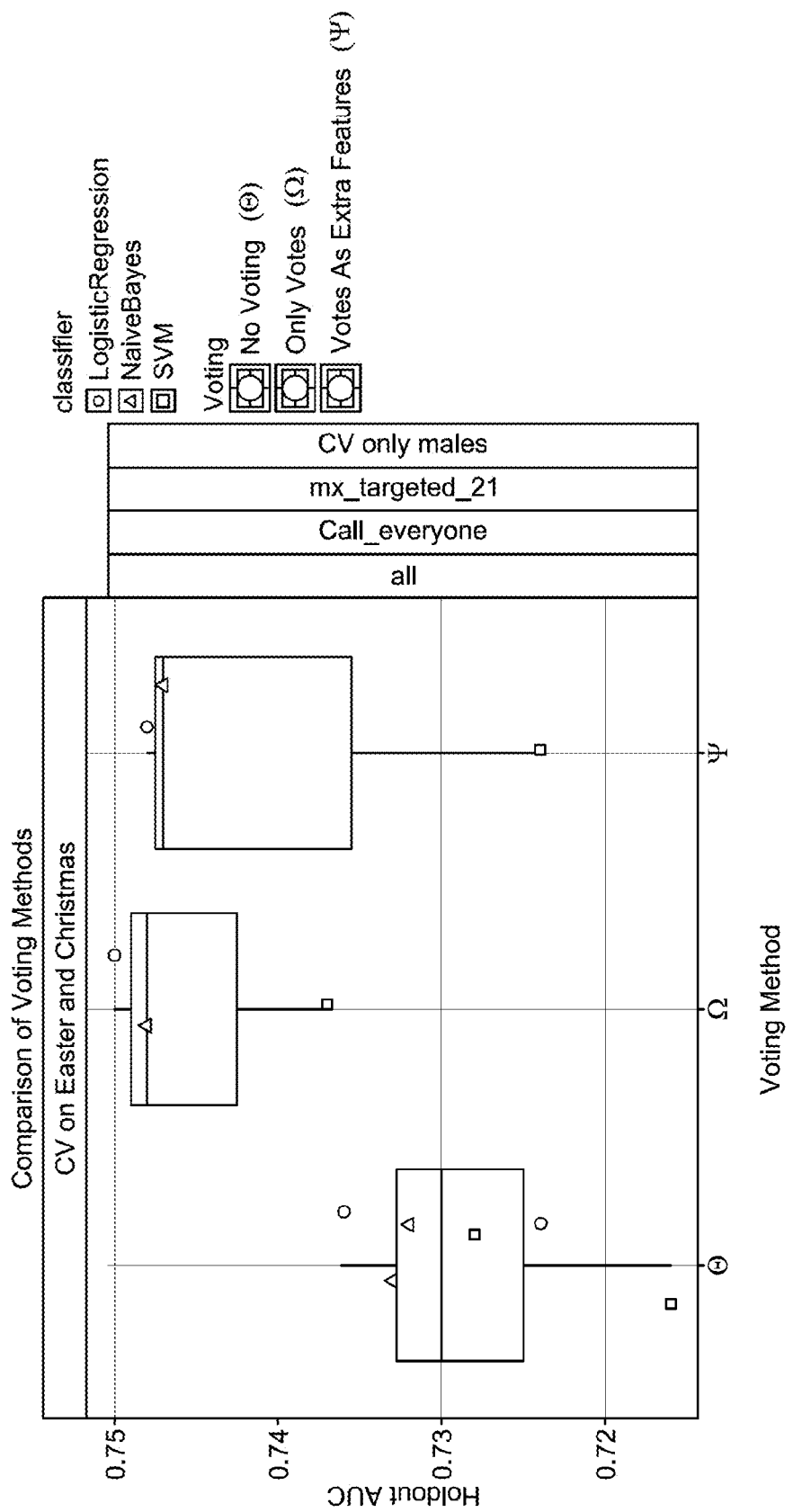
FIG. 11B illustrates an improvement in the predictability of ASD using voting method compared to non-voting method using an exemplary 21-metabolite panel.
Figure 12:
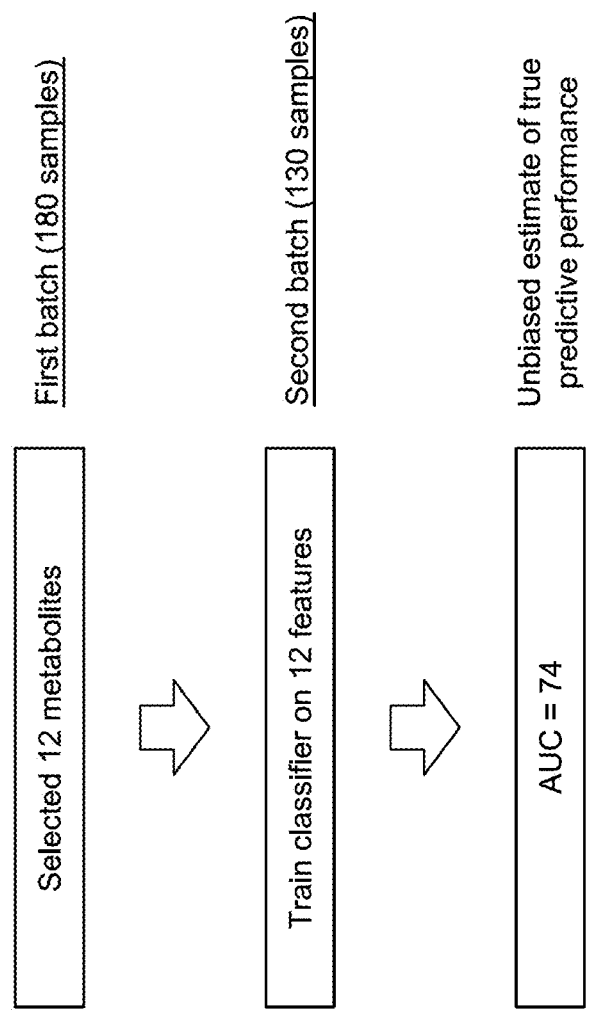
FIG. 12 illustrates the validation process for using an exemplary 12-metabolite panel to achieve a high predictability of ASD.

It is demonstrated herein that the predictability of ASD risk can be increased by analysis of combinations of certain metabolites. For example, FIGS. 9-11, and 13-14A-D illustrate how use of a voting scheme can increase AUC of the classifier and improve predictive ability. Use of subsets of a 12-metabolite panel increased ASD predictive power (y-axis) as the number of metabolites in the subsets increased (from 1 to 12) (FIG. 9). Use of different classifiers (i.e., logistic regression, naive Bayes, or support vector machine (SVM)), and selection of different featured also affect the AUC (FIG. 9). FIG. 10A shows for the same population, using a 12-metabolite panel, the trichotomized prediction of ASD risk using different features and classifiers, while FIG. 10B shows the results using a 21-metabolite panel. FIGS. 11A and 11B show the improvements in ASD risk prediction using voting schemes of the 12-metabolite panel (FIG. 11A) and the 21-metabolite panel (FIG. 11B). Together, these analyses demonstrate that by selecting targeted metabolites and using appropriate statistical tools, a high degree of confidence for ASD risk assessment can be achieved. For example, as shown in FIG. 12, an AUC of at least 0.74 was obtained following the methods described above using 12 metabolites.

Example 4

Selection of High Impact Metabolites from Metabolomics Data

Samples from ASD and DD subjects were screened for detection of approximately 600 known metabolites (shown in Table 3). From the initial set of 600, 84 candidate metabolites were identified to exhibit a tail effect. A subset of the 84 metabolites detected in the samples were elucidated and are identified by name in Table 4. Metabolite panels (e.g., 12 and 21-panels) were selected from the set of 84 candidate metabolites based on a high individual metabolite AUCs. Certain candidate metabolites were excluded from panels based on factors such as an association with medication or age.

TABLE 3

Four hundred sixty five (465) elucidated metabolites of the
initial set of 600 metabolites assayed

| | | |
|---|---|---|
| glycine | N-acetylglycine | sarcosine (N-Methylglycine) |
| serine | N-acetylserine | threonine |
| N-acetylalanine | aspartate | asparagine |
| glutamine | N-acetylglutamate | N-acetyl-aspartyl-glutamate (NAAG) |
| N-acetylhistidine | 1-methylhistidine | 3-methylhistidine |
| imidazole lactate | lysine | N6-acetyllysine |
| glutarate (pentanedioate) | glutaroylcarnitine (C5) | 3-methylglutarylcarnitine-1 |
| phenylalanine | N-acetylphenylalanine | phenylpyruvate |
| phenylacetylglutamine | tyrosine | N-acetyltyrosine |
| phenol sulfate | p-cresol sulfate | o-cresol sulfate |
| 3-methoxytyramine sulfate | 3-(3-hydroxyphenyl)propionate | 3-phenylpropionate (hydrocinnamate) |
| tryptophan | N-acetyltryptophan | indolelactate |
| 3-indoxyl sulfate | kynurenine | kynurenate |
| indoleacetylglutamine | tryptophan betaine | C-glycosyltryptophan |
| N-acetylleucine | 4-methyl-2-oxopentanoate | isovalerate (C5) |
| beta-hydroxyisovalerate | hydroxyisovaleroylcarnitine (C5) | alpha-hydroxyisovalerate |
| 3-methyl-2-oxovalerate | 2-methylbutyroylcarnitine (C5) | tiglyl carnitine (C5) |
| valine | N-acetylvaline | 3-methyl-2-oxobutyrate |
| 3-hydroxyisobutyrate | alpha-hydroxyisocaproate | methionine |
| S-adenosylhomocysteine (SAH) | alpha-ketobutyrate | 2-aminobutyrate |
| S-methylcysteine | taurine | arginine |
| proline | citrulline | homoarginine |
| N-delta-acetylornithine | N-methyl proline | hydroxyproline |
| creatinine | acisoga | 5-methylthioadenosine (MTA) |
| 4-guanidinobutanoate | glutathione, oxidized (GSSG) | cys-gly, oxidized |
| gamma-glutamylisoleucine | gamma-glutamylleucine | gamma-glutamylmethionine |
| gamma-glutamyltyrosine | gamma-glutamylvaline | N-acetylcarnosine |
| cyclo(gly-pro) | cyclo(leu-pro) | cyclo(L-phe-L-pro) |
| isoleucylglutamine | isoleucylglycine | isoleucylvaline |
| leucylglutamate | leucylglycine | leucylphenylalanine |

TABLE 3-continued

Four hundred sixty five (465) elucidated metabolites of the
initial set of 600 metabolites assayed

| | | |
|---|---|---|
| phenylalanylalanine | phenylalanylarginine | phenylalanylaspartate |
| phenylalanylleucine | phenylalanylmethionine | phenylalanylphenylalanine |
| pyroglutamylglycine | pyroglutamylvaline | serylleucine |
| tryptophylphenylalanine | valylglycine | valylleucine |
| glucose | 3-phosphoglycerate | pyruvate |
| ribitol | xylonate | xylose |
| arabitol | sucrose | fructose |
| mannitol | glucuronate | erythronate |
| succinylcarnitine (C4) | succinate | fumarate |
| valerate (5:0) | caproate (6:0) | heptanoate (7:0) |
| caprate (10:0) | laurate (12:0) | 5-dodecenoate (12:1n7) |
| 2-hydroxyglutarate | suberate (octanedioate) | azelate (nonanedioate; C9) |
| dodecanedioate (C12) | tetradecanedioate (C14) | hexadecanedioate (C16) |
| 3-carboxy-4-methyl-5-propyl-2-furanpropanoate (CMPF) | 2-aminoheptanoate | 2-aminooctanoate |
| propionylcarnitine (C3) | propionylglycine (C3) | N-octanoylglycine |
| hydroxybutyrylcarnitine | valerylcarnitine (C5) | hexanoylcarnitine (C6) |
| cis-4-decenoyl carnitine | laurylcarnitine (C12) | myristoylcarnitine |
| linoleoylcarnitine | oleoylcarnitine (C18) | deoxycarnitine |
| 3-hydroxybutyrate (BHBA) | alpha-hydroxycaproate | 2-hydroxyoctanoate |
| 2-hydroxystearate | 3-hydroxypropanoate | 3-hydroxyoctanoate |
| 5-hydroxyhexanoate | 8-hydroxyoctanoate | 16-hydroxypalmitate |
| oleic ethanolamide | palmitoyl ethanolamide | N-oleoyltaurine |
| myo-inositol | scyllo-inositol | choline |
| 1-myristoyl-GPC (14:0) | 2-myristoyl-GPC (14:0) | 1-pentadecanoylglycerophosphocholine (15:0) |
| 1-palmitoleoyl-GPC (16:1) | 2-palmitoleoyl-GPC (16:1) | 1-heptadecanoyl-GPC (17:0) |
| 1-oleoyl-GPC (18:1) | 2-oleoyl-GPC (18:1) | 1-linoleoyl-GPC (18:2) |
| 1-nonadecanoylglycerophosphocholine (19:0) | 1-eicosadienoyl-GPC (20:2) | 1-arachidoyl-GPC (20:0) |
| 2-eicosatrienoyl-GPC (20:3) | 1-arachidonoyl-GPC (20:4) | 2-arachidonoyl-GPC (20:4) |
| 1-docosapentaenoyl-GPC (22:5n6) | 1-docosahexaenoyl-GPC (22:6) | 1-palmitoylplasmenylethanolamine |
| 1-palmitoyl-GPE (16:0) | 2-palmitoyl-GPE (16:0) | 1-stearoyl-GPE (18:0) |
| 2-oleoyl-GPE (18:1) | 1-linoleoyl-GPE (18:2) | 2-linoleoyl-GPE (18:2) |
| 1-eicosatrienoylglycerophosphoethanolamine | 1-docosahexaenoylglycerophosphoethanolamine | 1-palmitoyl-GPI (16:0) |
| 1-linoleoyl-GPI (18:2) | 1-arachidonoyl-GPI (20:4) | 1-arachidonoylglyercophosphate |
| glycerol | glycerol 3-phosphate (G3P) | 1-myristoylglycerol (14:0) |
| 1-oleoylglycerol (18:1) | 1-linoleoylglycerol (18:2) | sphinganine |
| lathosterol | cholesterol | 7-beta-hydroxycholesterol |
| 21-hydroxypregnenolone disulfate | 5alpha-pregnan-3beta,20beta-diol monosulfate 1 | 5alpha-pregnan-3beta,20alpha-diol monsulfate 2 |
| cortisol | corticosterone | cortisone |
| epiandrosterone sulfate | androsterone sulfate | 4-androsten-3alpha,17alpha-diol monosulfate 3 |
| 5alpha-androstan-3beta,17beta-diol disulfate | cholate | glycocholate |
| taurochenodeoxycholate | tauro-beta-muricholate | deoxycholate |
| ursodeoxycholate | glycoursodeoxycholate | tauroursodeoxycholate |
| glycocholenate sulfate | taurocholenate sulfate | 7-ketodeoxycholate |
| xanthine | xanthosine | urate |
| AMP | adenosine 3',5'-cyclic monophosphate (cAMP) | adenosine |
| N6-methyladenosine | N6-carbamoylthreonyladenosine | guanosine |
| N2,N2-dimethylguanosine | uridine | pseudouridine |
| 3-ureidopropionate | beta-alanine | N-acetyl-beta-alanine |
| 5,6-dihydrothymine | 3-aminoisobutyrate | nicotinamide |
| N1-Methyl-2-pyridone-5-carboxamide | adenosine 5'-diphosphoribose (ADP-ribose) | riboflavin (Vitamin B2) |
| threonate | arabonate | alpha-tocopherol |
| gamma-CEHC glucuronide | heme | bilirubin |
| pyridoxate | hippurate | 2-hydroxyhippurate (salicylurate) |
| benzoate | catechol sulfate | O-methylcatechol sulfate |
| 4-methylcatechol sulfate | 4-ethylphenyl sulfate | 4-vinylphenol sulfate |
| theobromine | theophylline | 1-methylurate |
| 7-methylxanthine | 2-piperidinone | levulinate (4-oxovalerate) |
| gluconate | cinnamoylglycine | dihydroferulic acid |
| methyl indole-3-acetate | N-(2-furoyl)glycine | piperine |
| 4-allylphenol sulfate | methyl glucopyranoside (alpha + beta) | tartronate (hydroxymalonate) |
| 6-oxopiperidine-2-carboxylic acid | hydroquinone sulfate | salicylate |
| O-sulfo-L-tyrosine | 2-aminophenol sulfate | 2-ethylhexanoic acid |
| EDTA | glycerol 2-phosphate | glycolate (hydroxyacetate) |
| pyroglutamylglutamine | betaine | phenylalanylglycine |
| threonylleucine | alanine | phenylalanyltryptophan |
| 1,5-anhydroglucitol (1,5-AG) | glutamate | serylphenylalanine |
| glycerate | histidine | valylvaline |
| threitol | imidazole propionate | lactate |
| mannose | 2-aminoadipate | arabinose |
| alpha-ketoglutarate | pipecolate | sorbitol |
| phosphate | 4-hydroxyphenylacetate | citrate |
| pelargonate (9:0) | 3-(4-hydroxyphenyl)lactate (HPLA) | malate |
| 17-methylstearate | 3-methoxytyrosine | caprylate (8:0) |
| undecanedioate | 2-hydroxyphenylacetate | methylpalmitate (15 or 2) |
| docosadioate | indolepropionate | sebacate (decanedioate) |
| butyrylcarnitine (C4) | 5-hydroxyindoleacetate | octadecanedioate (C18) |

TABLE 3-continued

Four hundred sixty five (465) elucidated metabolites of the initial set of 600 metabolites assayed

| | | |
|---|---|---|
| acetylcarnitine (C2) | leucine | 2-methylmalonyl carnitine |
| decanoylcarnitine (C10) | isovalerylcarnitine (C5) | N-palmitoyl glycine |
| stearoylcarnitine (C18) | N-acetylisoleucine | octanoylcarnitine (C8) |
| acetoacetate | 3-hydroxy-2-ethylpropionate | palmitoylcarnitine (C16) |
| 2-hydroxypalmitate | isobutyrylglycine (C4) | carnitine |
| 3-hydroxysebacate | N-formylmethionine | 2-hydroxydecanoate |
| 12,13-DiHOME | cysteine | 3-hydroxydecanoate |
| N-palmitoyltaurine | ornithine | 13-HODE + 9-HODE |
| ethanolamine | N-acetylarginine | N-stearoyltaurine |
| 2-palmitoyl-GPC (16:0) | creatine | glycerophosphorylcholine (GPC) |
| 2-stearoyl-GPC (18:0) | 4-acetamidobutanoate | 1-palmitoyl-GPC (16:0) |
| 1-linolenoylglycerophosphocholine (18:3n3) | gamma-glutamylalanine | 1-stearoyl-GPC (18:0) |
| 1-eicosatrienoyl-GPC (20:3) | gamma-glutamyltryptophan | 2-linoleoyl-GPC (18:2) |
| 1-docosapentaenoyl-GPC (22:5n3) | asparagylleucine | 1- eicosenoylglycerophosphocholine (20:1n9) |
| 1-oleoylplasmenylethanolamine | isoleucylalanine | 1- eicosapentaenoylglycerophosphocholine (20:5n3) |
| 1-oleoyl-GPE (18:1) | leucylaspartate | 1-stearoylplasmenylethanolamine |
| 2-arachidonoyl-GPE (20:4) | methionylalanine | 2- stearoylglycerophosphoethanolamine |
| 1-oleoyl-GPI (18:1) | phenylalanylisoleucine | 1-arachidonoyl-GPE (20:4) |
| 1-oleoylglycerophosphoglycerol | dimethylglycine | 1-stearoyl-GPI (18:0) |
| 1-stearoylglycerol (18:0) | N-acetylthreonine | 1-palmitoylglycerophosphoglycerol |
| sphingosine | N-acetylaspartate (NAA) | 1-palmitoylglycerol (16:0) |
| pregnenolone sulfate | pyroglutamine | sphingosine 1-phosphate |
| 5alpha-pregnan-3(alpha or beta),20beta-diol disulfate | trans-urocanate | 7-HOCA |
| 16a-hydroxy DHEA 3-sulfate | N-6-trimethyllysine | 5alpha-pregnan-3beta,20alpha-diol disulfate |
| 4-androsten-3beta,17beta-diol disulfate 2 | 3-methylglutarylcarnitine-2 | dehydroisoandrosterone sulfate (DHEA-S) |
| glycochenodeoxycholate | phenyllactate (PLA) | 4-androsten-3beta,17beta-diol disulfate 1 |
| taurolithocholate 3-sulfate | 4-hydroxyphenylpyruvate | taurocholate |
| glycohyocholate | vanillylmandelate (VMA) | glycolithocholate sulfate |
| hypoxanthine | p-toluic acid | hyocholate |
| ADP | indoleacetate | inosine |
| 1-methyladenosine | xanthurenate | allantoin |
| 1-methylguanosine | indole-3-carboxylic acid | adenine |
| 5,6-dihydrouracil | isovalerylglycine | 7-methylguanine |
| N4-acetylcytidine | isoleucine | 5-methyluridine (ribothymidine) |
| trigonelline (N'-methylnicotinate) | 2-hydroxy-3-methylvalerate | cytidine |
| pantothenate (Vitamin B5) | isobutyrylcarnitine (C4) | 1-methylnicotinamide |
| gamma-CEHC | N-acetylmethionine | FAD |
| biliverdin | 2-hydroxybutyrate (AHB) | gamma-tocopherol |
| 4-hydroxyhippurate | urea | bilirubin (E,E) |
| 3-methyl catechol sulfate 2 | dimethylarginine inine (ADMA + SDMA) | 3-hydroxyhippurate |
| paraxanthine | prolylhydroxyproline | 3-methyl catechol sulfate 1 |
| 3-methylxanthine | N-acetylputrescine | caffeine |
| 2-isopropylmalate | 5-oxoproline | 1-methylxanthine |
| homostachydrine | gamma-glutamylphenylalanine | 1,6-anhydroglucose |
| thymol sulfate | alanylleucine | erythritol |
| 4-acetylphenyl sulfate | glycylleucine | stachydrine |
| 2-pyrrolidinone | leucylalanine | 4-acetaminophen sulfate |
| dimethyl sulfone | leucylserine | 1,2-propanediol |
| phenylcarnitine | iminodiacetate (IDA) | 2-hydroxyisobutyrate |

TABLE 4

Identified candidate metabolites exhibiting a tail effect 1-arachidonoyl-GPC (20:4)
1-arachidonoyl-GPE (20:4)
1-docosahexaenoylglycerophosphoethanolamine
1-oleoylplasmenylethanolamine
1-palmitoyl-GPC (16:0)
1-palmitoylglycerol (16:0)
1-palmitoylplasmenylethanolamine
1-stearoylglycerol (18:0)
1,5-anhydroglucitol (1,5-AG)
17-methylstearate
2-hydroxyisobutyrate
2-isopropylmalate
2-pyrrolidinone
3-(3-hydroxyphenyl)propionate
3-carboxy-4-methyl-5-propyl-2-furanpropanoate (CMPF)
3-hydroxyhippurate
3-indoxyl sulfate
4-ethylphenyl sulfate
4-hydroxyphenylpyruvate
5-hydroxyhexanoate
5-hydroxyindoleacetate
8-hydroxyoctanoate
caffeine
caprate (10:0)
dihydroferulic acid
dimethylarginine (ADMA + SDMA)
ethanolamine
gamma-CEHC
gamma-CEHC glucuronide
hexadecanedioate (C16)
homoarginine
hydroxyisovaleroylcarnitine (C5)
indoleacetate
indolelactate
isobutyrylglycine (C4)
isovalerylglycine
lactate

TABLE 4-continued

Identified candidate metabolites exhibiting a tail effect methionylalanine
methylpalmitate (15 or 2)
N-acetylaspartate (NAA)
N-formylmethionine
N1-Methyl-2-pyridone-5-carboxamide
p-cresol sulfate
pantothenate (Vitamin B5)
phenylacetylglutamine
phenylalanylarginine
pipecolate
serine
serylphenylalanine
sorbitol
urea
3,4-methylene-heptanoylcarnitine
sulfated methylparaben
cyclo(prolylproline)
hydroxy-Chlorothalonil
phenylacetylcarnitine
xanthine Two panels of metabolites (a 12-metabolite panel composed of the metabolites of FIG. 7 and a 21 metabolite panel composed of the metabolites of Table 1) were tested for ASD risk prediction. The results show that the 12- and 21-metabolite panels contributed strongly to prediction of ASD. An overview of the effects of including and excluding metabolites of the 12- or 21 panel on ASD prediction is shown in FIGS. 14A-D. Whitelists indicate AUC values of classifiers using the data from the 12- or 21 metabolite panels only, while blacklists indicate AUC values of classifiers excluding the 12- or 21 metabolite panels but using other metabolites, either from the group of 84 candidate metabolites or the full group of 600 metabolites (all_candidates=84 candidate metabolites; all features=600 metabolites). Mean shift (top panel) and tail analysis (bottom panel) were performed. These data show that the predictive information for ASD is attributable to metabolites within the 12- or 21-metabolite panels, whether assessed by mean shift or tail analysis. Thus, the metabolites observed to exhibit strong tail effects (the metabolites on the 12- and 21-metabolite groups) have much greater ASD vs. DD predictive power than the other metabolites from the 600 metabolite panel which do not exhibit strong tail effects.

Figure 14A:
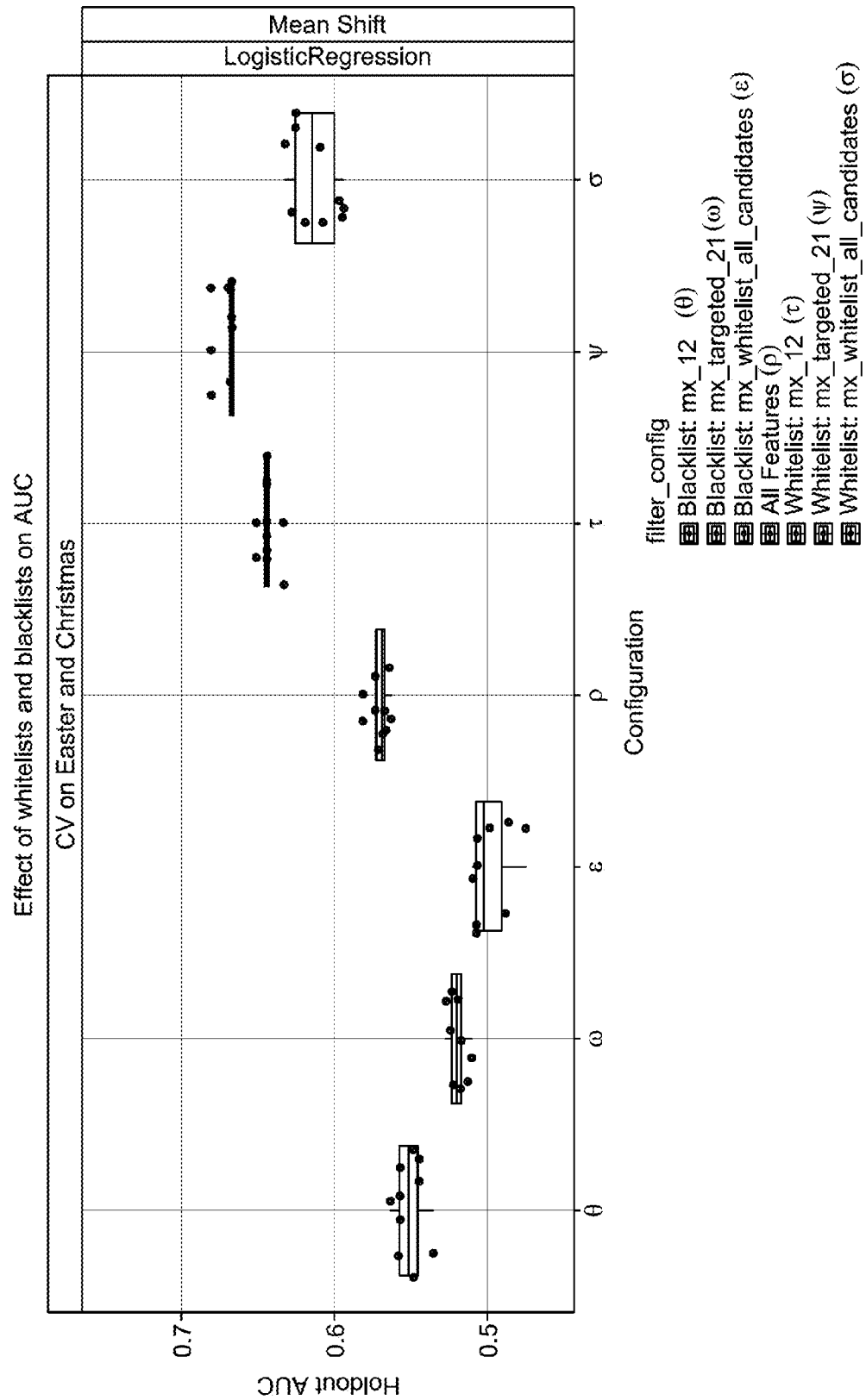
FIGS. 14A-B illustrate the effects on the predictability of ASD by the inclusion and exclusion of an exemplary 12-metabolite panel, an exemplary 21-metabolite panel, and a set of 84 candidate metabolites from a total number of 600 metabolites, as assessed by tail effect analysis and mean shift analysis. (Blacklist=excluded, Whitelist=included, mx_12=exemplary 12-metabolite panel, mx_targeted 21=exemplary 21-metabolite panel, mx_all_candidates=84 candidate metabolites, all features=total set of 600 metabolites)
Figure 14B:
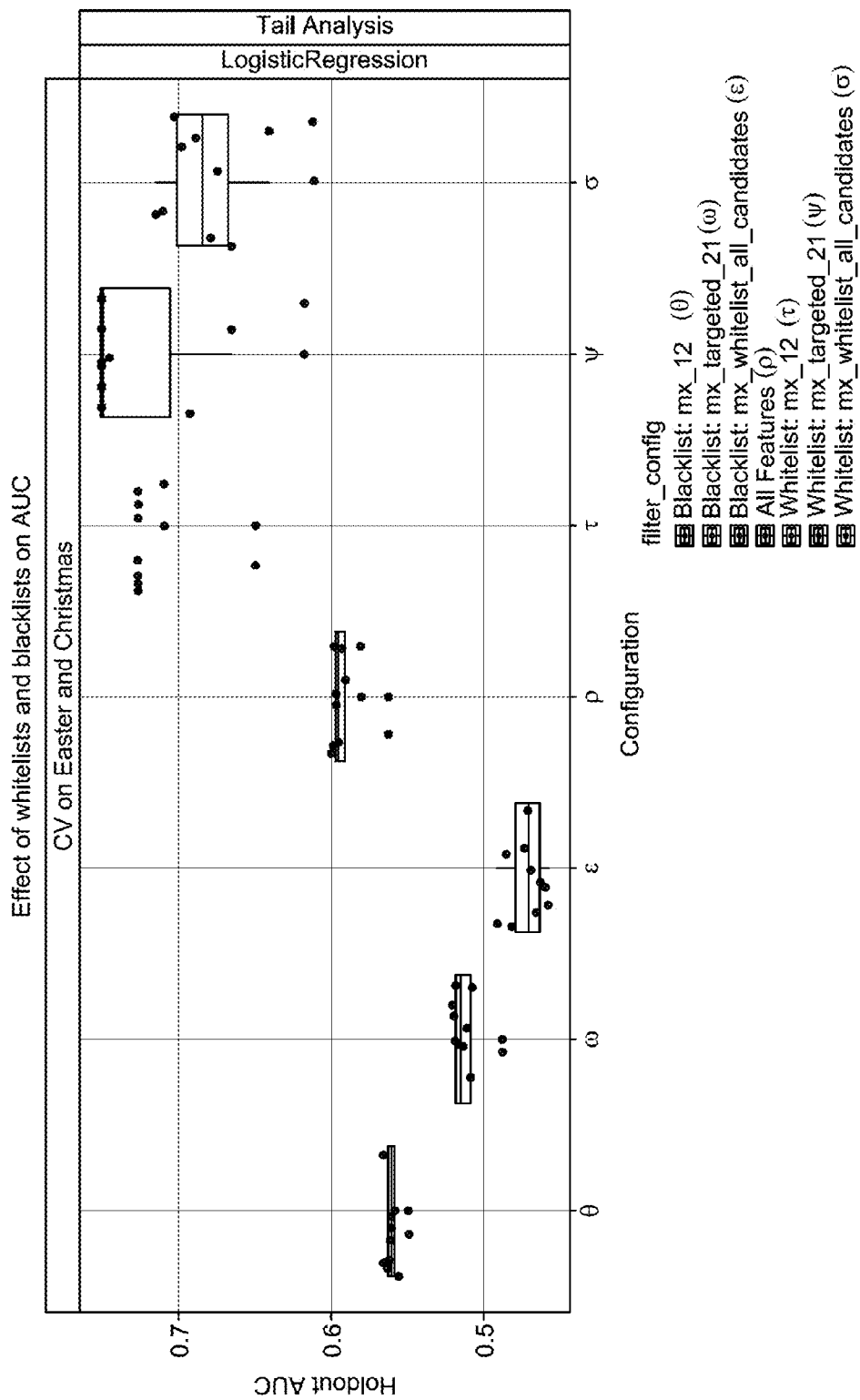
Figure 14C:
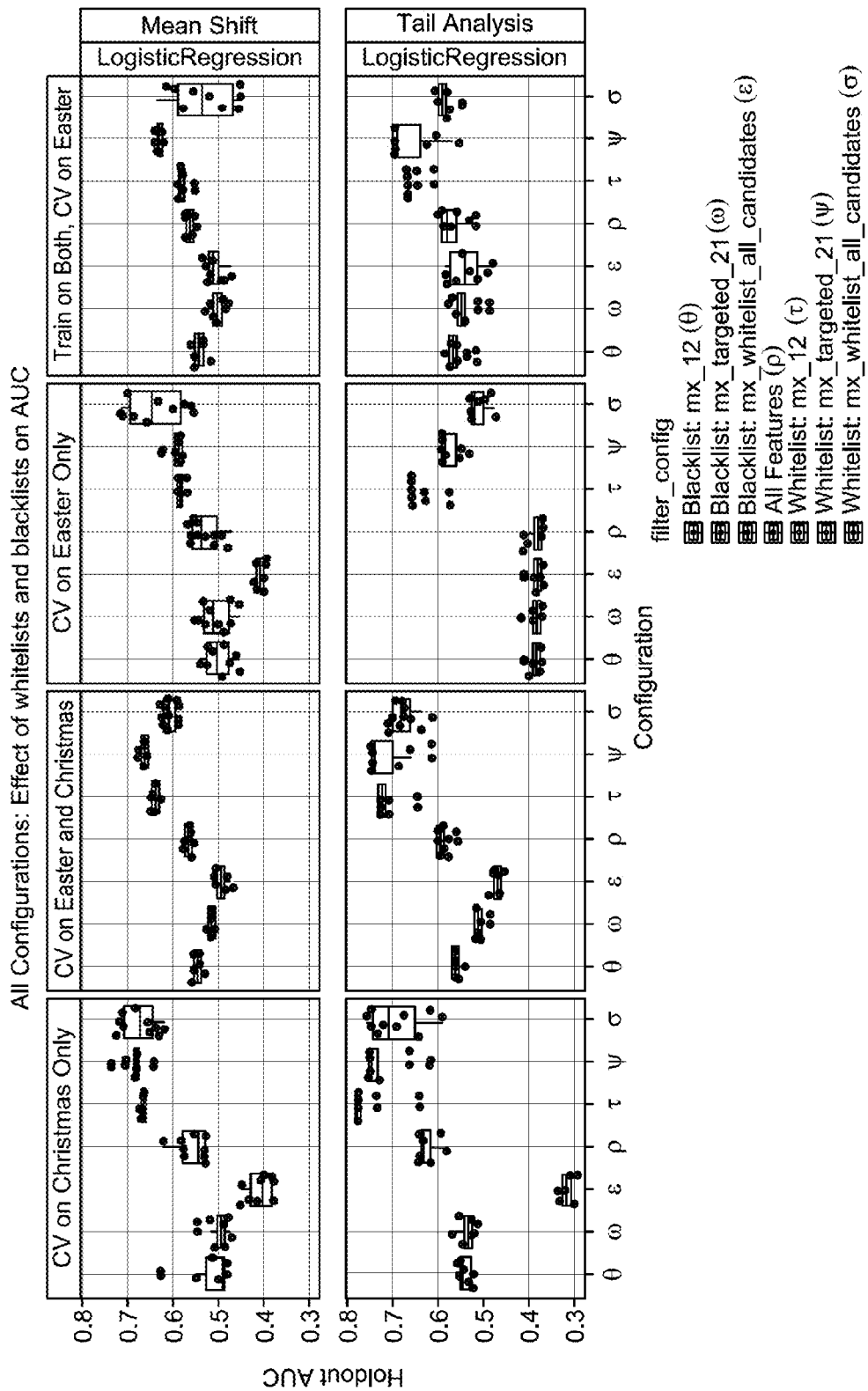
FIGS. 14C-D illustrate the effects on the predictability of ASD by the by the inclusion (whitelists) and exclusion (blacklists) of an exemplary 12-metabolite panel and an exemplary 21-metabolite panel from a total number of 600 metabolites as assessed by tail effect analysis and mean shift analysis, and by comparing logistic regression to Bayes analysis, in two cohorts of samples (i.e., "Christmas" and "Easter"). (Blacklist=excluded, Whitelist=included, mx_12=exemplary 12 metabolite panel, mx_targeted 21=exemplary 21-metabolite panel, mx_all_candidates=84 candidate metabolites, all features=total set of 600 metabolites)
Figure 14D:
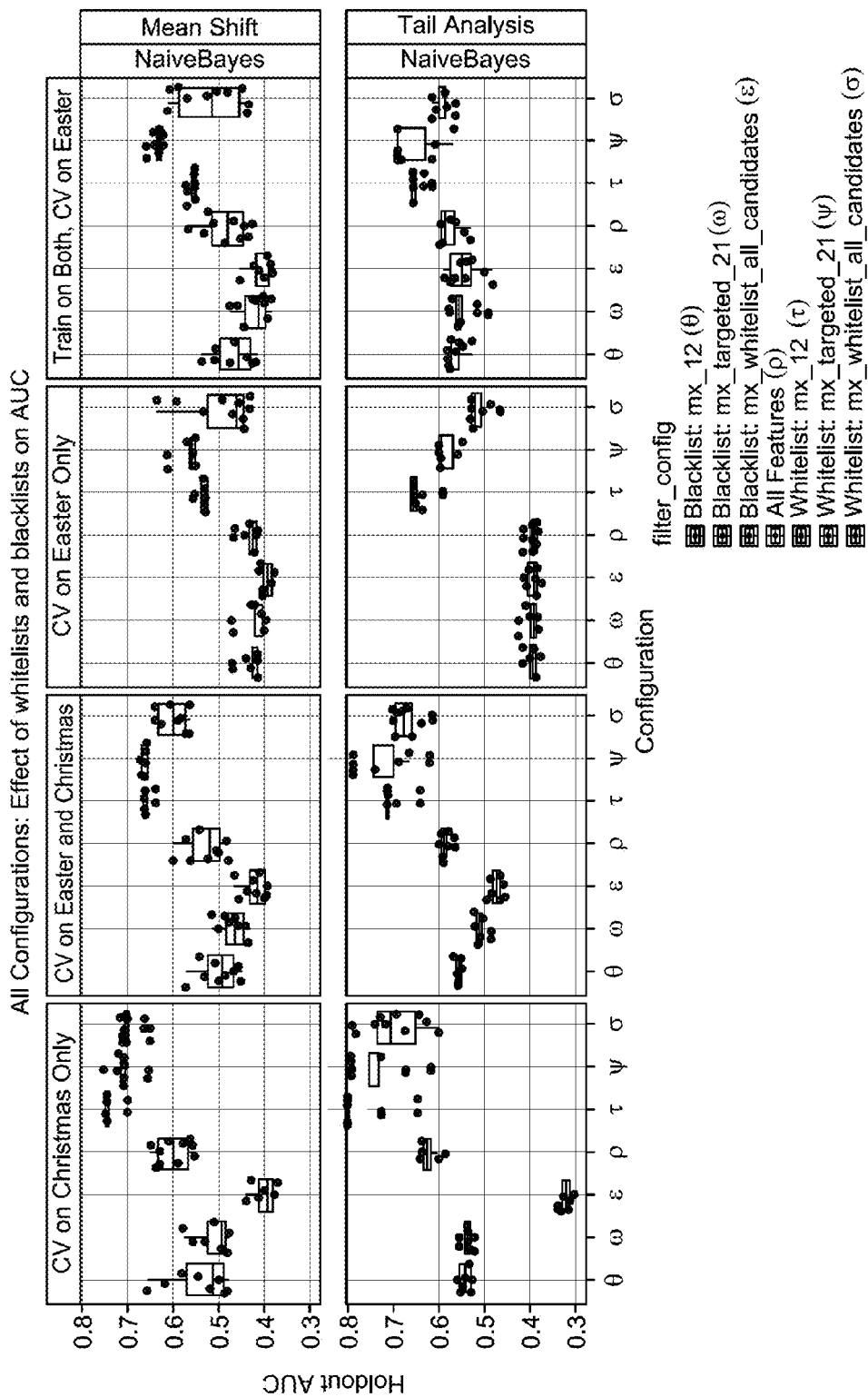

FIGS. 14C-D expands the results from FIGS. 14A-B and include additional analyses using Naive Bayes analysis in addition to logistic regression. In addition, FIG. 14B shows results broken up into different cohorts of samples (i.e., "Christmas" and "Easter"). The far left panel shows AUC results in which the classifier was trained on 192 samples and cross validated on the Christmas cohort only; the middle left panel shows AUC results in which the classifier was trained on 299 samples and cross validated on Christmas and Easter cohorts; the middle right panel shows AUC results in which the classifier was trained on samples from and cross validated on Easter cohorts only; and the far right panel shows AUC results in which the classifier was trained on samples from Christmas and Easter cohorts and cross validated on Easter cohorts. The highest AUCs were achieved using metabolites within the 12- or 21-metabolite panels (e.g., the metabolites exhibiting tail effects).

FIGS. 17A-B, 18A-B and 19A-D further expand the results of FIGS. 14A-D by showing the AUC predictions by including the 12 or 21 metabolite panels (whitelists) and by excluding them (blacklists) according to the number of features added to the statistical analysis. Panels on top show results from mean shift analysis while those on the bottom show tail effect analysis. Within each individual panel, the bars represent different metabolite panels as indicated by the symbols below and in the legend.

Figure 15:
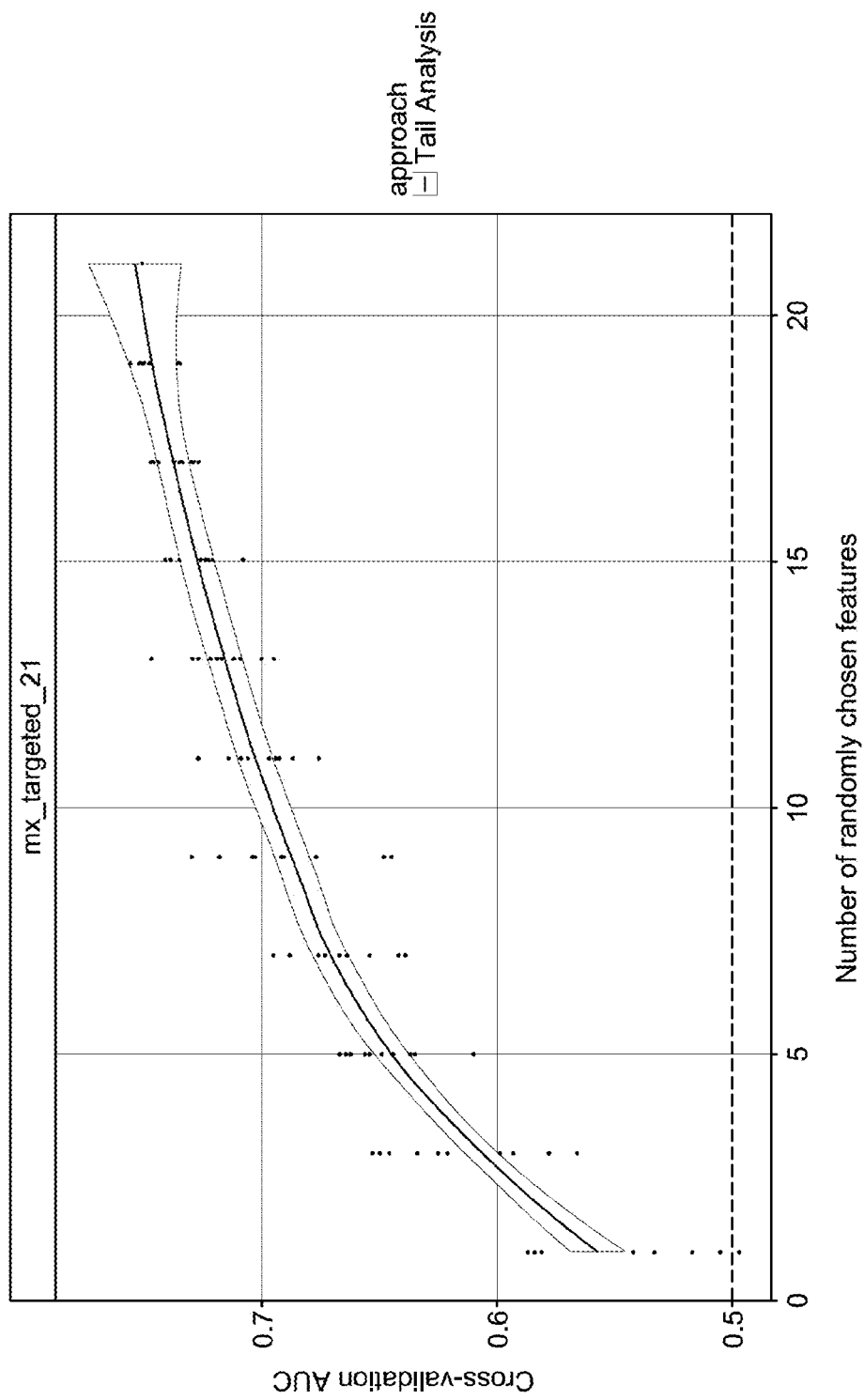
FIG. 15 illustrates the effects on the predictability of ASD by using an increasing number of metabolites selected from subsets of an exemplary 21-metabolite panel.

An exemplary plot describing cumulative AUC for ASD risk prediction when subsets total of 21 metabolites are assessed is shown in FIG. 15. In this figure, the x-axis shows the number of metabolites from subsets selected from a group of 21 metabolites. The y-axis shows the predicative power of ASD. For each number on the x-axis, a number of random metabolite combinations was analyzed and their AUC values plotted (dots). The curve shows the increased AUC that results from an increase in the number of metabolites used (selected from the group of 21). On the other hand, the figure demonstrates that even subsets having a small number of metabolites (e.g., 3 or 5) exhibit a high AUC. Thus, certain metabolites appear to have particularly important predictive tails.

An exemplary table describing representative subsets of the 21 metabolites from Table 1 containing 3, 4, 5, 6, and 7 metabolites that yield high AUC values is shown in Table 5. For each subset size (3, 4, 5, 6 or 7), 50 random selections of metabolite sets were analyzed. For example, for a subset of 3 from a 21-metabolite panel, 50 random combinations of a 3-metabolite subset were assessed (out of a total of 1330 possible permutations). Combinations from the 50 random sets with the highest AUC are shown. Thus, certain metabolite combinations containing fewer than 21 metabolites yielded high AUC values. Metabolites such as gamma-CEHC, p-cresol sulfate, xanthine, phenylacetylglutamine, isovalerylglycine, octenoylcarnitine, and hydroxy-chlorothalonil, appeared in multiple subsets that yielded high AUC values, indicating that these metabolites may be closely related to ASD status of a patient. Thus, these metabolites, alone or in combination with each other or additional metabolites, appear to be particularly useful for predicting the ASD risk of a patient.

TABLE 5

Exemplary subsets of metabolites and prediction of ASD

| Number of metabolites | Representative subset with high AUC | AUC |
| --- | --- | --- |
| 3 | gamma-CEHC, isovalerylglycine p-cresol sulfate | 0.675 |
| 4 | Octenoylcarnitine gamma-CEHC xanthine phenylacetylglutamine | 0.700 |
| 5 | 3-indoxyl sulfate 3-(3-hydroxyphenyl)propionate p-cresol sulfate gamma-CEHC Hydroxy-Chlorothalonil | 0.692 |
| 6 | phenylacetylglutamine indoleacetate xanthine Octenoylcarnitine hydroxyisovaleroylcarnitine (C5) pantothenate (Vitamin B5) | 0.731 |
| 7 | Octenoylcarnitine pantothenate (Vitamin B5) phenylacetylglutamine pipecolate xanthine indoleacetate 8-hydroxyoctanoate | 0.720 |

Two-metabolite subsets of the 21 metabolites from Table 1 were assessed for predictability of ASD in paired combinations. Representative paired combinations having a robust AUC are shown in Table 6. Similarly, three-metabolite subsets of the 21 metabolites from Table 1 were assessed for predictability of ASD in triplet combinations. Representative triplet combinations having a robust AUC are shown in Table 7.

TABLE 6

Exemplary metabolite pairs providing robust AUC

| Metabolites | AUC |
|---|---|
| phenylacetylglutamine, xanthine | 0.651 |
| phenylacetylglutamine, octenoylcarnitine | 0.647 |
| p-cresol sulfate, xanthine | 0.646 |
| isovalerylglycine, p-cresol sulfate | 0.646 |
| octenoylcarnitine, p-cresol sulfate | 0.645 |
| phenylacetylglutamine, isovalerylglycine | 0.643 |
| gamma-CEHC, p-cresol sulfate | 0.641 |
| indoleacetate, p-cresol sulfate | 0.635 |
| gamma-CEHC, xanthine | 0.633 |
| octenoylcarnitine, xanthine | 0.632 |
| isovalerylglycine, pipecolate | 0.632 |
| Hydroxyl=chlorothalonil, p-cresol sulfate | 0.631 |
| phenylacetylglutamine, indoleacetate | 0.629 |
| pipecolate, p-cresol sulfate | 0.629 |
| phenylacetylglutamine, p-cresol sulfate | 0.628 |
| 1,5-anhydroglucitol (1,5-AG), p-cresol sulfate | 0.628 |
| phenylacetylglutamine, lactate | 0.627 |
| p-cresol sulfate, lactate | 0.627 |
| 3-(3-hydroxyphenyl)propionate, 3-indoxyl sulfate | 0.625 |
| pantothenate (Vitamin B5), p-cresol sulfate | 0.625 |

TABLE 7

Exemplary metabolite triplets providing robust AUC

| Metabolites | AUC |
|---|---|
| phenylacetylglutamine, octenoylcarnitine, xanthine | 0.685 |
| phenylacetylglutamine, octenoylcarnitine, indoleacetate | 0.681 |
| phenylacetylglutamine, isovalerylglycine, octenoylcarnitine | 0.678 |
| isovalerylglycine, octenoylcarnitine, p-cresol sulfate | 0.678 |
| isovalerylglycine, octenoylcarnitine, pipecolate | 0.677 |
| indoleacetate, isovalerylglycine, p-cresol sulfate | 0.676 |
| octenoylcarnitine, p-cresol sulfate, xanthine | 0.673 |
| phenylacetylglutamine, isovalerylglycine, xanthine | 0.671 |
| pantothenate (Vitamin B5), p-cresol sulfate, xanthine | 0.671 |
| isovalerylglycine, octenoylcarnitine, lactate | 0.670 |
| phenylacetylglutamine, isovalerylglycine, indoleacetate | 0.670 |
| gamma-CEHC, isovalerylglycine, p-cresol sulfate | 0.670 |
| indoleacetate, octenoylcarnitine, p-cresol sulfate | 0.668 |
| phenylacetylglutamine, pipecolate, xanthine | 0.668 |
| pipecolate, p-cresol sulfate, xanthine | 0.668 |
| octenoylcarnitine, hydroxy-chlorothalonil, p-cresol sulfate | 0.667 |
| phenylacetylglutamine, isovalerylglycine, gamma-CEHC | 0.667 |
| phenylacetylglutamine, xanthine, gamma-CEHC | 0.667 |
| phenylacetylglutamine, p-cresol sulfate, xanthine | 0.666 |
| indoleacetate, hydroxy-chlorothalonil, p-cresol sulfate | 0.666 |

Example 5

Validation of the 12-Metabolite Panel Classifier

Data from 180 samples tested, of which approximately two thirds were ASD, was used to generate a classifier based on the 12 highly informative metabolites shown in FIG. 7. The classifier was tested for the ability to discriminate ASD from non-ASD (here, DD) in a second cohort of 130 samples. This method provided an unbiased estimate of true predictive performance, corresponding to an AUC of 0.74. A schematic of the process is shown in FIG. 12.

Example 6

Adding Genetic Information to Metabolites May Improve ASD Risk Prediction

Figure 16A:
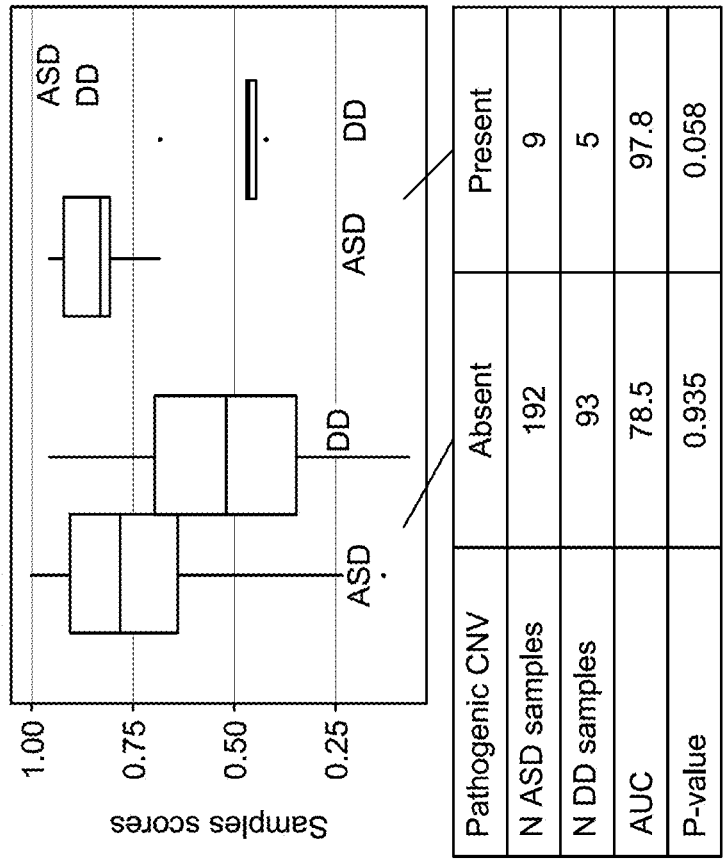
FIG. 16A illustrates the effects of adding genetic information to the tail effect analysis using an exemplary 12-metabolite panel, demonstrating improved power of separating ASD from non-ASD.
Figure 16B:
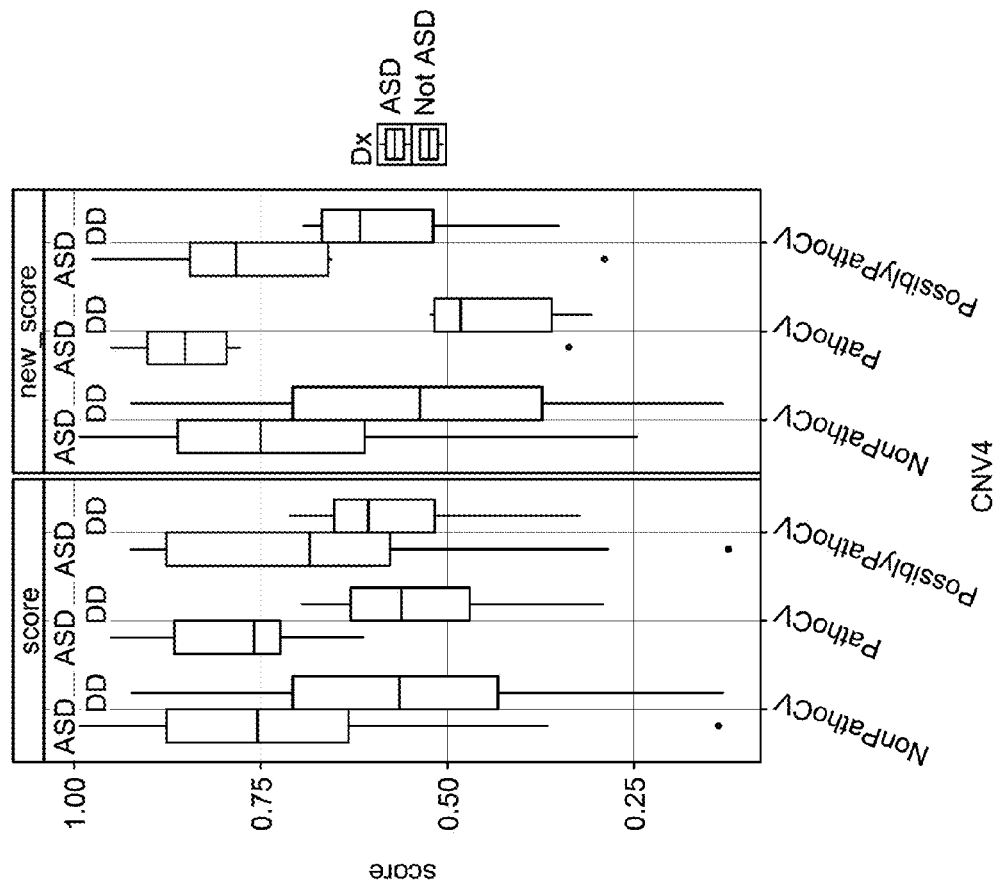
FIG. 16B illustrates the effects of adding genetic information to the tail effect analysis using an exemplary 21-metabolite panel, demonstrating improved power of separating ASD from non-ASD.
Figure 17A:
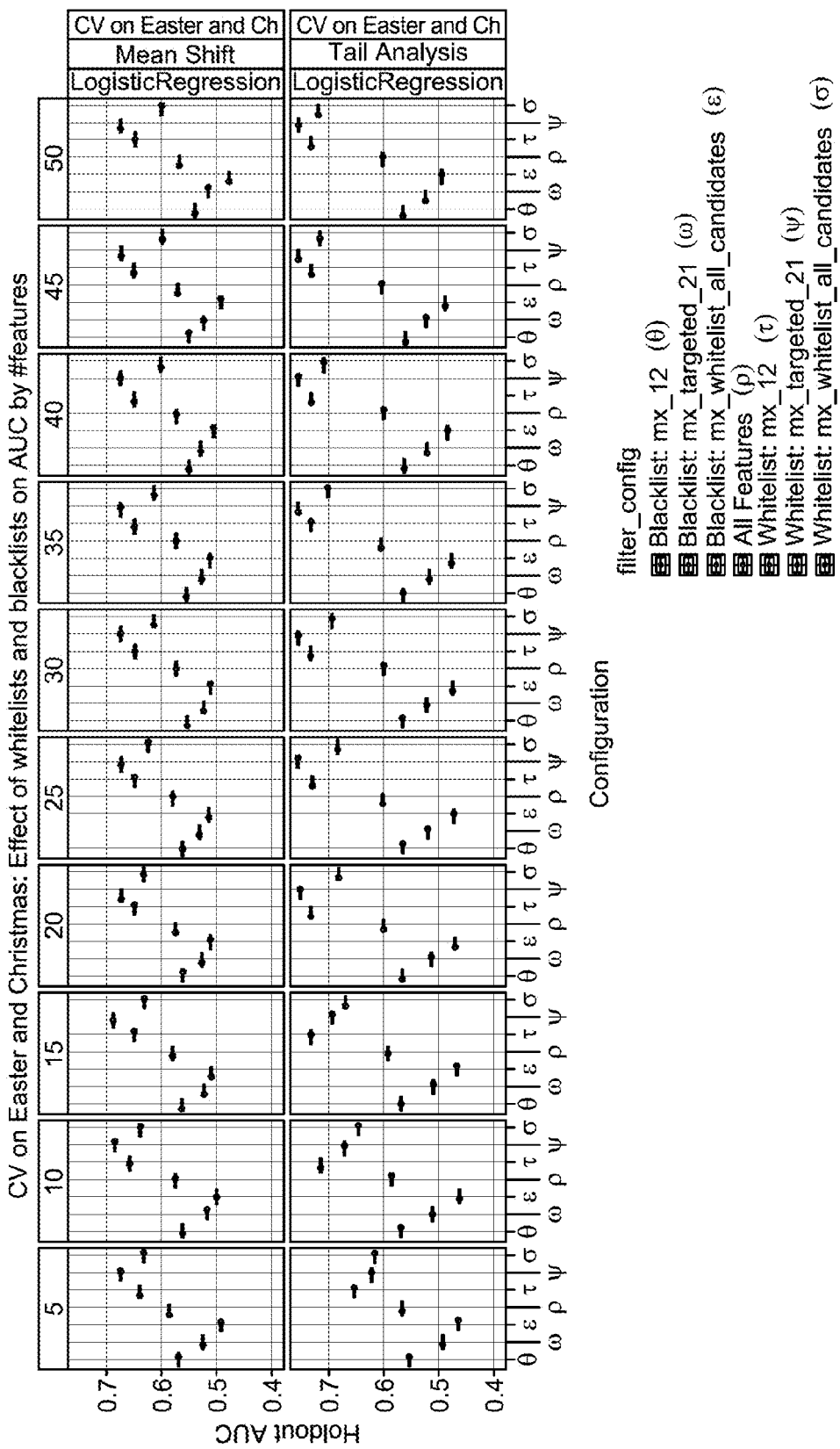
FIGS. 17A-B illustrate the effects on the predictability of ASD by the inclusion and exclusion of an exemplary 21-metabolite panel from the total number metabolites, by comparing tail effect analysis to mean shift analysis, and by comparing logistic regression to Bayes analysis. (Blacklist=excluded, Whitelist=included, mx_12=exemplary 12-metabolite panel, mx_targeted 21=exemplary 21-metabolite panel, mx_all_candidates=84 candidate metabolites, all features=total set of 600 metabolites)
Figure 17B:
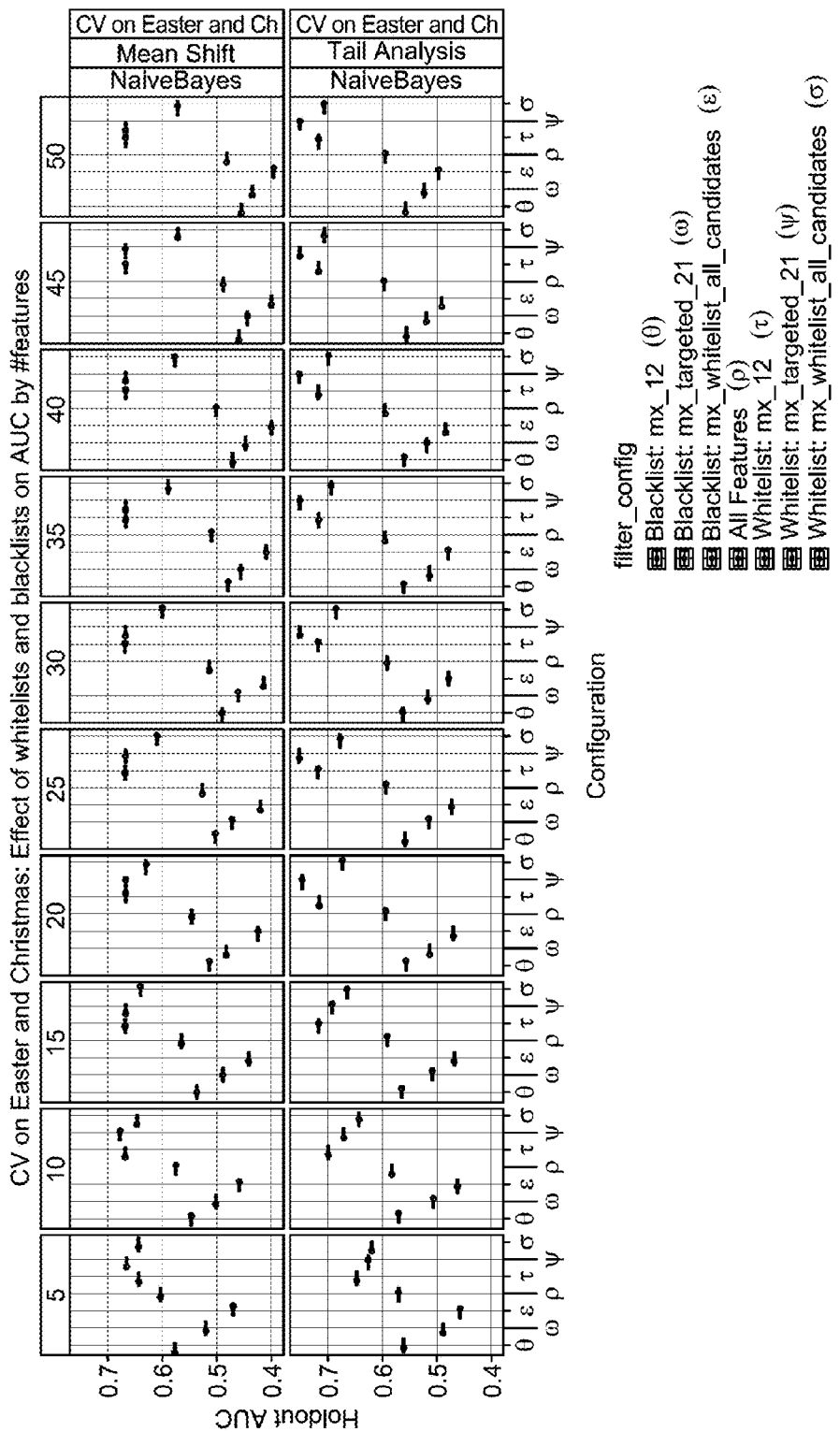
Figure 18A:
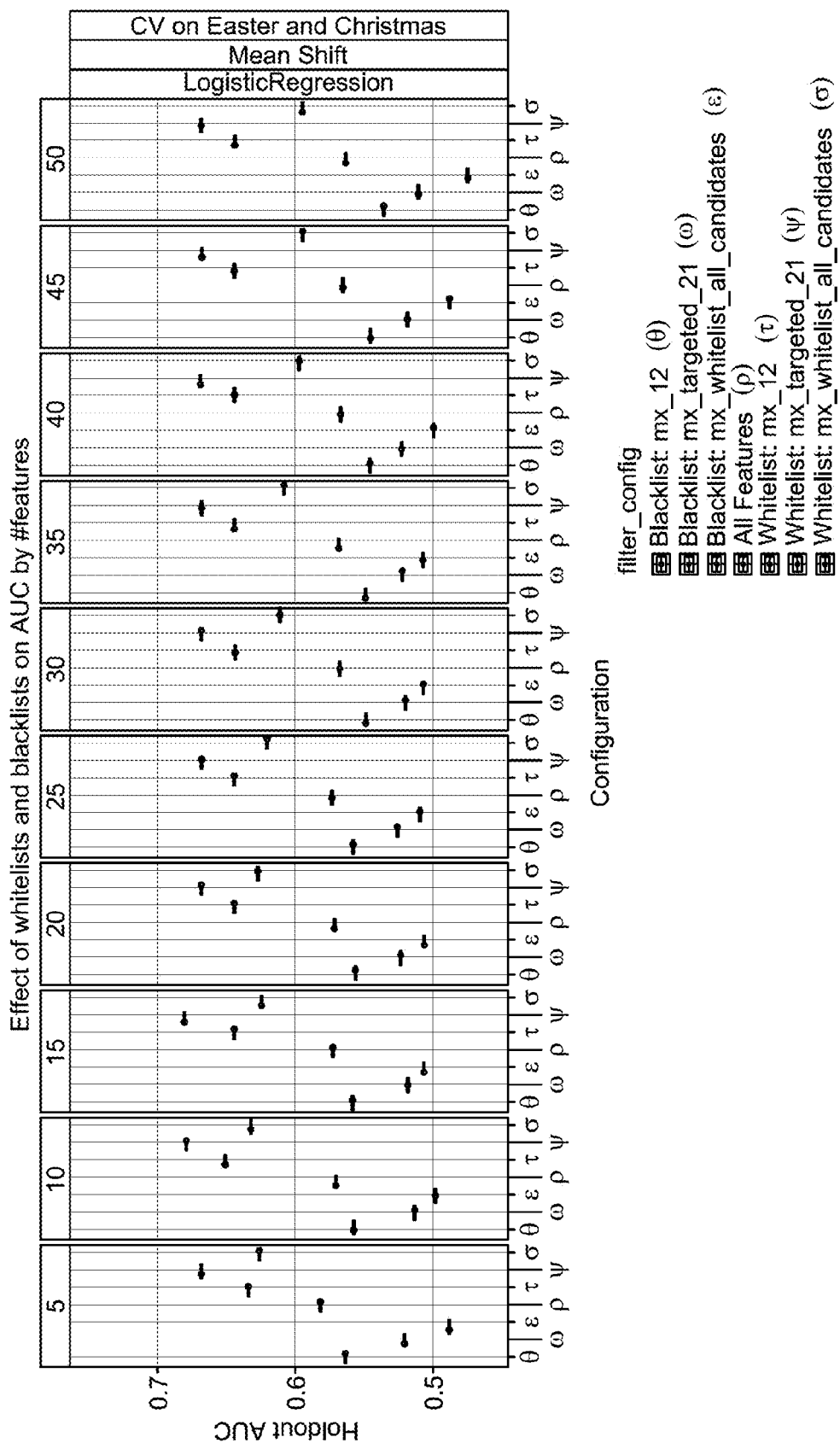
FIGS. 18A-B illustrate the effects on the predictability of ASD by the inclusion and exclusion of an exemplary 21-metabolite panel from the total number metabolites, by comparing tail effect analysis to mean shift analysis, and by using logistic regression in two cohorts (i.e., "Christmas" and "Easter"). (Blacklist=excluded, Whitelist=included, mx_12=exemplary 12-metabolite panel, mx_targeted 21=exemplary 21-metabolite panel, mx_all_candidates=84 candidate metabolites, all features=total set of 600 metabolites)
Figure 18B:
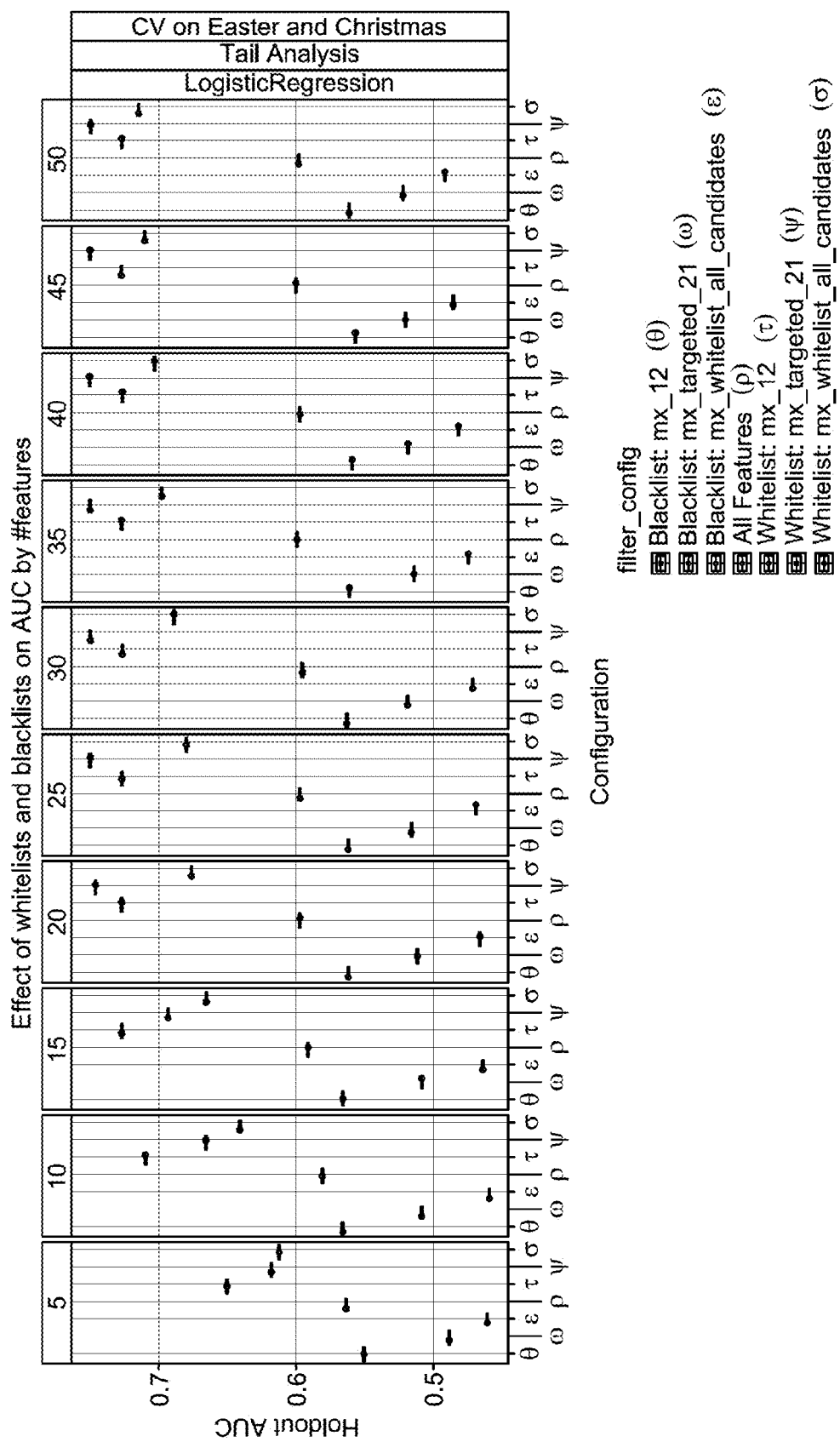
Figure 19A:
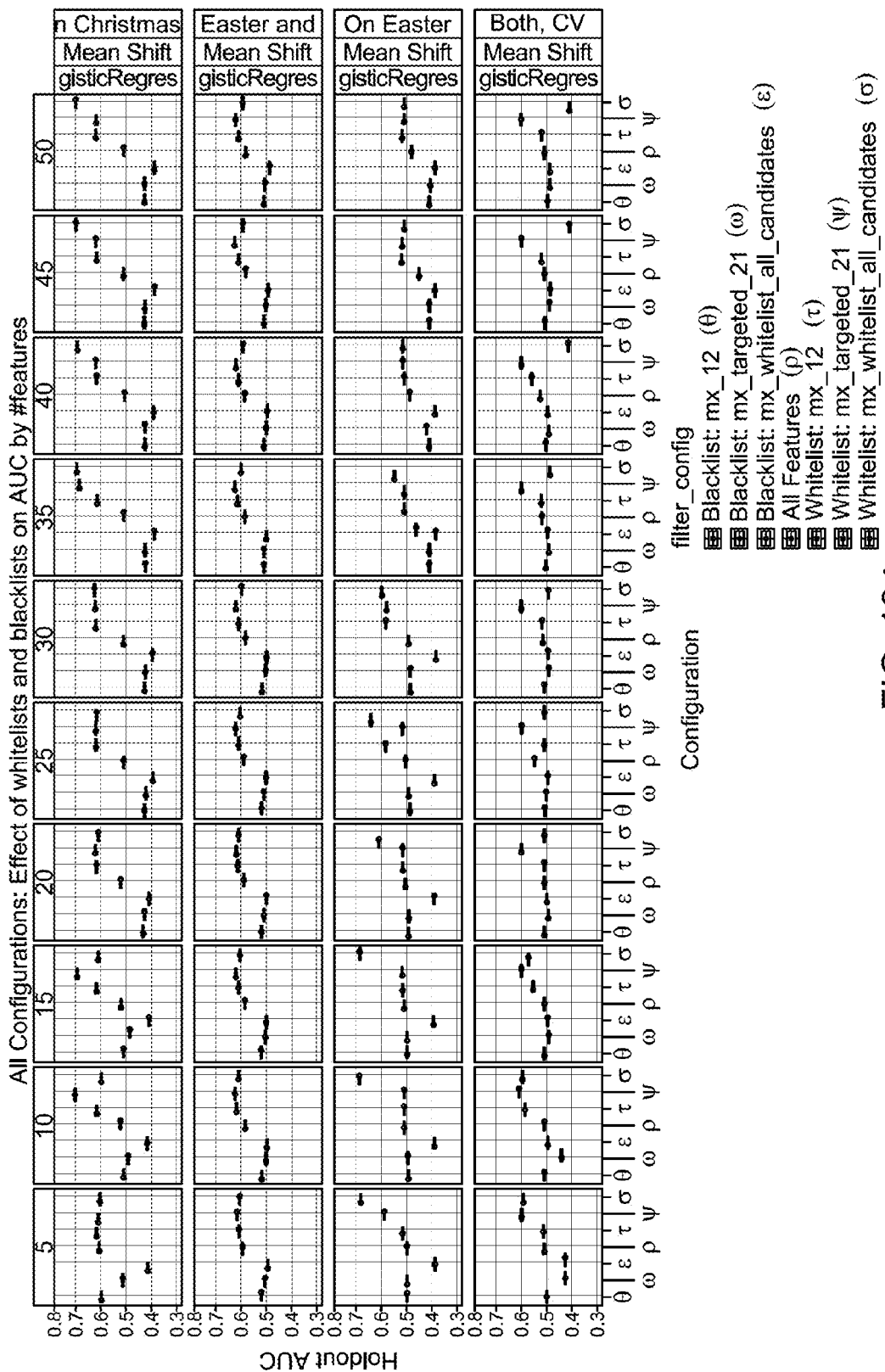
FIGS. 19A-D illustrate the effects on the predictability of ASD by the inclusion and exclusion of an exemplary 21-metabolite panel from the total number metabolites, by comparing tail effect analysis to mean shift analysis, and by comparing logistic regression to Bayes analysis using either the "Christmas" cohort, or the "Easter" cohort, or both combined. (Blacklist=excluded, Whitelist=included, mx_12=exemplary 12-metabolite panel, mx_targeted 21=exemplary 21-metabolite panel, mx_all_candidates=84 candidate metabolites, all features=total set of 600 metabolites)
Figure 19B:
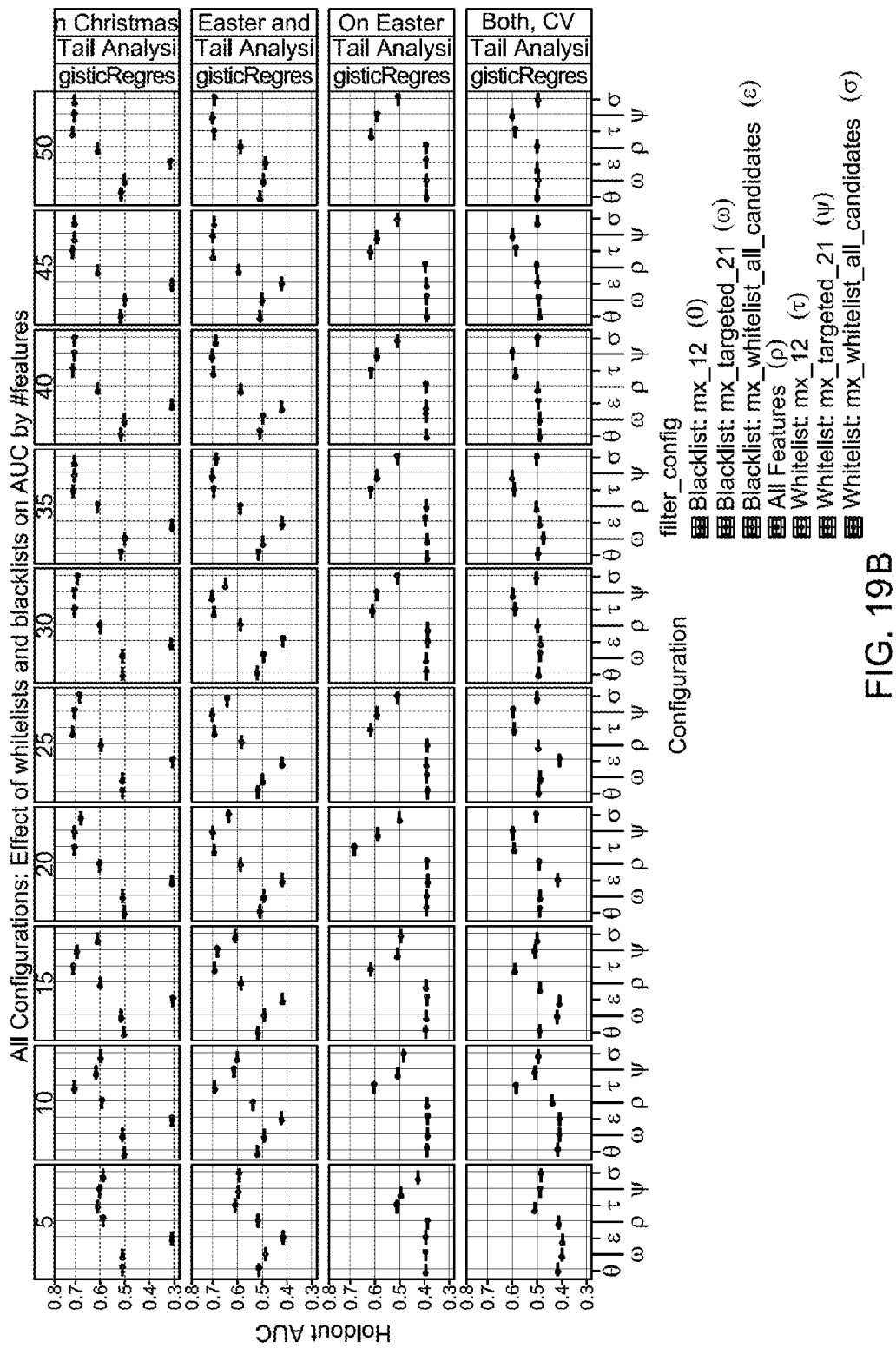
Figure 19C:
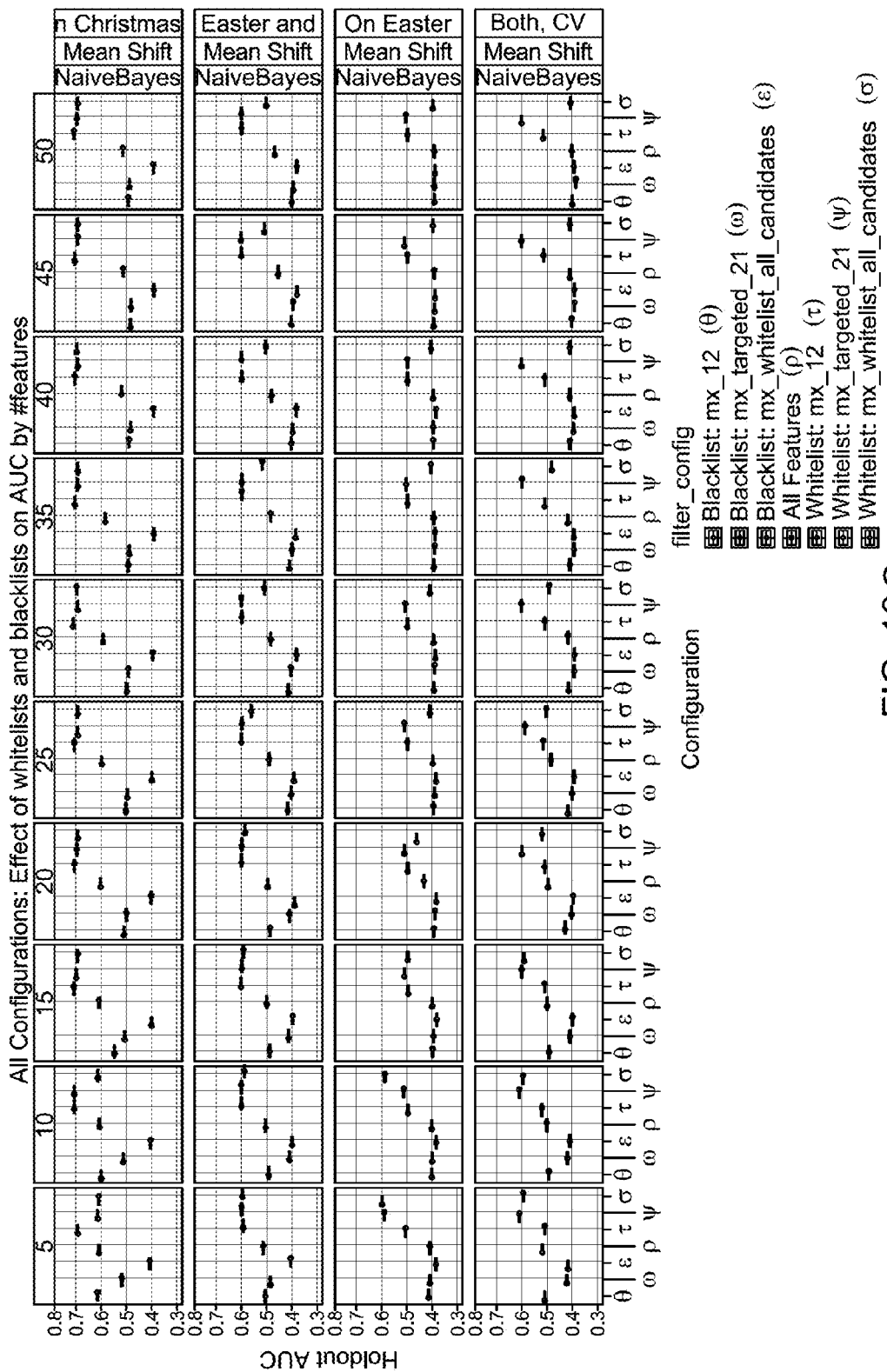
Figure 19D:
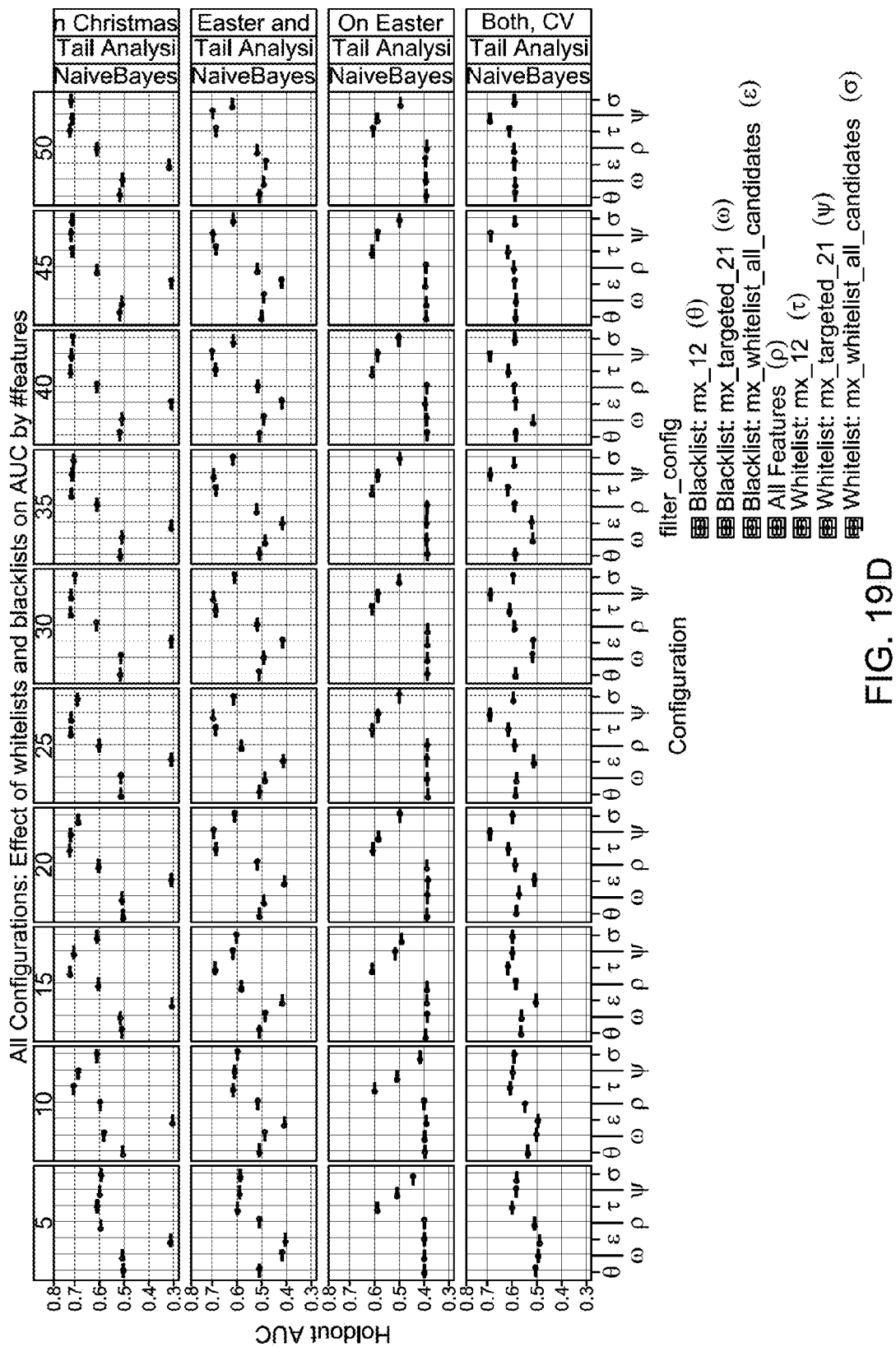
Figure 20:
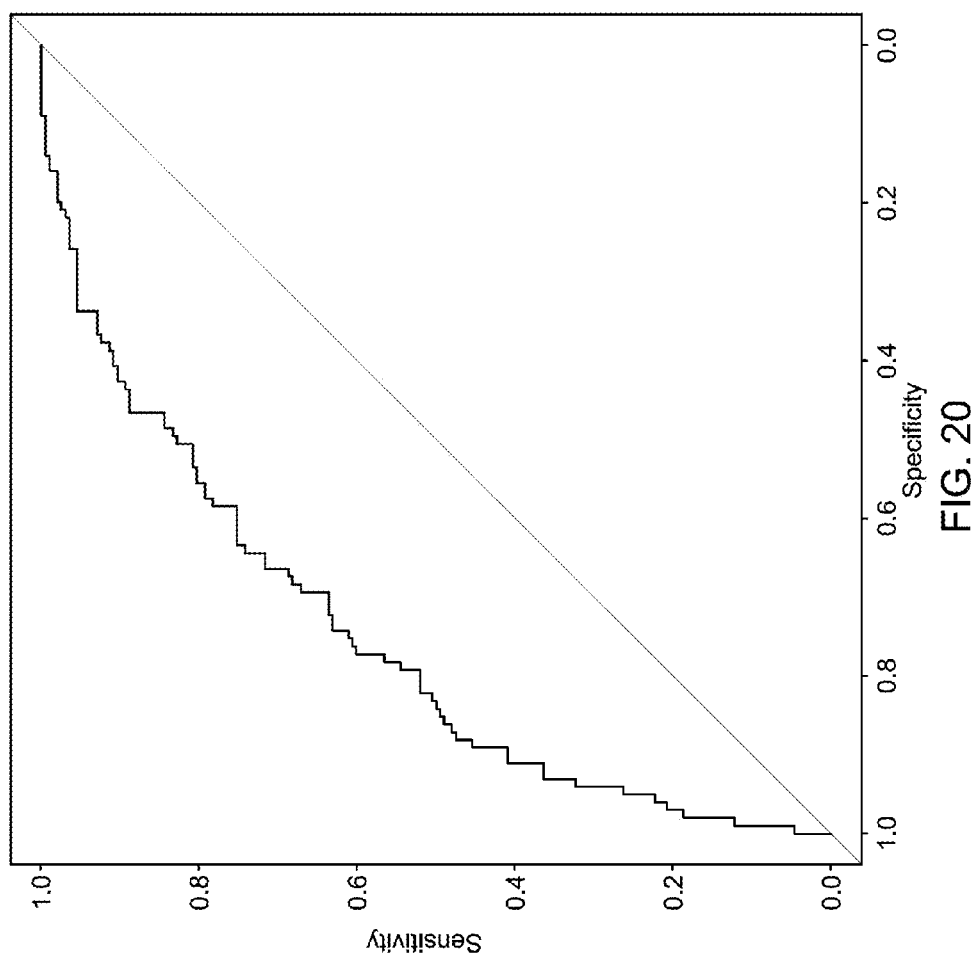
FIG. 20 illustrates a representative plot of the specificity and sensitivity of tail effect analysis for an exemplary 21-metabolite panel for prediction of ASD.

Adding genetic information to metabolite information was found to improve ASD risk prediction for certain groups. For example, combining copy number variation (CNVs) data with metabolite information significantly reduces the confidence interval of ASD risk prediction as shown in FIGS. 16A and 16B. As FIG. 16A demonstrates, adding genetic information further enhances the separation between ASD and non-ASD groups. In addition to CNV, other genetic information, including, but not limited to, Fragile X (FXS) status, may further contribute to a diagnostic test that can predict ASD risk with improved accuracy and reduction type I and/or type II errors. As shown in FIG. 16B, including such additional information (e.g., "PathoCV"), increased the separation between ASD and DD groups, and thus helped differentiate between these two conditions.

Example 7

Prominent Biological Pathways Emerging from Metabolite Analysis

Further analysis of metabolite information revealed clusters of metabolites presented in Table 1 that play a prominent role in distinct biological pathways. For example, 7 of 21 metabolites are related to gut microbial activities (33%) and are shown in Table 8. All 7 are amino acid metabolites. Six of 7 are metabolites of aromatic amino acids and have a benzene ring.

TABLE 8

Seven metabolites involved in gut microbial activity

| Metabolite | Change in ASD in the STORY cohort | Benzene ring | Bacterially derived | Original precursor |
|---|---|---|---|---|
| 3-indoxyl sulfate | ASD down | Yes | yes | Tryptophan |
| indoleacetate | ASD down | Yes | yes | Tryptophan |
| p-cresol sulfate | ASD down | Yes | yes | Phenylalanine or Tyrosine |
| 4-ethylphenyl sulfate | ASD down | Yes | yes | Phenylalanine or Tyrosine |
| phenylacetylglutamine | ASD down | Yes | yes | Phenylalanine or Tyrosine |
| 3-(3-hydroxyphenyl)-propionate | DD down | Yes | yes | Phenylalanine or Tyrosine |
| pipecolate | ASD up | No | yes | Lysine |

Analysis of the metabolites that are strongly associated with ASD, as shown in Table 1, reveals connections with certain biological pathways. For example, particular metabolites that provide predictive information for ASD suggested impairment of phase II biotransformation, impaired ability metabolize benzene rings, dysregulation of reabsorption in kidneys, dysregulation of carnitine metabolism, and imbalance of transport of large neutral amino acids into brain. Biological pathway information can be further utilized to improve ASD risk assessment and/or explore etiology and pathophysiology of ASD. Such information can also be used to develop medicinal therapeutics for treatment ASD.

Example 8

Elucidation of Metabolite Concentrations in Blood

Absolute metabolite concentrations in plasma samples were determined for 19 of the 21 metabolites described in Example 2 by mass spectrometry. Absolute metabolite concentrations in plasma (ng/ml) were calculated using calibration curves generated from standard samples containing known amounts of metabolites.

Table 9A shows seventeen metabolites predictive of ASD. The direction of the tail effect (left or right), threshold values for determining the presence of a tail effect (i.e., $15^{th}$ percentile for left tail effect and $90^{th}$ percentile for a right tail effect), and odds ratios (log 2) are provided. A positive odds ratio indicates that a tail effect of the metabolite is predictive of ASD.

Table 9B shows seven metabolites predictive of DD. The direction of the tail effect (left or right), threshold values for determining the presence of a tail effect (i.e., $15^{th}$ percentile for left tail effect and $90^{th}$ percentile for a right tail effect), and odds ratios (log 2) are provided. A negative odds ratio indicates that a tail effect of the metabolite is predictive of DD.

TABLE 9A

Exemplary metabolites with tail enrichment predictive of ASD

| Metabolite | Direction of tail effect | Threshold concentration (ng/ml) | Odds ratio (log2) |
| --- | --- | --- | --- |
| 3-carboxy-4-methyl-5-propyl-2-furanpropanoate (CMPF) | Left | 7.98 | 0.85 |
| 3-indoxyl sulfate | Left | 256.7 | 1.7 |
| 4-ethylphenyl sulfate | Left | 3.0 | 1.3 |
| 5-hydroxyindoleacetate | Right | 28.5 | 2.3 |
| gamma-CEHC | Left | 32.01 | 0.8 |
| hydroxyisovaleroylcarnitine (C5) | Left | 12.9 | 3.0 |
| indoleacetate | Left | 141.4 | 1.5 |
| isovalerylglycine | Left | 1.6 | 1.0 |
| lactate | Right | 686600.0 | 1.61 |

TABLE 9A-continued

Exemplary metabolites with tail enrichment predictive of ASD

| Metabolite | Direction of tail effect | Threshold concentration (ng/ml) | Odds ratio (log2) |
| --- | --- | --- | --- |
| N1-Methyl-2-pyridone-5-carboxamide | Left | 124.82 | 0.94 |
| p-cresol sulfate | Left | 1220.0 | 1.6 |
| pantothenate (Vitamin B5) | Right | 63.3 | 1.7 |
| phenylacetylglutamine | Left | 166.4 | 1.3 |
| pipecolate | Right | 303.6 | 2.3 |
| xanthine | Right | 182.7 | 1.6 |
| hydroxy-chlorothalonil | Right | 20.3 | 2.2 |
| 1,5-anhydroglucitol (1,5-AG) | Left | 11910.3 | 1.9 |

TABLE 9B

Exemplary metabolites with tail enrichment predictive of DD

| Metabolite | Tail Effect | Threshold concentration (ng/ml) | Odds Ratio (log2) |
| --- | --- | --- | --- |
| 3-(3-hydroxyphenyl)propionate | Left | 5.0 | −1.5 |
| 3-indoxyl sulfate | Right | 926.6 | −1.1 |
| isovalerylglycine | Right | 5.2 | −1.3 |
| phenylacetylglutamine | Right | 513.2 | −1.5 |
| xanthine | Left | 88.0 | −1.8 |
| 3-hydroxyhippurate | Left | 0.86 | −1.25 |
| 1,5-anhydroglucitol (1,5-AG) | Right | 20600.3 | −1.1 |

What is claimed is:

1. A method comprising measuring by mass spectrometry the levels of a plurality of metabolites in a blood sample obtained from a human subject, wherein the plurality of metabolites comprises hydroxychlorothalonil and at least one metabolite selected from the group consisting of xanthine, gamma-CEHC, 5-hydroxyindoleacetate (5-HIAA), indoleacetate, p-cresol sulfate, 1,5-anhydroglucitol (1,5-AG), 3-carboxy-4-methyl-5-propyl-2-furanpropanoate (CMPF), 3-indoxyl sulfate, 4-ethylphenyl sulfate, hydroxy-isovaleroylcarnitine (C5), isovalerylglycine, lactate, N1-Methyl-2-pyridone-5-carboxamide, pantothenate (Vitamin B5), phenylacetylglutamine, pipecolate, 3-hydroxyhippurate.

2. The method of claim 1, wherein the plurality of metabolites further comprises xanthine and gamma-CEHC.

3. The method of claim 1, wherein the blood sample is a plasma sample.

4. The method of claim 1, wherein the subject is no greater than about 54 months of age.

5. The method of claim 1, wherein the subject is no greater than about 36 months of age.

* * * * *